US011952585B2

(12) United States Patent
Francone et al.

(10) Patent No.: US 11,952,585 B2
(45) Date of Patent: Apr. 9, 2024

(54) METHODS OF TREATING PHENYLKETONURIA

(71) Applicant: HOMOLOGY MEDICINES, INC., Bedford, MA (US)

(72) Inventors: Omar L. Francone, Waltham, MA (US); Deborah A. Kinch, Bedford, MA (US); Diana Lamppu, Roslindale, MA (US); Albert Barnes Seymour, Westborough, MA (US); Teresa Leah Wright, Lexington, MA (US)

(73) Assignee: HOMOLOGY MEDICINES, INC., Bedford, MA (US)

( * ) Notice: Subject to any disclaimer, the term of this patent is extended or adjusted under 35 U.S.C. 154(b) by 160 days.

(21) Appl. No.: 17/147,974

(22) Filed: Jan. 13, 2021

(65) Prior Publication Data
US 2021/0261983 A1    Aug. 26, 2021

Related U.S. Application Data

(60) Provisional application No. 63/110,251, filed on Nov. 5, 2020, provisional application No. 62/960,498, filed on Jan. 13, 2020.

(51) Int. Cl.
| | |
|---|---|
| *C12N 15/864* | (2006.01) |
| *A61K 48/00* | (2006.01) |
| *C12N 7/00* | (2006.01) |
| *C12N 7/01* | (2006.01) |
| *C12N 9/02* | (2006.01) |
| *C12N 15/52* | (2006.01) |
| *C12N 15/86* | (2006.01) |
| *A61K 31/573* | (2006.01) |

(52) U.S. Cl.
CPC ........... *C12N 15/86* (2013.01); *C12N 7/00* (2013.01); *C12N 9/0071* (2013.01); *A61K 31/573* (2013.01); *C12N 2750/14143* (2013.01); *C12N 2830/008* (2013.01); *C12N 2830/50* (2013.01); *C12Y 114/16001* (2013.01)

(58) Field of Classification Search
None
See application file for complete search history.

(56) References Cited

U.S. PATENT DOCUMENTS

| | | | |
|---|---|---|---|
| 5,252,479 A | 10/1993 | Srivastava |
| 5,474,935 A | 12/1995 | Chatterjee et al. |
| 5,589,377 A | 12/1996 | Lebkowski et al. |
| 5,622,856 A | 4/1997 | Natsoulis |
| 5,650,309 A | 7/1997 | Wong-Staal et al. |
| 5,753,500 A | 5/1998 | Shenk et al. |
| 5,780,447 A | 7/1998 | Nienhuis |
| 5,895,759 A | 4/1999 | Strauss et al. |
| 6,025,195 A | 2/2000 | Sandig et al. |
| 6,153,436 A | 11/2000 | Hermonat et al. |
| 6,156,303 A | 12/2000 | Russell et al. |
| 6,180,613 B1 | 1/2001 | Kaplitt et al. |
| 6,238,914 B1 | 5/2001 | Boyce |
| 6,268,212 B1 | 7/2001 | Simonet |
| 6,329,181 B1 | 12/2001 | Xiao et al. |
| 6,338,962 B1 | 1/2002 | Boyce |
| 6,387,670 B1 | 5/2002 | Leblois-Prehaud et al. |
| 6,610,906 B1 | 8/2003 | Kurachi et al. |
| 6,759,237 B1 | 7/2004 | Wilson et al. |
| 6,919,209 B1 | 7/2005 | Chatterjee et al. |
| 6,924,128 B2 | 8/2005 | Allen |
| 6,936,243 B2 | 8/2005 | Snyder et al. |
| 6,936,466 B2 | 8/2005 | Feldhaus |
| 6,953,690 B1 | 10/2005 | Gao et al. |
| 6,984,517 B1 | 1/2006 | Chiorini et al. |
| 7,001,764 B2 | 2/2006 | Little et al. |
| 7,022,519 B2 | 4/2006 | Gao et al. |
| 7,056,502 B2 | 6/2006 | Hildinger et al. |
| 7,091,029 B2 | 8/2006 | Hwang |
| 7,094,604 B2 | 8/2006 | Snyder et al. |
| 7,148,341 B2 | 12/2006 | Kleinschmidt et al. |
| 7,157,571 B2 | 1/2007 | Wang et al. |
| 7,172,893 B2 | 2/2007 | Rabinowitz et al. |
| 7,179,903 B2 | 2/2007 | McArthur et al. |
| 7,198,951 B2 | 4/2007 | Gao et al. |
| 7,220,577 B2 | 5/2007 | Zolotukhin |
| 7,235,393 B2 | 6/2007 | Gao et al. |
| 7,259,151 B2 | 8/2007 | Arbetman et al. |

(Continued)

FOREIGN PATENT DOCUMENTS

| | | |
|---|---|---|
| EP | 126544 A2 | 11/1984 |
| EP | 161788 A1 | 11/1985 |

(Continued)

OTHER PUBLICATIONS

Levy et al, Phenylalanine ammonia lyase (PAL): From discovery to enzyme substitution therapy for phenylketonuria, Mol Genet Metab. Aug. 2018;124(4):223-229.*

Grisch-Chan, State-of-the-Art 2019 on Gene Therapy for Phenylketonuria, Human Gen Therapy, 2019, pp. 1274-1283.*

BioMarin, U.S. FDA Placed a Clinical Hold on BMN 307 Phearless Phase 1/2 Gene Therapy Study in Adults with PKU Based on Interim Pre-clinical Study Findings, 2021, pp. 1-2.*

Mendell et al, Current Clinical Applications of In Vivo Gene Therapy with AAVs, Molecular Therapy vol. 29 No Feb. 2, 2021, p. 464-488.*

(Continued)

*Primary Examiner* — Maria Marvich
(74) *Attorney, Agent, or Firm* — Dechert LLP; Andrew T. Wilkins

(57) ABSTRACT

Provided herein are methods of treating a subject having a disease or disorder associated with a PAH gene mutation. The methods generally comprise administering to the subject a therapeutically effective does of a recombinant adeno-associated virus (rAAV) that can express a phenylalanine hydroxylase (PAH) polypeptide in a cell and thereby restore PAH gene function in the subject.

17 Claims, 16 Drawing Sheets

Specification includes a Sequence Listing.

(56) References Cited

U.S. PATENT DOCUMENTS

| | | |
|---|---|---|
| 7,282,199 B2 | 10/2007 | Gao et al. |
| 7,351,813 B2 | 4/2008 | Miao et al. |
| 7,465,583 B2 | 12/2008 | Sumulski et al. |
| 7,482,156 B2 | 1/2009 | Arroyo et al. |
| 7,588,772 B2 | 9/2009 | Kay et al. |
| 7,749,492 B2 | 7/2010 | Bartlett et al. |
| 7,790,154 B2 | 9/2010 | Samulski et al. |
| 7,906,111 B2 | 3/2011 | Wilson et al. |
| 8,030,065 B2 | 10/2011 | Gray |
| 8,067,156 B2 | 11/2011 | Kaplitt et al. |
| 8,163,543 B2 | 4/2012 | Urabe et al. |
| 8,168,425 B2 | 5/2012 | Gray |
| 8,241,622 B2 | 8/2012 | Engelhardt et al. |
| 8,283,151 B2 | 10/2012 | Schmidt et al. |
| 8,298,818 B2 | 10/2012 | Boye et al. |
| 8,476,418 B2 | 7/2013 | Mueller et al. |
| 8,524,446 B2 | 9/2013 | Gao et al. |
| 8,628,966 B2 | 1/2014 | Chatterjee et al. |
| 8,632,764 B2 | 1/2014 | Xiao et al. |
| 8,716,461 B2 | 5/2014 | Delwart et al. |
| 8,846,387 B2 | 9/2014 | Russell et al. |
| 8,846,389 B2 | 9/2014 | Chiorini et al. |
| 8,926,958 B2 | 1/2015 | Shah et al. |
| 8,999,678 B2 | 4/2015 | Vandenberghe et al. |
| 8,999,948 B2 | 4/2015 | Tubert et al. |
| 9,150,882 B2 | 10/2015 | Kay et al. |
| 9,169,299 B2 | 10/2015 | Lisowski et al. |
| 9,169,494 B2 | 10/2015 | Hewitt et al. |
| 9,193,956 B2 | 11/2015 | Schaffer et al. |
| 9,217,155 B2 | 12/2015 | Gao et al. |
| 9,222,105 B2 | 12/2015 | Cost et al. |
| 9,402,919 B2 | 8/2016 | Roeth et al. |
| 9,408,904 B2 | 8/2016 | Wright et al. |
| 9,409,953 B2 | 8/2016 | Asokan et al. |
| 9,441,244 B2 | 9/2016 | Schaffer et al. |
| 9,617,548 B2 | 4/2017 | Chuah et al. |
| 9,764,045 B2 | 9/2017 | Nathwani et al. |
| 9,783,824 B2 | 10/2017 | Kay et al. |
| 9,840,719 B2 | 12/2017 | High et al. |
| 9,890,396 B2 | 2/2018 | Chatterjee et al. |
| 11,419,950 B2* | 8/2022 | Vandendriessche ... C12N 15/86 |
| 2003/0129203 A1 | 7/2003 | Vega et al. |
| 2003/0130221 A1 | 7/2003 | High et al. |
| 2003/0198620 A1 | 10/2003 | Ozawa et al. |
| 2004/0086485 A1 | 5/2004 | Aguilar-Cordova |
| 2004/0142416 A1 | 7/2004 | Laipis et al. |
| 2004/0235174 A1 | 11/2004 | Grimm et al. |
| 2005/0112765 A1 | 5/2005 | Li et al. |
| 2009/0191597 A1 | 7/2009 | Samulski et al. |
| 2009/0215879 A1 | 8/2009 | Diprimio et al. |
| 2010/0297084 A1 | 11/2010 | Bennett et al. |
| 2010/0316623 A1 | 12/2010 | Turner et al. |
| 2012/0046349 A1 | 2/2012 | Bell et al. |
| 2012/0093772 A1 | 4/2012 | Horsager et al. |
| 2012/0244127 A1 | 9/2012 | Lipschutz et al. |
| 2013/0023033 A1 | 1/2013 | Wilson et al. |
| 2013/0189225 A1 | 7/2013 | Voit et al. |
| 2013/0310443 A1 | 11/2013 | Srivastava et al. |
| 2013/0323226 A1 | 12/2013 | Wilson et al. |
| 2014/0037585 A1 | 2/2014 | Wright et al. |
| 2014/0050701 A1 | 2/2014 | Zhong et al. |
| 2014/0107185 A1 | 4/2014 | Maclaren et al. |
| 2014/0271550 A1 | 9/2014 | Rabinowitz et al. |
| 2014/0336245 A1 | 11/2014 | Mingozzi et al. |
| 2014/0359799 A1 | 12/2014 | Wang et al. |
| 2015/0023924 A1 | 1/2015 | High et al. |
| 2015/0024467 A1 | 1/2015 | Sheldon et al. |
| 2015/0065562 A1 | 3/2015 | Yazicioglu et al. |
| 2015/0079038 A1 | 3/2015 | Deverman et al. |
| 2015/0110762 A1 | 4/2015 | Holmes et al. |
| 2015/0111955 A1 | 4/2015 | High et al. |
| 2015/0184197 A1 | 7/2015 | Davidson et al. |
| 2015/0238550 A1 | 8/2015 | McCown et al. |
| 2015/0315610 A1 | 11/2015 | Nishie et al. |
| 2015/0352228 A1 | 12/2015 | Torbett et al. |
| 2015/0374803 A1 | 12/2015 | Wolfe |
| 2015/0376240 A1 | 12/2015 | Cronin et al. |
| 2016/0000887 A1 | 1/2016 | Wilson et al. |
| 2016/0017295 A1 | 1/2016 | Schaffer et al. |
| 2016/0032319 A1 | 2/2016 | Wright et al. |
| 2016/0123990 A1 | 5/2016 | High et al. |
| 2016/0175365 A1 | 6/2016 | Golden |
| 2016/0229904 A1 | 8/2016 | Xiao et al. |
| 2017/0119906 A1 | 5/2017 | Riley |
| 2017/0211094 A1 | 7/2017 | Chatterjee et al. |
| 2017/0211095 A1* | 7/2017 | Chatterjee ............... C12N 15/86 |
| 2017/0326256 A1 | 11/2017 | Doering et al. |
| 2019/0231901 A1 | 8/2019 | Seymour et al. |
| 2019/0336550 A1 | 11/2019 | Wilson et al. |
| 2021/0348135 A1* | 11/2021 | Kyostio-Moore ........................... C12Y 114/16001 |
| 2022/0001028 A1* | 1/2022 | Hatfield ............... A61K 48/005 |

FOREIGN PATENT DOCUMENTS

| | | |
|---|---|---|
| EP | 746624 B1 | 12/2001 |
| EP | 1497436 B1 | 7/2007 |
| WO | WO-1996008560 A1 | 3/1996 |
| WO | WO-1998009524 A1 | 3/1998 |
| WO | WO-1998021349 A1 | 5/1998 |
| WO | WO-1998027207 A1 | 6/1998 |
| WO | WO-1998028417 A1 | 7/1998 |
| WO | WO-1999003981 A1 | 1/1999 |
| WO | WO-1999018227 A1 | 4/1999 |
| WO | WO-1999055564 A1 | 11/1999 |
| WO | WO-1999064569 A1 | 12/1999 |
| WO | WO-2000049160 A1 | 8/2000 |
| WO | WO-2001036620 A2 | 5/2001 |
| WO | WO-2002066611 A2 | 8/2002 |
| WO | WO-2003087383 A1 | 10/2003 |
| WO | WO-2003093436 A2 | 11/2003 |
| WO | WO-2005111220 A2 | 11/2005 |
| WO | WO-2006096815 A2 | 9/2006 |
| WO | WO-2007019646 A1 | 2/2007 |
| WO | WO-2008021140 A2 | 2/2008 |
| WO | WO-2009000552 A2 | 12/2008 |
| WO | WO-2009043936 A1 | 4/2009 |
| WO | WO-2009130208 A1 | 10/2009 |
| WO | WO-2009134681 A2 | 11/2009 |
| WO | WO-2010124180 A1 | 10/2010 |
| WO | WO-2010/129021 A1 | 11/2010 |
| WO | WO-2011012724 A1 | 2/2011 |
| WO | WO-2011038187 A1 | 3/2011 |
| WO | WO-2014064277 A1 | 5/2014 |
| WO | WO-2014089212 A1 | 6/2014 |
| WO | WO-2014193716 A2 | 12/2014 |
| WO | WO-2015061491 A1 | 4/2015 |
| WO | WO-2015143177 A1 | 9/2015 |
| WO | WO-2015164723 A1 | 10/2015 |
| WO | WO-2016049230 A1 | 3/2016 |
| WO | WO-2016097218 A1 | 6/2016 |
| WO | WO-2016097219 A1 | 6/2016 |
| WO | WO-2016100575 A1 | 6/2016 |
| WO | WO-2016144757 A1 | 9/2016 |
| WO | WO-2017015154 A1 | 1/2017 |
| WO | WO-2017100551 A1 | 6/2017 |
| WO | WO-2018046737 A1 | 3/2018 |
| WO | WO-2018126112 A1 | 7/2018 |
| WO | WO-2018126116 A1 | 7/2018 |
| WO | WO-2018129586 A1 | 7/2018 |
| WO | WO-2019010091 A1 | 1/2019 |

OTHER PUBLICATIONS

Vercauteren et al, Superior In vivo Transduction of Human Hepatocytes Using Engineered AAV3 Capsid, Molecular Therapy vol. 24 No. Jun. 6, 2016, pp. 1042-1049.*

Pipe et al, Clinical Considerations for Capsid Choice in the Development of Liver-Targeted AAV-Based Gene Transfer, Molecular Therapy: Methods & Clinical Development vol. Dec. 15, 2019, pp. 170-178.*

Ahmed et al, Sustained Correction of a Murine Model of Phenylketonuria following a Single Intravenous Administration of

(56) References Cited

OTHER PUBLICATIONS

AAVHSC15-PAH, Molecular Therapy: Methods & Clinical Development vol. Jun. 17, 2020, pp. 568-580.*

De Sabbata et al., "Development of a novel AAV-based gene therapy in combination with tolerogenic nanoparticles for sustained treatment of ornithine transcarbamylase deficiency," Changing the Face of Modern Medicine: Stem Cell and Gene Therapy. Dec. 13, 2018;29(12):P343.

Grisch-Chan et al., "Low-Dose Gene Therapy for Murine PKU Using Episomal Naked DNA Vectors Expressing PAH from Its Endogenous Liver Promoter," Mol Ther Nucleic Acids. Jun. 16, 2017;7:339-349.

Hacein-Bey-Abina et al., "Insertional oncogenesis in 4 patients after retrovirus-mediated gene therapy of SCID-X1," J Clin Invest. 2008; 118(9):3132-42.

"*Homo sapiens* phenylalanine hydroxylase (PAH) mRNA, complete cds," GenBank U49897.1. Accessed Oct. 28, 2022.

Kramer et al., "In vitro and in vivo comparative study of chimeric liver-specific promoters," Mol Therapy. 2003; 7:375-85.

Lu et al., "A mini-intronic plasmid (MIP): a novel robust transgene expression vector in vivo and in vitro," Mol Ther. 2013;21(5): 954-63.

Lu et al., "A 5' Noncoding Exon Containing Engineered Intron Enhances Transgene Expression from Recombinant AAV Vectors in vivo," Hum Gene Ther. 2017;28(1): 125-34.

NCBI Reference Sequence: NG_008690.1.

Savy et al., "Impact of Inverted Terminal Repeat Integrity on rAAV8 Production Using the Baculovirus/Sf9 Cells System," Human Gene Therapy Methods. 2017;28(5):277-89.

Sibley et al., "Lessons from non-canonical splicing," Nat Rev Gen. 2016; 17:407-21.

Thöny, "Long-term correction of murine phenylketonuria by viral gene transfer: liver versus muscle," J Inherit Metab Dis. Dec. 2010;33(6):677-80.

Yagi et al., "Complete restoration of phenylalanine oxidation in phenylketonuria mouse by a self-complementary adeno-associated virus vector," J Gene Med. 2011; 13:114-22.

* cited by examiner

Long-Term Efficacy
Males, 2.6e13 vg/kg (N=4 per group)

Long-Term Efficacy
Females, 6e13 vg/kg (N=4 per group)

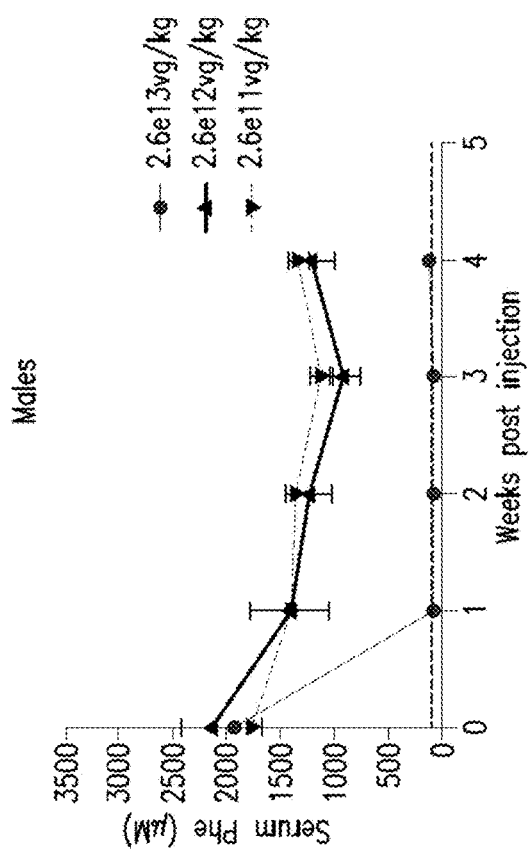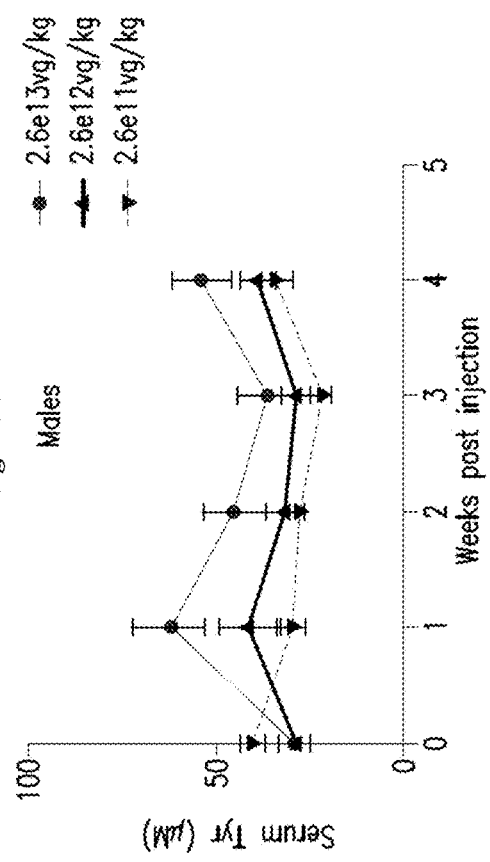
Figure 3A
Figure 3B

SEQUENCE LISTING

<160> NUMBER OF SEQ ID NOS: 23

<210> SEQ ID NO 1
<211> LENGTH: 1359
<212> TYPE: DNA
<213> ORGANISM: Artificial Sequence
<220> FEATURE:
<223> OTHER INFORMATION: Silently altered PAH coding sequence

<400> SEQUENCE: 1

```
atgtccaccg ctgtgctgga gaaccctggg ctggggagga aactgtcaga cttcgggcag      60
gagacttcat acattgagga taactgtaac cagaatggcg ccatctctct gatcttcagc     120
ctgaaggagg aagtgggcgc cctggcaaag gtgctgcgcc tgtttgagga gaacgacgtg     180
aatctgaccc catcgagtc ccggccttct agactgaaga aggacgagta cgagttcttt     240
acccacctgg ataagcggtc cctgccagcc ctgacaaaca tcatcaagat cctgaggcac     300
gacatcggag caaccgtgca cgagctgtct cgggacaaga gaaggatac cgtgccctgg     360
ttccctcgga caatccagga gctggataga tttgccaacc agatcctgtc ttacggagca     420
gagctggaca cagatcaccc tggcttcaag gacccagtgt atcgggcccg agaaaagcag     480
tttgccgata tcgcctacaa ttataggcac ggacagccaa tccctcgcgt ggagtatatg     540
gaggaggaga agaagacctg ggcacagtg ttcaagaccc tgaagagcct gtacaagaca     600
cacgcctgct acgagtataa ccacatcttc ccctgctgg agaagtattg tggcttt cac     660
gaggacaata tccctcagct ggaggacgtg agccagttcc tgcagacctg cacaggcttt     720
aggctgaggc cagtggcagg actgctgagc tcccgggact tcctgggagg actggccttc     780
agagtgtttc actgcaccca gtacatcagg cacggctcca agccaatgta tacaccagag     840
cccgacatct gtcacgagct gctgggccac gtgcccctgt ttagcgatag atccttcgcc     900
cagttttccc aggagatcgg actggcatct ctggagcac ctgacgagta catcgagaag     960
ctggccacca tctattggtt cacagtggag tttggcctgt gcaagcaggg cgatagcatc    1020
aaggcctacg agcaggact gctgtctagc ttcggcgagc tgcagtattg tctgtccgag    1080
aagccaaagc tgctgcccct ggagctggag aagaccgcca tccagaacta caccgtgaca    1140
gagttccagc cctgtactaa tgtggccgag tcttttaacg atgccaagga gaaggtgaga    1200
aatttcgccg ccacaatccc taggcccttc agcgtgcggt acgaccctta tacccagagg    1260
atcgaggtgc tggataatac acagcagctg aagatcctgg ctgactcaat caatagcgaa    1320
atcggaatcc tgtgctccgc cctgcagaaa atcaaatga                           1359
```

<210> SEQ ID NO 2
<211> LENGTH: 192
<212> TYPE: DNA
<213> ORGANISM: Homo sapiens

<400> SEQUENCE: 2

```
ccctaaaatg ggcaaacatt gcaagcagca aacagcaaac acacagccct ccctgcctgc      60
tgaccttgga gctggggcag aggtcagaga cctctctggg cccatgccac ctccaacatc     120
cactcgaccc cttggaattt cggtggagag gagcagaggt tgtcctggcg tggtttaggt     180
agtgtgagag gg                                                          192
```

<210> SEQ ID NO 3
<211> LENGTH: 205
<212> TYPE: DNA
<213> ORGANISM: Homo sapiens

<400> SEQUENCE: 3

```
aatgactcct ttcggtaagt gcagtggaag ctgtacactg cccaggcaaa gcgtccggc      60 agcgtaggcg ggcgactcag atcccagcca gtggacttag ccctgtttg ctcctccgat     120 aactggggtg accttggtta atattcacca gcagcctccc ccgttgcccc tctggatcca    180
ctgcttaaat acggacgagg acagg                                          205
```

<210> SEQ ID NO 4
<211> LENGTH: 93
<212> TYPE: DNA
<213> ORGANISM: Simian virus 40

<400> SEQUENCE: 4

```
ctctaaggta aatataaaat ttttaagtgt ataatgtgtt aaactactga ttctaattgt     60
ttctctcttt tagattccaa cctttggaac tga                                  93
```

<210> SEQ ID NO 5
<211> LENGTH: 398
<212> TYPE: DNA
<213> ORGANISM: Artificial Sequence
<220> FEATURE:
<223> OTHER INFORMATION: pHMI-hPAH-TC-025 transcriptional regulatory
      region

<400> SEQUENCE: 5

```
ccctaaaatg gcaaacatt gcaagcagca aacagcaaac acacagccct cctgcctgc       60 tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
aaagcgtccg gcagcgtag gcgggcgact cagatcccag ccagtggact tagcccctgt    300
ttgctcctcc gataactggg gtgaccttgg ttaatattca ccagcagcct cccccgttgc    360
ccctctggat ccactgctta aatacggacg aggacagg                            398
```

<210> SEQ ID NO 6
<211> LENGTH: 133
<212> TYPE: DNA
<213> ORGANISM: Simian virus 40

<400> SEQUENCE: 6

```
tgctttattt gtgaaatttg tgatgctatt gctttatttg taaccattat aagctgcaat    60
aaacaagtta acaacaacaa ttgcattcat tttatgtttc aggttcaggg ggaggtgtgg    120
gaggtttttt aaa                                                      133
```

<210> SEQ ID NO 7
<211> LENGTH: 2042
<212> TYPE: DNA
<213> ORGANISM: Artificial Sequence
<220> FEATURE:
<223> OTHER INFORMATION: pHMI-hPAH-TC-025 transfer genome

<400> SEQUENCE: 7

```
ccctaaaatg gcaaacatt gcaagcagca aacagcaaac acacagccct cctgcctgc       60 tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
```

```
aaagcgtccg ggcagcgtag gcgggcgact cagatcccag ccagtggact tagccctgt      300 ttgctcctcc gataactggg gtgaccttgg ttaatattca ccagcagcct ccccgttgc      360 ccctctggat ccactgctta aatacggacg aggacagggc cctgtctcct cagcttcagg      420
caccaccact gacctgggac agtgaatcct ctaaggtaaa tataaaattt ttaagtgtat      480
aatgtgttaa actactgatt ctaattgttt ctctctttta gattccaacc tttggaactg      540
accgccacca tgtccaccgc tgtgctggag aaccctgggc tggggaggaa actgtcagac      600
ttcgggcagg agacttcata cattgaggat aactgtaacc agaatggcgc catctctctg      660
atcttcagcc tgaaggagga gtgggcgcc ctggcaaagg tgctgcgcct gtttgaggag       720
aacgacgtga atctgaccca tcgagtcc cggccttcta gactgaagaa ggacgagtac       780
gagttcttta cccacctgga taagcggtcc ctgccagccc tgacaaacat catcaagatc      840
ctgaggcacg acatcggagc aaccgtgcac gagctgtctc gggacaagaa gaaggatacc      900 gtgcctggt tccctcggac aatccaggag ctggatagat ttgccaacca gatcctgtct      960
tacggagcag agctggacgc agatcaccct ggcttcaagg acccagtgta tcgggcccgg     1020
agaaagcagt ttgccgatat cgcctacaat tataggcacg acagccaat ccctcgcgtg     1080 gagtatatgg aggaggagaa gaagacctgg ggcacagtgt tcaagaccct gaagagcctg     1140
tacaagacac acgcctgcta cgagtataac cacatcttcc ccctgctgga gaagtattgt     1200
ggctttcacg aggacaatat ccctcagctg gaggacgtga ccagttcct gcagacctgc     1260 acaggcttta ggctgaggcc agtggcagga ctgctgagct cccgggactt cctgggagga     1320
ctggccttca gagtgtttca ctgcacccag tacatcaggc acggctccaa gccaatgtat     1380
acaccagagc ccgacatctg tcacgagctg ctgggccacg tgcccctgtt tagcgataga     1440
tccttcgccc agtttttccca ggagatcgga ctggcatctc tgggagcacc tgacgagtac     1500
atcgagaagc tggccaccat ctattggttc acagtggagt ttggcctgtg caagcagggc     1560
gatagcatca aggcctacgg agcaggactg ctgtctagct tcggcgagct gcagtattgt     1620
ctgtccgaga agccaaagct gctgcccctg gagctggaga agaccgccat ccagaactac     1680
accgtgacag agttccagcc cctgtactat gtggccgagt cttttaacga tgccaaggag     1740
aaggtgagaa atttcgccgc cacaatccct aggcccttca gcgtgcggta cgacccttat     1800
acccagagga tcgaggtgct ggataataca cagcagctga gatcctggc tgactcaatc     1860 aatagcgaaa tcggaatcct gtgctccgcc ctgcagaaaa tcaaatgaat gctttatttg     1920
tgaaatttgt gatgctattg ctttatttgt aaccattata agctgcaata aacaagttaa     1980
caacaacaat tgcattcatt ttatgtttca ggttcagggg gaggtgtggg aggttttta      2040 aa                                                                    2042
```

<210> SEQ ID NO 8
<211> LENGTH: 106
<212> TYPE: DNA
<213> ORGANISM: Artificial Sequence
<220> FEATURE:
<223> OTHER INFORMATION: truncated AAV2 5'ITR

<400> SEQUENCE: 8

```
ctgcgcgctc gctcgctcac tgaggccgcc cgggcaaagc ccgggcgtcg gcgacctt       60 ggtcgcccgg cctcagtgag cgagcgagcg cgcagagagg gagtgg                    106
```

<210> SEQ ID NO 9

```
<211> LENGTH: 143
<212> TYPE: DNA
<213> ORGANISM: Artificial Sequence
<220> FEATURE:
<223> OTHER INFORMATION: modified AAV2 3'ITR

<400> SEQUENCE: 9
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc   120 gagcgcgcag agagggagtg gcc                                          143

<210> SEQ ID NO 10
<211> LENGTH: 2356
<212> TYPE: DNA
<213> ORGANISM: Artificial Sequence
<220> FEATURE:
<223> OTHER INFORMATION: pHMI-hPAH-TC-025 transfer genome (from 5' ITR
      to 3' ITR)

<400> SEQUENCE: 10
ctgcgcgctc gctcgctcac tgaggccgcc cgggcaaagc ccgggcgtcg gcgaccttt     60 ggtcgcccgg cctcagtgag cgagcgagcg cgcagagagg gagtggaatt cacgcgtgga  120
tctgaattca attcacgcgt ggtacctccc taaaatgggc aaacattgca agcagcaaac  180
agcaaacaca cagccctccc tgcctgctga ccttggagct ggggcagagg tcagagacct  240
ctctgggccc atgccacctc caacatccac tcgacccctt ggaatttcgg tggagaggag  300
cagaggttgt cctggcgtgg tttaggtagt gtgagagggg aatgactcct ttcggtaagt  360
gcagtggaag ctgtacactg cccaggcaaa gcgtccgggc agcgtaggcg ggcgactcag  420
atcccagcca gtggacttag cccctgtttg ctcctccgat aactgggtg accttggtta  480 atattcacca gcagcctccc ccgttgcccc tctggatcca ctgcttaaat acggacgagg  540
acagggccct gtctcctcag cttcaggcac caccactgac ctgggacagt gaatcctcta  600
aggtaaatat aaaattttta agtgtataat gtgttaaact actgattcta attgtttctc  660
tcttttagat tccaaccttt ggaactgacc gccaccatgt ccaccgctgt gctggagaac  720
cctgggctgg ggaggaaact gtcagacttc ggcaggaga cttcatacat tgaggataac  780
tgtaaccaga atggcgccat ctctctgatc ttcagcctga aggaggaagt gggcgccctg  840
gcaaaggtgc tgcgcctgtt tgaggagaac gacgtgaatc tgacccacat cgagtccgg  900 ccttctagac tgaagaagga cgagtacgag ttctttaccc acctggataa gcggtccctg  960
ccagccctga caaacatcat caagatcctg aggcacgaca tcggagcaac cgtgcacgag 1020
ctgtctcggg acaagaagaa ggataccgtg ccctggttcc ctcggacaat ccaggagctg 1080
gatagatttg ccaaccagat cctgtcttac ggagcagagc tggacgcaga tcaccctggc 1140
ttcaaggacc cagtgtatcg ggcccggaga aagcagtttg ccgatatcgc ctacaattat 1200
aggcacggac agccaatccc tcgcgtggag tatatggagg aggagaagaa gacctggggc 1260
acagtgttca agaccctgaa gagcctgtac aagacacacg cctgctacga gtataaccac 1320
atcttccccc tgctggagaa gtattgtggc tttcacgagg acaatatccc tcagctggag 1380
gacgtgagcc agttcctgca gacctgcaca ggctttaggc tgaggccagt ggcaggactg 1440
ctgagctccc gggacttcct gggaggactg gccttcagag tgtttcactg cacccagtac 1500
atcaggcacg gctccaagcc aatgtataca ccagagcccg acatctgtca cgagctgctg 1560
ggccacgtgc cctgtttag cgatagatcc ttcgcccagt tttcccagga gatcggactg 1620
```

```
gcatctctgg gagcacctga cgagtacatc gagaagctgg ccaccatcta ttggttcaca    1680
gtggagtttg gcctgtgcaa gcagggcgat agcatcaagg cctacggagc aggactgctg    1740
tctagcttcg gcgagctgca gtattgtctg tccgagaagc caaagctgct gcccctggag    1800
ctggagaaga ccgccatcca gaactacacc gtgacagagt ccagcccct gtactatgtg    1860 gccgagtctt ttaacgatgc caaggagaag gtgagaaatt cgccgccac aatccctagg    1920 cccttcagcg tgcggtacga cccttatacc cagaggatcg aggtgctgga ataatacacag   1980 cagctgaaga tcctggctga ctcaatcaat agcgaaatcg gaatcctgtg ctccgccctg    2040
cagaaaatca aatgaatgct ttatttgtga aatttgtgat gctattgctt tatttgtaac    2100
cattataagc tgcaataaac aagttaacaa caacaattgc attcatttta tgtttcaggt    2160
tcagggggag gtgtgggagg ttttttaaag catgctgggg agagatcgat ctgaggaacc    2220
cctagtgatg gagttggcca ctccctctct gcgcgctcgc tcgctcactg aggccgggcg    2280
accaaaggtc gcccgacgcc cgggctttgc ccgggcggcc tcagtgagcg agcgagcgcg    2340
cagagaggga gtggcc                                                    2356
```

<210> SEQ ID NO 11
<211> LENGTH: 736
<212> TYPE: PRT
<213> ORGANISM: Artificial Sequence
<220> FEATURE:
<223> OTHER INFORMATION: novel AAV isolate

<400> SEQUENCE: 11

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
```

```
                225                 230                 235                 240
            Thr Thr Ser Thr Arg Thr Trp Ala Leu Pro Thr Tyr Asn Asn His Leu
                            245                 250                 255
            Tyr Lys Gln Ile Ser Asn Ser Thr Ser Gly Ser Ser Asn Asp Asn
                            260                 265                 270
            Ala Tyr Phe Gly Tyr Ser Thr Pro Trp Gly Tyr Phe Asp Phe Asn Arg
                            275                 280                 285
            Phe His Cys His Phe Ser Pro Arg Asp Trp Gln Arg Leu Ile Asn Asn
                290                 295                 300
            Asn Trp Gly Phe Arg Pro Lys Arg Leu Asn Phe Lys Leu Phe Asn Ile
            305                 310                 315                 320
            Gln Val Lys Glu Val Thr Asp Asn Asn Gly Val Lys Thr Ile Ala Asn
                            325                 330                 335
            Asn Leu Thr Ser Thr Val Gln Val Phe Ala Asp Ser Asp Tyr Gln Leu
                            340                 345                 350
            Pro Tyr Val Leu Gly Ser Ala His Glu Gly Cys Leu Pro Pro Phe Pro
                            355                 360                 365
            Ala Asp Val Phe Met Ile Pro Gln Tyr Gly Tyr Leu Thr Leu Asn Asp
                370                 375                 380
            Gly Ser Gln Ala Val Gly Arg Ser Ser Phe Tyr Cys Leu Glu Tyr Phe
            385                 390                 395                 400
            Pro Ser Gln Met Leu Arg Thr Gly Asn Asn Phe Gln Phe Ser Tyr Glu
                            405                 410                 415
            Phe Glu Asn Val Pro Phe His Ser Ser Tyr Ala His Ser Gln Ser Leu
                            420                 425                 430
            Asp Arg Leu Met Asn Pro Leu Ile Asp Gln Tyr Leu Tyr Tyr Leu Ser
                            435                 440                 445
            Lys Thr Ile Asn Gly Ser Gly Gln Asn Gln Gln Thr Leu Lys Phe Ser
            450                 455                 460
            Val Ala Gly Pro Ser Asn Met Ala Val Gln Gly Arg Asn Tyr Ile Pro
            465                 470                 475                 480
            Gly Pro Ser Tyr Arg Gln Gln Arg Val Ser Thr Thr Val Thr Gln Asn
                            485                 490                 495
            Asn Asn Ser Glu Phe Ala Trp Pro Arg Ala Ser Ser Trp Ala Leu Asn
                            500                 505                 510
            Gly Arg Asn Ser Leu Met Asn Pro Gly Pro Ala Met Ala Ser His Lys
                            515                 520                 525
            Glu Gly Glu Asp Arg Phe Phe Pro Leu Ser Gly Ser Leu Ile Phe Gly
                530                 535                 540
            Lys Gln Gly Thr Gly Arg Asp Asn Val Asp Ala Asp Lys Val Met Ile
            545                 550                 555                 560
            Thr Asn Glu Glu Glu Ile Lys Thr Thr Asn Pro Val Ala Thr Glu Ser
                            565                 570                 575
            Tyr Gly Gln Val Ala Thr Asn His Gln Ser Ala Gln Ala Gln Ala Gln
                            580                 585                 590
            Thr Gly Trp Val Gln Asn Gln Gly Ile Leu Pro Gly Met Val Trp Gln
                            595                 600                 605
            Asp Arg Asp Val Tyr Leu Gln Gly Pro Ile Trp Ala Lys Ile Pro His
                610                 615                 620
            Thr Asp Gly Asn Phe His Pro Ser Pro Leu Met Gly Gly Phe Gly Met
            625                 630                 635                 640
            Lys His Pro Pro Pro Gln Ile Leu Ile Lys Asn Thr Pro Val Pro Ala
                            645                 650                 655
```

```
                    Asp Pro Thr Ala Phe Asn Lys Asp Lys Leu Asn Ser Phe Ile Thr
                            660                 665                 670

Gln Tyr Ser Thr Gly Gln Val Ser Val Glu Ile Glu Trp Glu Leu Gln
                        675                 680                 685

Lys Glu Asn Ser Lys Arg Trp Asn Pro Glu Ile Gln Tyr Thr Ser Asn
                        690                 695                 700

Tyr Tyr Lys Ser Asn Asn Val Glu Phe Ala Val Asn Thr Glu Gly Val
                    705                 710                 715                 720

Tyr Ser Glu Pro Arg Pro Ile Gly Thr Arg Tyr Leu Thr Arg Asn Leu
                                    725                 730                 735

<210> SEQ ID NO 12
<211> LENGTH: 1359
<212> TYPE: DNA
<213> ORGANISM: Homo sapiens

<400> SEQUENCE: 12
atgtccactg cggtcctgga aacccaggc ttgggcagga aactctctga ctttggacag      60
gaaacaagct atattgaaga caactgcaat caaaatggtg ccatatcact gatcttctca     120
ctcaaagaag aagttggtgc attggccaaa gtattgcgct tatttgagga gaatgatgta    180
aacctgaccc acattgaatc tagaccttct cgtttaaaga agatgagta tgaattttc     240 acccatttgg ataaacgtag cctgcctgct ctgacaaaca tcatcaagat cttgaggcat    300
gacattggtg ccactgtcca tgagctttca cgagataaga agaaagacac agtgccctgg    360
ttcccaagaa ccattcaaga ctggacagat tttgccaatc agattctcag ctatggagcg    420
gaactggatg ctgaccaccc tggttttaaa gatcctgtgt accgtgcaag acggaagcag    480
tttgctgaca ttgcctacaa ctaccgccat gggcagccca tccctcgagt ggaatacatg    540
gaggaagaaa agaaaacatg ggcacagtg ttcaagactc tgaagtcctt gtataaaacc    600
catgcttgct atgagtacaa tcacattttt ccacttcttg aaaagtactg tggcttccat    660
gaagataaca ttccccagct ggaagacgtt tctcaattcc tgcagacttg cactggtttc    720
cgcctccgac ctgtgctgg cctgcttttcc tctcgggatt tcttgggtgg cctggccttc    780
cgagtcttcc actgcacaca gtacatcaga catggatcca agcccatgta taccccgaa    840 cctgacatct gccatgagct gttgggacat gtgccctgt tttcagatcg cagctttgcc    900
cagttttccc aggaaattgg ccttgcctct ctgggtgcac ctgatgaata cattgaaaag   960
ctcgccacaa tttactggtt tactgtggag tttgggctct gcaaacaagg agactccata   1020
aaggcatatg gtgctgggct cctgtcatcc tttggtgaat tacagtactg cttatcagag   1080
aagccaaagc ttctcccct ggagctggag aagacagcca tccaaaatta cactgtcacg   1140
gagttccagc ccctgtatta cgtggcagag agttttaatg atgccaagga gaaagtaagg   1200
aactttgctg ccacaatacc tcggcccttc tcagttcgct acgacccata cacccaaagg   1260
attgaggtct ggacaatac ccagcagctt aagattttgg ctgattccat taacagtgaa   1320
attggaatcc tttgcagtgc cctccagaaa ataaagtaa                          1359

<210> SEQ ID NO 13
<211> LENGTH: 452
<212> TYPE: PRT
<213> ORGANISM: Homo sapiens

<400> SEQUENCE: 13

Met Ser Thr Ala Val Leu Glu Asn Pro Gly Leu Gly Arg Lys Leu Ser
```

```
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
            35                  40                  45

Ala Lys Val Leu Arg Leu Phe Glu Glu Asn Asp Val Asn Leu Thr His
 50                      55                  60

Ile Glu Ser Arg Pro Ser Arg Leu Lys Lys Asp Glu Tyr Glu Phe Phe
 65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
                100                 105                 110

Lys Lys Lys Asp Thr Val Pro Trp Phe Pro Arg Thr Ile Gln Glu Leu
                115                 120                 125

Asp Arg Phe Ala Asn Gln Ile Leu Ser Tyr Gly Ala Glu Leu Asp Ala
            130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Lys Lys Thr Trp Gly Thr Val Phe Lys
                180                 185                 190

Thr Leu Lys Ser Leu Tyr Lys Thr His Ala Cys Tyr Glu Tyr Asn His
                195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
                260                 265                 270

Ser Lys Pro Met Tyr Thr Pro Glu Pro Asp Ile Cys His Glu Leu Leu
                275                 280                 285

Gly His Val Pro Leu Phe Ser Asp Arg Ser Phe Ala Gln Phe Ser Gln
            290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
                355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
                420                 425                 430
```

Leu Ala Asp Ser Ile Asn Ser Glu Ile Gly Ile Leu Cys Ser Ala Leu
        435                 440                 445

Gln Lys Ile Lys
    450

<210> SEQ ID NO 14
<211> LENGTH: 592
<212> TYPE: DNA
<213> ORGANISM: Homo sapiens

<400> SEQUENCE: 14
gtaaatttta tggaatgtga atcataattc aattttttcaa catgcgttag gagggacatt      60
tcaaactctt ttttacccta gactttccta ccatcaccca gagtatccag ccaggagggg     120
aggggctaga gacaccagaa gtttagcagg gaggagggcg tagggattcg gggaatgaag     180
ggatgggatt cagactaggg ccaggaccca gggatggaga gaaagagatg agagtggttt     240
gggggcttgg tgacttagag aacagagctg caggctcaga ggcacacagg agtttctggg     300
ctcaccctgc ccccttccaa cccctcagtt cccatcctcc agcagctgtt tgtgtgctgc     360
ctctgaagtc cacactgaac aaacttcagc ctactcatgt ccctaaaatg ggcaaacatt     420
gcaagcagca aacagcaaac acacagccct ccctgcctgc tgaccttgga gctggggcag     480
aggtcagaga cctctctggg cccatgccac ctccaacatc cactcgaccc cttggaatTt     540
cggtggagag gagcagaggt tgtcctggcg tggtttaggt agtgtgagag gg             592

<210> SEQ ID NO 15
<211> LENGTH: 423
<212> TYPE: DNA
<213> ORGANISM: Homo sapiens

<400> SEQUENCE: 15
gctctaaccc actctgatct cccagggcgg cagtaagtct tcagcatcag gcattttggg      60
gtgactcagt aaatggtaga tcttgctacc agtggaacag ccactaagga ttctgcagtg     120
agagcagagg gccagctaag tggtactctc ccagagactg tctgactcac gccacccct     180 ccaccttgga cacaggacgc tgtggtttct gagccaggta caatgactcc tttcggtaag     240
tgcagtggaa gctgtacact gcccaggcaa agcgtccggg cagcgtaggc gggcgactca     300
gatcccagcc agtggactta gccctgtttt gctcctccga taactggggt gaccttggtt     360
aatattcacc agcagcctcc cccgttgccc ctctggatcc actgcttaaa tacggacgag     420
gac                                                                    423

<210> SEQ ID NO 16
<211> LENGTH: 145
<212> TYPE: DNA
<213> ORGANISM: Artificial Sequence
<220> FEATURE:
<223> OTHER INFORMATION: AAV2 5' ITR

<400> SEQUENCE: 16
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcct                                             145

<210> SEQ ID NO 17
<211> LENGTH: 145
<212> TYPE: DNA

<213> ORGANISM: Artificial Sequence
<220> FEATURE:
<223> OTHER INFORMATION: AAV2 3' ITR

<400> SEQUENCE: 17

```
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag agagggagtg gccaa                                         145
```

<210> SEQ ID NO 18
<211> LENGTH: 167
<212> TYPE: DNA
<213> ORGANISM: Artificial Sequence
<220> FEATURE:
<223> OTHER INFORMATION: AAV5 5' ITR

<400> SEQUENCE: 18

```
ctctccccc tgtcgcgttc gctcgctcgc tggctcgttt ggggggggtgg cagctcaaag    60 agctgccaga cgacggccct ctggccgtcg ccccccaaa cgagccagcg agcgagcgaa    120
cgcgacaggg gggagagtgc cacactctca agcaaggggg ttttgta                 167
```

<210> SEQ ID NO 19
<211> LENGTH: 167
<212> TYPE: DNA
<213> ORGANISM: Artificial Sequence
<220> FEATURE:
<223> OTHER INFORMATION: AAV5 3' ITR

<400> SEQUENCE: 19

```
tacaaaacct ccttgcttga gagtgtggca ctctccccc tgtcgcgttc gctcgctcgc    60
tggctcgttt ggggggggtgg cagctcaaag agctgccaga cgacggccct ctggccgtcg   120 ccccccaaa cgagccagcg agcgagcgaa cgcgacaggg gggagag                  167
```

<210> SEQ ID NO 20
<211> LENGTH: 37
<212> TYPE: DNA
<213> ORGANISM: Artificial Sequence
<220> FEATURE:
<223> OTHER INFORMATION: 37 bp additional 3' ITR sequence from wtAAV2

<400> SEQUENCE: 20

```
gtagataagt agcatggcgg gttaatcatt aactaca                             37
```

<210> SEQ ID NO 21
<211> LENGTH: 180
<212> TYPE: DNA
<213> ORGANISM: Artificial Sequence
<220> FEATURE:
<223> OTHER INFORMATION: 3'ITR with additional 37 bp sequence

<400> SEQUENCE: 21

```
gtagataagt agcatggcgg gttaatcatt aactacaagg aaccccctagt gatggagttg    60 gccactccct ctctgcgcgc tcgctcgctc actgaggccg ggcgaccaaa ggtcgcccga   120
cgcccgggct tgcccgggc ggcctcagtg agcgagcgag cgcgcagaga gggagtggcc    180
```

<210> SEQ ID NO 22
<211> LENGTH: 621
<212> TYPE: PRT
<213> ORGANISM: Artificial Sequence
<220> FEATURE:
<223> OTHER INFORMATION: AAV2 Rep

<400> SEQUENCE: 22

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
```

|    |     |     |     |     | 405 |     |     |     |     | 410 |     |     |     |     | 415 |     |     |
|----|-----|-----|-----|-----|-----|-----|-----|-----|-----|-----|-----|-----|-----|-----|-----|-----|-----|

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
610                 615                 620

<210> SEQ ID NO 23
<211> LENGTH: 6020
<212> TYPE: DNA
<213> ORGANISM: Artificial Sequence
<220> FEATURE:
<223> OTHER INFORMATION: pHMI-hPAH-TC-025 full sequence

<400> SEQUENCE: 23

| aacgccagca acgcggcctt tttacggttc ctggcctttt gctggccttt tgctcacatg | 60 |
| ttctttcctg cgttatcccc tgattctgtg gataaccgta ttaccgcctt tgagtgagct | 120 |
| gataccgctc gccgcagccg aacgaccgag cgcagcgagt cagtgagcga ggaagcggaa | 180 |
| gagcgcccaa tacgcaaacc gcctctcccc gcgcgttggc cgattcatta atgcagcagc | 240 |
| tggcgtaata gcgaagaggc ccgcaccgat cgcccttccc aacagttgcg cagcctgaat | 300 |
| ggcgaatgga attccagacg attgagcgtc aaaatgtagg tatttccatg agcgtttttc | 360 |
| ctgttgcaat ggctggcggt aatattgttc tggatattac cagcaaggcc gatagtttga | 420 |
| gttcttctac tcaggcaagt gatgttatta ctaatcaaag aagtattgcg acaacggtta | 480 |
| atttgcgtga tggacagact cttttactcg gtggcctcac tgattataaa aacacttctc | 540 |
| aggattctgg cgtaccgttc ctgtctaaaa tccctttaat cggcctcctg tttagctccc | 600 |
| gctctgattc taacgaggaa agcacgttat acgtgctcgt caaagcaacc atagtacgcg | 660 |
| ccctgtagcg gcgcattaag cgcggcgggt gtggtggtta cgcgcagcgt gaccgctaca | 720 |
| cttgccagcg ccctagcgcc cgctcctttt gctttcttcc cttcctttct cgccacgttc | 780 |
| gccggctttc cccgtcaagc tctaaatcgg ggctcccctt tagggttccg atttagtgct | 840 |

```
ttacggcacc tcgacccaa aaaacttgat tagggtgatg gttcacgtag tgggccatcg      900
ccctgataga cggttttcg ccctttgacg ttggagtcca cgttctttaa tagtggactc      960
ttgttccaaa ctggaacaac actcaaccct atctcggtct attcttttga tttataaggg    1020
attttgccga tttcggccta ttggttaaaa aatgagctga tttaacaaaa atttaacgcg    1080
aattttaaca aaatattaac gcttacaatt taaatatttg cttatacaat cttcctgttt    1140
ttggggcttt tctgattatc aaccggggta catatgattg acatgctagt tttacgatta    1200
ccgttcatcg ccctgcgcgc tcgctcgctc actgaggccg cccgggcaaa gcccgggcgt    1260
cgggcgacct ttggtcgccc ggcctcagtg agcgagcgag cgcgcagaga gggagtggaa    1320
ttcacgcgtg gatctgaatt caattcacgc gtggtacctc cctaaaatgg gcaaacattg    1380
caagcagcaa acagcaaaca cacagccctc cctgcctgct gaccttggag ctggggcaga    1440
ggtcagagac ctctctgggc ccatgccacc tccaacatcc actcgacccc ttggaatttc    1500
ggtggagagg agcagaggtt gtcctggcgt ggtttaggta gtgtgagagg ggaatgactc    1560
ctttcggtaa gtgcagtgga agctgtacac tgcccaggca aagcgtccgg gcagcgtagg    1620
cgggcgactc agatcccagc cagtggactt agcccctgtt tgctcctccg ataactgggg    1680
tgaccttggt taatattcac cagcagcctc ccccgttgcc cctctggatc cactgcttaa    1740
atacggacga ggacagggcc ctgtctcctc agcttcaggc accaccactg acctgggaca    1800
gtgaatcctc taaggtaaat ataaaatttt taagtgtata atgtgttaaa ctactgattc    1860
taattgtttc tctcttttag attccaacct ttggaactga ccgccaccat gtccaccgct    1920
gtgctggaga accctgggct ggggaggaaa ctgtcagact tcgggcagga gacttcatac    1980
attgaggata actgtaacca gaatggcgcc atctctctga tcttcagcct gaaggaggaa    2040
gtgggcgccc tggcaaaggt gctgcgcctg tttgaggaga cgacgtgaa tctgacccac    2100
atcgagtccc ggccttctag actgaagaag gacgagtacg agttctttac ccacctggat    2160
aagcggtccc tgccagccct gacaaacatc atcaagatcc tgaggcacga catcggagca    2220
accgtgcacg agctgtctcg ggacaagaag aaggataccg tgccctggtt ccctcggaca    2280
atccaggagc tggatagatt tgccaaccag atcctgtctt acggagcaga gctggacgca    2340
gatcaccctg gcttcaagga cccagtgtat cgggcccgga aaagcagtt tgccgatatc    2400
gcctacaatt ataggcacgg acagccaatc cctcgcgtgg agtatatgga ggaggagaag    2460
aagacctggg gcacagtgtt caagaccctg aagagcctgt acaagacaca cgcctgctac    2520
gagtataacc acatcttccc cctgctggag aagtattgtg gctttcacga ggacaatatc    2580
cctcagctgg aggacgtgag ccagttcctg cagacctgca caggctttag gctgaggcca    2640
gtggcaggac tgctgagctc ccgggacttc ctggggagac tggccttcag agtgtttcac    2700
tgcacccagt acatcaggca cggctccaag ccaatgtata caccagagcc cgacatctgt    2760
cacgagctgc tgggccacgt gcccctgttt agcgatagat ccttcgccca gttttccccag   2820
gagatcggac tggcatctct gggagcacct gacgagtaca tcgagaagct ggccaccatc    2880
tattggttca cagtggagtt tggcctgtgc aagcagggcg atagcatcaa ggcctacgga    2940
gcaggactgc tgtctagctt cggcgagctg cagtattgtc tgtccgagaa gccaaagctg    3000
ctgcccctgg agctggagaa gaccgccatc cagaactaca ccgtgacaga gttccagccc    3060
ctgtactatg tggccgagtc tttttaacgat gccaaggaga aggtgagaaa tttcgccgcc    3120
acaatcccta ggcccttcag cgtgcggtac gaccctata cccagaggat cgaggtgctg    3180
gataatacac agcagctgaa gatcctggct gactcaatca atagcgaaat cggaatcctg    3240
```

```
tgctccgccc tgcagaaaat caaatgaatg ctttatttgt gaaatttgtg atgctattgc    3300
tttatttgta accattataa gctgcaataa acaagttaac aacaacaatt gcattcattt    3360
tatgtttcag gttcagggggg aggtgtggga ggttttttaa agcatgctgg ggagagatcg   3420
atctgaggaa ccctagtga tggagttggc cactccctct ctgcgcgctc gctcgctcac    3480
tgaggccggg cgaccaaagg tcgcccgacg cccgggcttt gcccgggcgg cctcagtgag    3540
cgagcgagcg cgcagagagg gagtggcccc cccccccccc cccccggcg attctcttgt     3600
ttgctccaga ctctcaggca atgacctgat agcctttgta gagacctctc aaaaatagct    3660
accctctccg gcatgaattt atcagctaga acggttgaat atcatattga tggtgatttg    3720
actgtctccg gccttttctca cccgtttgaa tctttaccta cacattactc aggcattgca   3780
tttaaaatat atgagggttc taaaaatttt tatccttgcg ttgaaataaa ggcttctccc    3840
gcaaaagtat tacagggtca taatgttttt ggtacaaccg atttagcttt atgctctgag   3900
gctttattgc ttaattttgc taattctttg ccttgcctgt atgatttatt ggatgttgga    3960
atcgcctgat gcggtatttt ctccttacgc atctgtgcgg tatttcacac cgcatatggt    4020
gcactctcag tacaatctgc tctgatgccg catagttaag ccagccccga cacccgccaa    4080
cacccgctga cgcgccctga cgggcttgtc tgctcccggc atccgcttac agacaagctg    4140
tgaccgtctc cgggagctgc atgtgtcaga ggttttcacc gtcatcaccg aaacgcgcga    4200
gacgaaaggg cctcgtgata cgcctatttt tataggttaa tgtcatgata ataatggttt    4260
cttagacgtc aggtggcact tttcggggaa atgtgcgcgg aaccctatt tgtttatttt     4320
tctaaataca ttcaaatatg tatccgctca tgagacaata accctgataa atgcttcaat    4380
aatattgaaa aaggaagagt atgagtattc aacatttccg tgtcgccctt attccctttt    4440
ttgcggcatt ttgccttcct gtttttgctc acccagaaac gctggtgaaa gtaaaagatg    4500
ctgaagatca gttgggtgca cgagtgggtt acatcgaact ggatctcaac agcggtaaga    4560
tccttgagag ttttcgcccc gaagaacgtt ttccaatgat gagcactttt aaagttctgc    4620
tatgtggcgc ggtattatcc cgtattgacg ccgggcaaga gcaactcggt cgccgcatac    4680
actattctca gaatgacttg gttgagtact caccagtcac agaaaagcat cttacggatg    4740
gcatgacagt aagagaatta tgcagtgctg ccataaccat gagtgataac actgcggcca    4800
acttacttct gacaacgatc ggaggaccga aggagctaac cgcttttttg cacaacatgg    4860
gggatcatgt aactcgcctt gatcgttggg aaccggagct gaatgaagcc ataccaaacg    4920
acgagcgtga ccaccgatg cctgtagcaa tggcaacaac gttgcgcaaa ctattaactg     4980
gcgaactact tactctagct tcccggcaac aattaataga ctggatggag gcggataaag    5040
ttgcaggacc acttctgcgc tcggcccttc cggctggctg gtttattgct gataaatctg    5100
gagccggtga gcgtgggtct cgcggtatca ttgcagcact ggggccagat ggtaagccct    5160
cccgtatcgt agttatctac acgacgggga gtcaggcaac tatggatgaa cgaaatagac    5220
agatcgctga gataggtgcc tcactgatta agcattggta actgtcagac caagtttact    5280
catatatact ttagattgat ttaaaacttc attttttaatt taaaaggatc taggtgaaga    5340
tcctttttga taatctcatg accaaaatcc cttaacgtga gttttcgttc cactgagcgt    5400
cagaccccgt agaaaagatc aaaggatctt cttgagatcc ttttttttctg cgcgtaatct    5460
gctgcttgca acaaaaaaa ccaccgctac cagcggtggt ttgtttgccg gatcaagagc    5520
taccaactct ttttccgaag gtaactggct tcagcagagc gcagatacca atactgtcc     5580
```

```
ttctagtgta gccgtagtta ggccaccact tcaagaactc tgtagcaccg cctacatacc    5640
tcgctctgct aatcctgtta ccagtggctg ctgccagtgg cgataagtcg tgtcttaccg    5700
ggttggactc aagacgatag ttaccggata aggcgcagcg gtcgggctga acggggggtt    5760
cgtgcacaca gcccagcttg gagcgaacga cctacaccga actgagatac ctacagcgtg    5820
agctatgaga aagcgccacg cttcccgaag ggagaaaggc ggacaggtat ccggtaagcg    5880
gcagggtcgg aacaggagag cgcacgaggg agcttccagg gggaaacgcc tggtatcttt    5940
atagtcctgt cgggtttcgc cacctctgac ttgagcgtcg atttttgtga tgctcgtcag    6000
gggggcggag cctatggaaa                                                6020
```

METHODS OF TREATING PHENYLKETONURIA

CROSS-REFERENCE TO RELATED APPLICATIONS

This application claims the benefit of U.S. Provisional Application No. 62/960,498, filed Jan. 13, 2020, and 63/110,251, filed Nov. 5, 2020, each of which are hereby incorporated by reference in their entirety.

REFERENCE TO SEQUENCE LISTING SUBMITTED ELECTRONICALLY

The content of the electronically submitted sequence listing in ASCII text file (Name: "713281_HMW-039_ST25.txt"; Size: 39,981 bytes; and Date of Creation: Jan. 13, 2021) is incorporated herein by reference in its entirety.

BACKGROUND

Phenylketonuria (PKU) is an autosomal recessive genetic disorder where the majority of cases are caused by mutations in the phenylalanine hydroxylase (PAH) gene. Mutations in the PAH gene result in a reduction or loss of PAH activity, an enzyme expressed in hepatocytes that catalyzes the hydroxylation of L-phenylalanine (Phe) to L-tyrosine (Tyr) upon multimerization. Reduction or loss of PAH activity leads to phenylalanine accumulation and its conversion into phenylpyruvate (also known as phenylketone). If left untreated, PAH deficiency results in progressive, irreversible neurological impairment during infancy and early childhood. The inability to achieve normal concentrations of Phe results in neurological as well as metabolic problems.

Currently, there is no cure for PKU. The standard of care is diet management by minimizing foods that contain high amounts of phenylalanine. Dietary management from birth with a low phenylalanine formula largely prevents the development of the intellectual disability of the disorder. However, even on a low-phenylalanine diet, children still suffer from growth retardation, and adults often have osteoporosis and vitamin deficiencies. Moreover, adherence to life-long dietary treatment is difficult, particularly once children reach school age.

New treatment strategies have recently emerged, including large neutral amino acid (LNAA) supplementation, cofactor tetrahydrobiopterin therapy, enzyme replacement therapy, and genetically modified probiotic therapy. However, these strategies suffer from shortcomings. The LNAA supplementation is suitable only for adults not adhering to a low Phe diet. The cofactor tetrahydrobiopterin can only be used in some mild forms of PKU. Enzyme replacement by administration of a substitute for PAH, e.g., phenylalanine ammonia-lyase (PAL), can lead to immune responses that reduce the efficacy and/or cause side effects. As to genetically modified probiotic therapy, the pathogenicity of PAL-expressing *E. coli* has been a concern.

Gene therapy provides a unique opportunity to cure PKU. Retroviral vectors, including lentiviral vectors, are capable of integrating nucleic acids into host cell genomes, raising safety concerns due to their non-targeted insertion into the genome. For example, there is a risk of the vector disrupting a tumor suppressor gene or activating an oncogene, thereby causing a malignancy. Indeed, in a clinical trial for treating X-linked severe combined immunodeficiency (SCID) by transducing CD34$^+$ bone marrow precursors with a gammaretroviral vector, four out of ten patients developed leukemia (Hacein-Bey-Abina et al., J Clin Invest. (2008) 118(9):3132-42). Non-integrating vectors, on the other hand, often suffer insufficient expression level or inadequate duration of expression in vivo.

Accordingly, there is a need in the art for improved gene therapy compositions and methods that can efficiently and safely restore PAH gene function in PKU patients.

SUMMARY

Provided herein are methods of treating a subject having a disease or disorder associated with a PAH gene mutation. The methods generally comprise administering to the subject a therapeutically effective dose of a recombinant adeno-associated virus (rAAV) that can express PAH polypeptide in a cell and thereby restore PAH gene function in the subject.

Accordingly, in one aspect, the instant disclosure provides a method for treating a subject having a disease or disorder associated with a PAH gene mutation, the method comprising administering to the subject an rAAV at a dose of about 2e13 vg/kg, 3e13 vg/kg, 4e13 vg/kg, 5e13 vg/kg, 6e13 vg/kg, 7e13 vg/kg, 8e13 vg/kg, 9e13 vg/kg, 1e14 vg/kg, 1.1e14 vg/kg, 1.2e14 vg/kg, 1.3e14 vg/kg, 1.4e14 vg/kg, 1.5e14 vg/kg, 1.6e14 vg/kg, 1.7e14 vg/kg, 1.8e14 vg/kg, 1.9e14 vg/kg, or 2e14 vg/kg (e.g., at a dose of 2e13 vg/kg, 3e13 vg/kg, 4e13 vg/kg, 5e13 vg/kg, 6e13 vg/kg, 7e13 vg/kg, 8e13 vg/kg, 9e13 vg/kg, 1e14 vg/kg, 1.1e14 vg/kg, 1.2e14 vg/kg, 1.3e14 vg/kg, 1.4e14 vg/kg, 1.5e14 vg/kg, 1.6e14 vg/kg, 1.7e14 vg/kg, 1.8e14 vg/kg, 1.9e14 vg/kg, or 2e14 vg/kg), wherein the rAAV comprises: (a) an AAV capsid comprising a capsid protein; and (b) a transfer genome comprising a silently altered PAH coding sequence, wherein the silently altered PAH coding sequence comprises the nucleotide sequence set forth in SEQ ID NO:1.

In certain embodiments, the transfer genome further comprises a transcriptional regulatory element operably linked to the silently altered PAH coding sequence.

In certain embodiments, the transcriptional regulatory element is capable of mediating transcription in a hepatocyte, a renal cell, or a cell in the brain, pituitary gland, adrenal gland, pancreas, urinary bladder, gallbladder, colon, small intestine, or breast.

In certain embodiments, the transcriptional regulatory element comprises a human hepatic control region 1 (HCR1) comprising the nucleotide sequence set forth in SEQ ID NO:2. In certain embodiments, the transcriptional regulatory element comprises a human a1-antitrypsin (hAAT) promoter comprising the nucleotide sequence set forth in SEQ ID NO:3. In certain embodiments, the transcriptional regulatory element comprises an SV40 intron comprising the nucleotide sequence set forth in SEQ ID NO:4. In certain embodiments, the transcriptional regulatory element comprises the nucleotide sequence set forth in SEQ ID NO:5.

In certain embodiments, the transfer genome further comprises an SV40 polyadenylation sequence 3' to the PAH coding sequence, wherein the SV40 polyadenylation sequence comprises the nucleotide sequence set forth in SEQ ID NO:6.

In certain embodiments, the transfer genome comprises the nucleotide sequence set forth in SEQ ID NO:7.

In certain embodiments, the transfer genome further comprises a 5' inverted terminal repeat (5' ITR) nucleotide sequence 5' of the genome, and a 3' inverted terminal repeat (3' ITR) nucleotide sequence 3' of the genome. In certain embodiments, the 5' ITR nucleotide sequence has at least 95% sequence identity to SEQ ID NO:8, and the 3' ITR nucleotide sequence has at least 95% sequence identity to SEQ ID NO:9.

In certain embodiments, the transfer genome comprises the nucleotide sequence set forth in SEQ ID NO:10.

In certain embodiments, the AAV capsid comprises: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R.

In certain embodiments, the AAV capsid comprises: a capsid protein comprising an amino acid sequence having at least 99% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 99% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 99% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R.

In certain embodiments, the AAV capsid comprises a capsid protein comprising the amino acid sequence of amino acids 203-736 of SEQ ID NO:11, a capsid protein comprising the amino acid sequence of amino acids 138-736 of SEQ ID NO:11, and/or a capsid protein comprising the amino acid sequence of amino acids 1-736 of SEQ ID NO:11.

In certain embodiments, the amino acid sequence of the capsid protein consists of the amino acid sequence of amino acids 203-736 of SEQ ID NO:11, the amino acid sequence of the capsid protein consists of the amino acid sequence of amino acids 138-736 of SEQ ID NO:11, and/or the amino acid sequence of the capsid protein consists of the amino acid sequence of amino acids 1-736 of SEQ ID NO:11.

In another aspect, the instant disclosure provides a method for treating a subject having a disease or disorder associated with a PAH gene mutation, the method comprising administering to the subject an rAAV at a dose of about 2e13 vg/kg, 3e13 vg/kg, 4e13 vg/kg, 5e13 vg/kg, 6e13 vg/kg, 7e13 vg/kg, 8e13 vg/kg, 9e13 vg/kg, 1e14 vg/kg, 1.1e14 vg/kg, 1.2e14 vg/kg, 1.3e14 vg/kg, 1.4e14 vg/kg, 1.5e14 vg/kg, 1.6e14 vg/kg, 1.7e14 vg/kg, 1.8e14 vg/kg, 1.9e14 vg/kg, or 2e14 vg/kg (e.g., at a dose of 2e13 vg/kg, 3e13 vg/kg, 4e13 vg/kg, 5e13 vg/kg, 6e13 vg/kg, 7e13 vg/kg, 8e13 vg/kg, 9e13 vg/kg, 1e14 vg/kg, 1.1e14 vg/kg, 1.2e14 vg/kg, 1.3e14 vg/kg, 1.4e14 vg/kg, 1.5e14 vg/kg, 1.6e14 vg/kg, 1.7e14 vg/kg, 1.8e14 vg/kg, 1.9e14 vg/kg, or 2e14 vg/kg), wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

In certain embodiments, the AAV capsid comprises: a capsid protein comprising an amino acid sequence having at least 99% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 99% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 99% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R.

In certain embodiments, the AAV capsid comprises: a capsid protein comprising the amino acid sequence of amino acids 203-736 of SEQ ID NO:11; a capsid protein comprising the amino acid sequence of amino acids 138-736 of SEQ ID NO:11; and/or a capsid protein comprising the amino acid sequence of amino acids 1-736 of SEQ ID NO:11.

In certain embodiments, the amino acid sequence of the capsid protein consists of the amino acid sequence of amino acids 203-736 of SEQ ID NO:11; the amino acid sequence of the capsid protein consists of the amino acid sequence of amino acids 138-736 of SEQ ID NO:11; and/or the amino acid sequence of the capsid protein consists of the amino acid sequence of amino acids 1-736 of SEQ ID NO:11.

The following embodiments apply to each of the foregoing aspects.

In certain embodiments, the dose is about 2e13 vg/kg. In certain embodiments, the dose is about 6e13 vg/kg. In certain embodiments, the dose is about 8e13 vg/kg. In certain embodiments, the dose is about 1e14 vg/kg. In certain embodiments, the dose is about 2e14 vg/kg.

In certain embodiments, the rAAV is administered as a single dose. In certain embodiments, the rAAV is administered as multiple doses. In certain embodiments, the rAAV is administered intravenously.

In certain embodiments, the subject is a pediatric subject. In certain embodiments, the subject is an adult subject.

In certain embodiments, the disease or disorder associated with a PAH gene mutation is phenylketonuria (PKU).

In another aspect, the present disclosure provides a method for treating a subject having a disease or disorder associated with a PAH gene mutation, the method comprising administering to the subject an rAAV at a dose of about 2e13 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

In another aspect, the present disclosure provides a method for treating a subject having a disease or disorder associated with a PAH gene mutation, the method comprising administering to the subject an rAAV at a dose of about 6e13 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

In another aspect, the present disclosure provides a method for treating a subject having a disease or disorder associated with a PAH gene mutation, the method comprising administering to the subject an rAAV at a dose of about 8e13 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

In another aspect, the present disclosure provides a method for treating a subject having a disease or disorder associated with a PAH gene mutation, the method comprising administering to the subject an rAAV at a dose of about 1e14 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

In another aspect, the present disclosure provides a method for treating a subject having a disease or disorder associated with a PAH gene mutation, the method comprising administering to the subject an rAAV at a dose of about 2e14 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

The following embodiments apply to each of the foregoing aspects.

In certain embodiments, the subject is administered a first immunosuppressant prior to administration of the rAAV. In certain embodiments, the first immunosuppressant is administered one day prior to the administration of the rAAV. In certain embodiments, the first immunosuppressant is administered to the subject for about 20 or about 21 weeks.

In certain embodiments, the first immunosuppressant is administered according to the following sequential dosing regimen: (1) 60 mg/day in prednisolone equivalents for two weeks; (2) 40 mg/day in prednisolone equivalents for six weeks; (3) 30 mg/day in prednisolone equivalents for three weeks; (4) 20 mg/day in prednisolone equivalents for three weeks; (5) 10 mg/day in prednisolone equivalents for five weeks; and (6) 5 mg/day in prednisolone equivalents for one or two weeks.

In certain embodiments, if the subject exhibits a level of a liver transaminase that is at least about 2 times ULN at any time during the sequential dosing regimen, the sequential dosing regimen will be restarted from step (1).

In certain embodiments, if the subject exhibits a level of a liver transaminase that is at least about 2 times ULN after completion of step (6), the subject is further administered the first immunosuppressant according to the following sequential dosing regimen: (7) 60 mg/day in prednisolone equivalents for two to four weeks; (8) 40 mg/day in prednisolone equivalents for two weeks; (9) 30 mg/day in prednisolone equivalents for two weeks; (10) 20 mg/day in prednisolone equivalents for two weeks; (11) 10 mg/day in prednisolone equivalents for two weeks; and (12) 5 mg/day in prednisolone equivalents for two weeks. In certain embodiments, step (7) is performed until the level of the liver transaminase has declined to about or less than about the subject's baseline level of the liver transaminase.

In certain embodiments, the subject's baseline level of the liver transaminase is the level of the liver transaminase in the subject prior to receiving the rAAV. In certain embodiments, the subject's baseline level of the liver transaminase is within a normal range. In certain embodiments, the subject's baseline level of the liver transaminase is at about an upper limit of normal (ULN) for the liver transaminase. In certain embodiments, the liver transaminase is alanine aminotransferase (ALT) or aspartate aminotransferase (AST).

In certain embodiments, the normal range of ALT is from 0 to about 63 U/L. In certain embodiments, the normal range of AST is from 0 to about 57 U/L. In certain embodiments, the ULN for ALT is from about 30 to about 63 U/L. In certain embodiments, the ULN for AST is about 34 to about 57 U/L.

In certain embodiments, the first immunosuppressant is a glucocorticosteroid. In certain embodiments, the first immunosuppressant is prednisolone.

BRIEF DESCRIPTION OF THE DRAWINGS

FIGS. 3A-3D are graphs showing the levels of phenylalanine (FIGS. 3A and 3C) or tyrosine (FIGS. 3B and 3D) in the serum of male (FIGS. 3A and 3B) or female (FIGS. 3C and 3D) mice administered with the indicated doses of an rAAV comprising the pHMI-hPAH-TC-025 vector.

DETAILED DESCRIPTION

Figure 1:
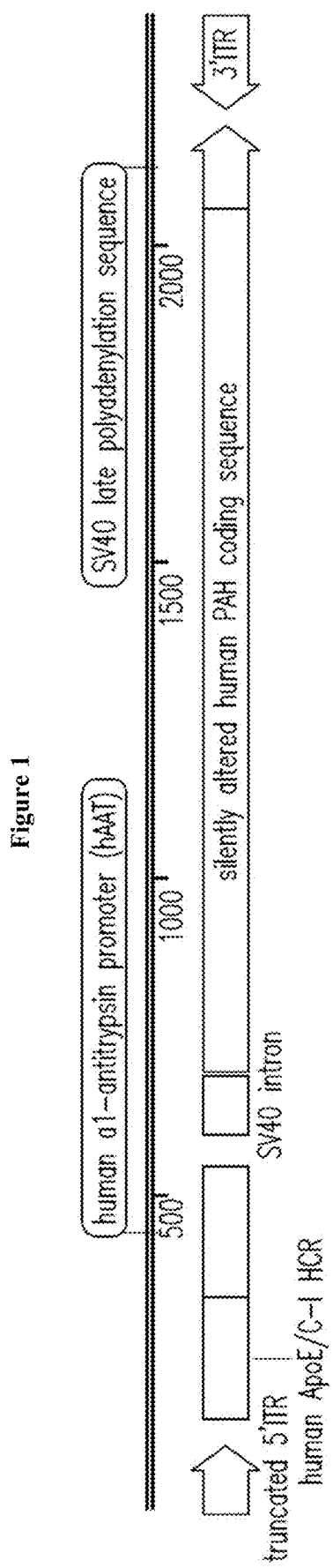
FIG. 1 is a vector map of the pHMI-hPAH-TC-025 vector.

Provided herein are methods of treating a subject having a disease or disorder associated with a PAH gene mutation. The methods generally comprise administering to the subject a therapeutically effective dose of a recombinant adeno-associated virus (rAAV) that can express a phenylalanine hydroxylase (PAH) polypeptide in a cell and thereby restore PAH gene function in the subject.

I. Definitions

As used herein, the term "AAV" is a standard abbreviation for adeno-associated virus.

As used herein, the term "recombinant adeno-associated virus" or "rAAV" refers to an AAV comprising a genome lacking functional rep and cap genes.

As used herein, the term "cap gene" refers to a nucleic acid sequence that encodes a capsid protein.

As used herein, the term "rep gene" refers to the nucleic acid sequences that encode the non-structural proteins (e.g., rep78, rep68, rep52 and rep40) required for the replication and production of an AAV.

As used herein, the term "PAH gene" refers to the phenylalanine hydroxylase gene. The human PAH gene is identified by Entrez Gene ID 5053. An exemplary nucleotide sequence of a PAH mRNA is provided as SEQ ID NO: 12. An exemplary amino acid sequence of a PAH polypeptide is provided as SEQ ID NO: 13.

As used herein, the term "transfer genome" refers to a recombinant AAV genome comprising a coding sequence operably linked to an exogenous transcriptional regulatory element that mediates expression of the coding sequence when the transfer genome is introduced into a cell. In certain embodiments, the transfer genome does not integrate in the chromosomal DNA of the cell. The skilled artisan will appreciate that the portion of a transfer genome comprising the transcriptional regulatory element operably linked to a PAH coding sequence can be in the sense or antisense orientation relative to direction of transcription of the PAH coding sequence.

As used herein, the "percentage identity" between two nucleotide sequences or between two amino acid sequences is calculated by multiplying the number of matches between the pair of aligned sequences by 100, and dividing by the length of the aligned region, including internal gaps. Identity scoring only counts perfect matches, and does not consider the degree of similarity of amino acids to one another. Note that only internal gaps are included in the length, not gaps at the sequence ends.

As used herein, the term "a disease or disorder associated with a PAH gene mutation" refers to any disease or disorder caused by, exacerbated by, or genetically linked with mutation of a PAH gene. In certain embodiments, the disease or disorder associated with a PAH gene mutation is phenylketonuria (PKU).

As used herein, the term "coding sequence" refers to the portion of a complementary DNA (cDNA) that encodes a polypeptide, starting at the start codon and ending at the stop codon. A gene may have one or more coding sequences due to alternative splicing, alternative translation initiation, and variation within the population. A coding sequence may either be wild-type or codon-altered. An exemplary wild-type PAH coding sequence is set forth in SEQ ID NO: 12.

As used herein, the term "silently altered" refers to alteration of a coding sequence or a stuffer-inserted coding sequence of a gene (e.g., by nucleotide substitution) without changing the amino acid sequence of the polypeptide encoded by the coding sequence or stuffer-inserted coding sequence. Such silent alteration is advantageous in that it may increase the translation efficiency of a coding sequence.

In the instant disclosure, nucleotide positions in a PAH gene are specified relative to the first nucleotide of the start codon. The first nucleotide of a start codon is position 1; the nucleotides 5' to the first nucleotide of the start codon have negative numbers; the nucleotides 3' to the first nucleotide of the start codon have positive numbers. An exemplary nucleotide 1 of the human PAH gene is nucleotide 5,473 of the NCBI Reference Sequence: NG_008690.1, and an exemplary nucleotide 3 of the human PAH gene is nucleotide 5,475 of the NCBI Reference Sequence: NG_008690.1. The nucleotide adjacently 5' to the start codon is nucleotide −1.

In the instant disclosure, exons and introns in a PAH gene are specified relative to the exon encompassing the first nucleotide of the start codon, which is nucleotide 5473 of the NCBI Reference Sequence: NG_008690.1. The exon encompassing the first nucleotide of the start codon is exon 1. Exons 3' to exon 1 are from 5' to 3': exon 2, exon 3, etc. Introns 3' to exon 1 are from 5' to 3': intron 1, intron 2, etc. Accordingly, the PAH gene comprises from 5' to 3': exon 1, intron 1, exon 2, intron 2, exon 3, etc. An exemplary exon 1 of the human PAH gene is nucleotides 5001-5532 of the NCBI Reference Sequence: NG_008690.1. An exemplary intron 1 of the human PAH gene is nucleotides 5533-9704 of the NCBI Reference Sequence: NG_008690.1.

As used herein, the term "transcriptional regulatory element" or "TRE" refers to a cis-acting nucleotide sequence, for example, a DNA sequence, that regulates (e.g., controls, increases, or reduces) transcription of an operably linked nucleotide sequence by an RNA polymerase to form an RNA molecule. A TRE relies on one or more trans-acting molecules, such as transcription factors, to regulate transcription. Thus, one TRE may regulate transcription in different ways when it is in contact with different trans-acting molecules, for example, when it is in different types of cells. A TRE may comprise one or more promoter elements and/or enhancer elements. A skilled artisan would appreciate that the promoter and enhancer elements in a gene may be close in location, and the term "promoter" may refer to a sequence comprising a promoter element and an enhancer element. Thus, the term "promoter" does not exclude an enhancer element in the sequence. The promoter and enhancer elements do not need to be derived from the same gene or species, and the sequence of each promoter or enhancer element may be either identical or substantially identical to the corresponding endogenous sequence in the genome.

As used herein, the term "operably linked" is used to describe the connection between a TRE and a coding sequence to be transcribed. Typically, gene expression is placed under the control of a TRE comprising one or more promoter and/or enhancer elements. The coding sequence is "operably linked" to the TRE if the transcription of the coding sequence is controlled or influenced by the TRE. The promoter and enhancer elements of the TRE may be in any orientation and/or distance from the coding sequence, as long as the desired transcriptional activity is obtained. In certain embodiments, the TRE is upstream from the coding sequence.

As used herein, the term "polyadenylation sequence" refers to a DNA sequence that when transcribed into RNA constitutes a polyadenylation signal sequence. The polyadenylation sequence can be native (e.g., from the PAH gene) or exogenous. The exogenous polyadenylation sequence can be a mammalian or a viral polyadenylation sequence (e.g., an SV40 polyadenylation sequence).

As used herein, "exogenous polyadenylation sequence" refers to a polyadenylation sequence not identical or substantially identical to the endogenous polyadenylation sequence of a PAH gene (e.g., human PAH gene). In certain embodiments, an exogenous polyadenylation sequence is a polyadenylation sequence of a non-PAH gene in the same species (e.g., human). In certain embodiments, an exogenous polyadenylation sequence is a polyadenylation sequence of a different species (e.g., a virus).

As used herein, the term "effective amount" in the context of the administration of an AAV to a subject refers to the amount of the AAV that achieves a desired prophylactic or therapeutic effect.

As used herein, the term "about" or "approximately" when referring to a measurable value, such as a dosage, encompasses variations of ±20% or ±10%, ±5%, ±1%, or ±0.1% of a given value or range, as are appropriate to perform the methods disclosed herein.

As used herein in the context of the result of a liver function test (e.g., the level of a liver transaminase in the blood of a subject), the term "normal range," refers to a reference range expected for a healthy subject (i.e., a non-pathophysiological reference range). It is appreciated by those of skill in the art that a reference range varies between laboratory testing sites. As such, when determining whether a test value is within a normal range, the reference range supplied by the laboratory testing site that obtained the test value should be used. Further, it is known in the art that a reference range for a certain liver function test may be different for male and female sexes. Common liver function tests include determining the level of alanine aminotransferase (ALT), aspartate aminotransferase (AST), alkaline phosphate (ALP), gamma-glutamyltransferase (GGT), bilirubin, and albumin. Liver function tests also include determining the prothrombin time (PT), which is a test that measures how long it takes blood to clot. In certain embodiments, the reference range for ALT is from 0 to about 45 IU/L, from about 3 to about 30 U/L, from about 1 to about 45 U/L, from about 17 to about 63 U/L, from about 14 to about 54 U/L. In certain embodiments, the reference range for AST is from 0 to about 35 IU/L, from about 2 to about 40 U/L, from about 1 to about 35 U/L, from about 18 to about 57 U/L, from about 5 to about 34 U/L, from about 15 to about 41 U/L. In certain embodiments, the reference range for ALP is from about 30 to about 120 IU/L, from about 38 to about 126 U/L, from about 69 to about 318 U/L, from about 53 to about 212 U/L, from about 34 to about 104 U/L. In certain embodiments, the reference range for direct bilirubin is from about 2 to about 17 μmol/L, from about 0 to about 0.4 mg/dL, from about 0 to about 0.8 mg/dL, from about 0 to about 0.3 mg/dL, from about 0 to about 0.2 mg/dL. In certain embodiments, the reference range for total bilirubin is from about 0.3 to about 1.2 mg/dL, from about 0.1 to about 1.2 mg/dL, from about 0.2 to about 1.2 mg/dL. In certain embodiments, the reference range for prothrombin time is from about 10.9 to about 12.5 seconds. In certain embodiments, the reference range for albumin is from about 40 to about 60 g/L.

As used herein in the context of the result of a liver function test (e.g., the level of a liver transaminase in the blood of a subject), "baseline value," refers to a result of a liver function test that was obtained prior to the administration of a treatment described herein (e.g., administration of a gene therapy to the subject). In certain embodiments, the baseline value for a liver function test is the result of the liver function test obtained from the subject prior to the administration of the gene therapy (e.g., a liver directed gene therapy). For example, the baseline value for ALT and/or AST is the value of ALT and/or AST obtained from the subject prior to the administration of a gene therapy.

In certain embodiments, the result of a liver function test may be reported as a multiple of a certain reference value. For example, the result of a liver function test may be reported as a multiple of an upper limit of normal. As used herein, the term "upper limit of normal" or "ULN," refers to the upper value of a reference range. For example, the ULN for ALT is the upper value of the reference range for ALT. In certain embodiments, the ULN for ALT is about 45 IU/L, about 30 U/L, about 45 U/L, about 63 U/L, about 54 U/L. In certain embodiments, the ULN for ALT is from about 30 U/L to about 63 U/L. In certain embodiments, the ULN for AST is about 35 IU/L, about 40 U/L, about 57 U/L, about 34 U/L, about 41 U/L. In certain embodiments, the ULN for AST is from about 34 U/L to about 57 U/L. In certain embodiments, the ULN for ALP is about 120 IU/L, about 126 U/L, about 318 U/L, about 212 U/L, about 104 U/L. In certain embodiments, the ULN for ALP is from about 104 U/L to about 318 U/L. In certain embodiments, the ULN for direct bilirubin is about 17 μmol/L, about 0.4 mg/dL, about 0.8 mg/dL, about 0.3 mg/dL, about 0.2 mg/dL. In certain embodiments, the ULN for direct bilirubin is from about 0.2 mg/dL to about 0.8 mg/dL. In certain embodiments, the ULN for total bilirubin is about 1.2 mg/dL. In certain embodiments, the ULN for prothrombin time is about 12.5 seconds. In certain embodiments, the ULN for albumin is about 60 g/L. As such, the result of a liver function test may be reported as, e.g., at least about 1.5 times the ULN, at least about 2 times the ULN, at least about 2.5 times the ULN, at least about 3 times the ULN, at least about 4 times the ULN, at least 5 times the ULN, at least 20 times the ULN, and the like.

An event such as elevated ALT can be described by a certain Grade. As used herein, the term "Grade" when used in the context of an event, refers to the Grade designation as provided by Common Terminology Criteria for Adverse Events (CTCAE). For example, the level of ALT elevation can be described as Grade 1 (greater than about 1 to about 3 times ULN if baseline was normal; greater than about 1.5 to about 3 times baseline if baseline was abnormal), Grade 2 (greater than about 3 to about 5 times ULN if baseline was normal; greater than about 3 to about 5 times baseline if baseline was abnormal), Grade 3 (greater than about to about 20 times ULN if baseline was normal; greater than about 5 to about 20 times baseline if baseline was abnormal), and Grade 4 (greater than about 20 times ULN if baseline was normal; greater than about 20 times baseline if baseline was abnormal).

II. Recombinant Adeno-Associated Virus

The instant disclosure provides methods of treating a subject having a disease or disorder associated with a PAH gene mutation. The methods generally comprise administering to the subject a therapeutically effective does of a recombinant adeno-associated virus (rAAV) disclosed herein at a dose of about 2e13 vg/kg to about 2e14 kg/vg. rAAV suitable for use in these methods are described in detail below.

In certain embodiments, the rAAV employed in the methods disclosed herein disclosed comprise: an AAV capsid comprising a capsid protein; and a transfer genome comprising a transcriptional regulatory element operably linked to a PAH coding sequence (e.g., a silently altered PAH coding sequence), allowing for extrachromosomal expression of PAH in a cell transduced with the AAV.

In certain embodiments, the AAV capsid comprises one or more of: (a) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; (b) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (c) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R.

In certain embodiments, the AAV capsid comprises one or more of: (a) a capsid protein comprising the amino acid sequence of amino acids 203-736 of SEQ ID NO:11; (b) a capsid protein comprising the amino acid sequence of amino acids 138-736 of SEQ ID NO:11; and (c) a capsid protein comprising the amino acid sequence of amino acids 1-736 of SEQ ID NO:11.

In certain embodiments, the AAV capsid comprises two or more of: (a) a capsid protein comprising the amino acid sequence of amino acids 203-736 of SEQ ID NO:11; (b) a capsid protein comprising the amino acid sequence of amino acids 138-736 of SEQ ID NO:11; and (c) a capsid protein comprising the amino acid sequence of amino acids 1-736 of SEQ ID NO:11.

In certain embodiments, the AAV capsid comprises: (a) a capsid protein having an amino acid sequence consisting of amino acids 203-736 of SEQ ID NO:11; (b) a capsid protein having an amino acid sequence consisting of amino acids 138-736 of SEQ ID NO:11; and (c) a capsid protein having an amino acid sequence consisting of amino acids 1-736 of SEQ ID NO:11.

In certain embodiments, the amino acid sequence of the capsid protein consists of the amino acid sequence of amino acids 203-736 of SEQ ID NO:11; the amino acid sequence of the capsid protein consists of the amino acid sequence of amino acids 138-736 of SEQ ID NO:11, and/or the amino acid sequence of the capsid protein consists of the amino acid sequence of amino acids 1-736 of SEQ ID NO:11.

Transfer genomes useful in the rAAV generally comprise a transcriptional regulatory element (TRE) operably linked to a PAH coding sequence. In certain embodiments, the transfer genome comprises a 5' inverted terminal repeat (5' ITR) nucleotide sequence 5' of the TRE and PAH coding sequence, and a 3' inverted terminal repeat (3' ITR) nucleotide sequence 3' of the TRE and PAH coding sequence.

In certain embodiments, the PAH coding sequence comprises all or substantially all of a coding sequence of a PAH gene. In certain embodiments, the transfer genome comprises a nucleotide sequence encoding SEQ ID NO: 13 and can optionally further comprise an exogenous polyadenylation sequence 3' to the PAH coding sequence. In certain embodiments, the nucleotide sequence encoding SEQ ID NO: 13 is wild-type (e.g., having the sequence set forth in SEQ ID NO: 12). In certain embodiments, the nucleotide sequence encoding SEQ ID NO: 13 is codon-altered (e.g., having the sequence set forth in SEQ ID NO: 1).

In certain embodiments, the PAH coding sequence encodes a polypeptide comprising all or substantially all of the amino acids sequence of a PAH protein. In certain embodiments, the PAH coding sequence encodes the amino acid sequence of a wild-type PAH protein (e.g., human PAH protein). In certain embodiments, the PAH coding sequence encodes the amino acid sequence of a mutant PAH protein (e.g., human PAH protein), wherein the mutant PAH polypeptide is a functional equivalent of the wild-type PAH polypeptide, i.e., can function as a wild-type PAH polypeptide. In certain embodiments, the functionally equivalent PAH polypeptide further comprises at least one characteristic not found in the wild-type PAH polypeptide, e.g., the ability to stabilize PAH protein (e.g., dimer or tetramer), or the ability to resist protein degradation.

The transfer genome can be used to express PAH in any mammalian cells (e.g., human cells). Thus, the TRE can be active in any mammalian cells (e.g., human cells). In certain embodiments, the TRE is active in a broad range of human cells. Such TREs may comprise constitutive promoter and/or enhancer elements including Alternatively, the TRE may be a tissue-specific TRE, i.e., it is active in specific tissue(s) and/or organ(s). A tissue-specific TRE comprises one or more tissue-specific promoter and/or enhancer elements, and optionally one or more constitutive promoter and/or enhancer elements. A skilled artisan would appreciate that tissue-specific promoter and/or enhancer elements can be isolated from genes specifically expressed in the tissue by methods well known in the art. In certain embodiments, the TRE is liver-specific (e.g., hepatocyte-specific). Exemplary liver-specific TREs may comprise one or more elements including human APOE/C-I hepatic control region (HCR) 1 or 2 (e.g., comprising a nucleotide sequence at least 90%, 91%, 92%, 93%, 94%, 95%, 96%, 97%, 98%, 99%, or 100% identical to SEQ ID NO: 2 or 14), and human SERPINA1 (hAAT) promoter (e.g., comprising a nucleotide sequence at least 90%, 91%, 92%, 93%, 94%, 95%, 96%, 97%, 98%, 99%, or 100% identical to SEQ ID NO: 3 or 15).

In certain embodiments, the transfer genome comprises two or more TREs, optionally comprising at least one of the TREs disclosed above. A skilled person in the art would appreciate that any of these TREs can be combined in any order, and combinations of a constitutive TRE and a tissue-specific TRE can drive efficient and tissue-specific transcription.

Similarly, combinations of two or more tissue-specific TREs can drive efficient and tissue-specific transcription. For example, in certain embodiments, the transfer genome comprises a human HCR1 (e.g., comprising a nucleotide sequence at least 90%, 91%, 92%, 93%, 94%, 95%, 96%, 97%, 98%, or 99% identical to SEQ ID NO: 2) and a hAAT promoter (e.g., comprising a nucleotide sequence at least 90%, 91%, 92%, 93%, 94%, 95%, 96%, 97%, 98%, or 99% identical to SEQ ID NO: 3), optionally wherein the human HCR1 is 5' to the hAAT promoter. In certain embodiments, the transfer genome comprises a nucleotide sequence at least 90%, 91%, 92%, 93%, 94%, 95%, 96%, 97%, 98%, or 99% identical to the sequence set forth in SEQ ID NO: 5. In certain embodiments, the transfer genome comprises a human HCR1 (e.g., comprising the nucleotide sequence set forth in SEQ ID NO: 2) and a hAAT promoter (e.g., comprising the nucleotide sequence set forth in SEQ ID NO: 3), optionally wherein the human HCR1 is 5' to the hAAT promoter. In certain embodiments, the transfer genome comprises the nucleotide sequence set forth in SEQ ID NO: 5.

In certain embodiments, the transfer vector further comprises an intron 5' to or inserted in the PAH coding sequence. Such introns can increase transgene expression, for example, by reducing transcriptional silencing and enhancing mRNA export from the nucleus to the cytoplasm. In certain embodiments, the transfer genome comprises from 5' to 3': a non-coding exon, an intron, and the PAH coding sequence. In certain embodiments, an intron sequence is inserted in the PAH coding sequence, optionally wherein the intron is inserted at an internucleotide bond that links two native exons. In certain embodiments, the intron is inserted at an internucleotide bond that links native exon 1 and exon 2.

The intron can comprise a native intron sequence of the PAH gene, an intron sequence from a different species or a different gene from the same species, and/or a synthetic intron sequence. A skilled worker will appreciate that synthetic intron sequences can be designed to mediate RNA splicing by introducing any consensus splicing motifs known in the art (e.g., in Sibley et al., (2016) Nature Reviews Genetics, 17, 407-21, which is incorporated by reference herein in its entirety). Exemplary intron sequences are provided in Lu et al. (2013) Molecular Therapy 21(5): 954-63, and Lu et al. (2017) Hum. Gene Ther. 28(1): 125-34, which are incorporated by reference herein in their entirety. In certain embodiments, the transfer genome comprises an SV40 intron (e.g., comprising a nucleotide sequence at least 90%, 91%, 92%, 93%, 94%, 95%, 96%, 97%, 98%, or 99% identical to SEQ ID NO: 4).

In certain embodiments, the transfer genome disclosed herein further comprises a transcription terminator (e.g., a polyadenylation sequence). In certain embodiments, the transcription terminator is 3' to the PAH coding sequence. The transcription terminator may be any sequence that effectively terminates transcription, and a skilled artisan would appreciate that such sequences can be isolated from any genes that are expressed in the cell in which transcription of the PAH coding sequence is desired. In certain embodiments, the transcription terminator comprises a polyadenylation sequence. In certain embodiments, the polyadenylation sequence is identical or substantially identical to the endogenous polyadenylation sequence of the human PAH gene. In certain embodiments, the polyadenylation sequence is an exogenous polyadenylation sequence. In certain embodiments, the polyadenylation sequence is an SV40 polyadenylation sequence (e.g., comprising the nucleotide sequence set forth in SEQ ID NO: 6, or a nucleotide sequence complementary thereto). In certain embodiments, the polyadenylation sequence comprises the sequence set forth in SEQ ID NO: 6.

In certain embodiments, the transfer genome comprises from 5' to 3': a TRE, optionally a non-coding exon and an intron, a PAH coding sequence, and a polyadenylation sequence. In certain embodiments, the TRE has at least 90%, 91%, 92%, 93%, 94%, 95%, 96%, 97%, 98%, or 99% sequence identity to any one of SEQ ID NOs: 2, 3, and 5; the intron has at least 90%, 91%, 92%, 93%, 94%, 95%, 96%, 97%, 98%, or 99% sequence identity to SEQ ID NO: 4; the PAH coding sequence has at least 90%, 91%, 92%, 93%, 94%, 95%, 96%, 97%, 98%, or 99% sequence identity to SEQ ID NO: 1; and/or the polyadenylation sequence has at least 90%, 91%, 92%, 93%, 94%, 95%, 96%, 97%, 98%, or 99% sequence identity to any one of SEQ ID NOs: 6. In certain embodiments, the TRE comprises a nucleotide sequence selected from the group consisting of SEQ ID NOs: 2, 3, and 5; the intron comprises a nucleotide sequence selected from the group consisting of SEQ ID NO: 4; the PAH coding sequence comprises the sequence set forth in SEQ ID NO: 1; and/or the polyadenylation sequence comprises a nucleotide sequence selected from the group consisting of SEQ ID NOs: 6. In certain embodiments, the TRE comprises from 5' to 3' the sequence set forth in SEQ ID NO: 2, and the sequence set forth in SEQ ID NO: 3 (e.g., the TRE comprises the sequence set forth in SEQ ID NO: 5); the intron comprises the sequence set forth in SEQ ID NO: 4; the PAH coding sequence comprises the sequence set forth in SEQ ID NO: 1; and/or the polyadenylation sequence comprises the sequence set forth in SEQ ID NO: 6.

In certain embodiments, the transfer genome comprises a sequence at least 80%, 85%, 90%, 91%, 92%, 93%, 94%, 95%, 96%, 97%, 98%, or 99% identical to SEQ ID NO: 7. In certain embodiments, the transfer genome comprises the nucleotide sequence set forth in SEQ ID NO: 7. In certain embodiments, the transfer genome consists of the nucleotide sequence set forth in SEQ ID NO: 7.

In certain embodiments, the transfer genomes disclosed herein further comprise a 5' inverted terminal repeat (5' ITR) nucleotide sequence 5' of the TRE, and a 3' inverted terminal repeat (3' ITR) nucleotide sequence 3' of the PAH coding sequence. ITR sequences from any AAV serotype or variant thereof can be used in the transfer genomes disclosed herein. The 5' and 3' ITR can be from an AAV of the same serotype or from AAVs of different serotypes. Exemplary ITRs for use in the transfer genomes disclosed herein are set forth in SEQ ID NOs: 8, 9, and 16-19 herein.

In certain embodiments, the 5' ITR or 3' ITR is from AAV2. In certain embodiments, both the 5' ITR and the 3' ITR are from AAV2. In certain embodiments, the 5' ITR nucleotide sequence has at least 90% (e.g., at least 95%, at least 96%, at least 97%, at least 98%, at least 99%, or 100%) sequence identity to SEQ ID NO: 16, or the 3' ITR nucleotide sequence has at least 90% (e.g., at least 95%, at least 96%, at least 97%, at least 98%, at least 99%, or 100%) sequence identity to SEQ ID NO: 17. In certain embodiments, the 5' ITR nucleotide sequence has at least 90% (e.g., at least 95%, at least 96%, at least 97%, at least 98%, at least 99%, or 100%) sequence identity to SEQ ID NO: 16, and the 3' ITR nucleotide sequence has at least 90% (e.g., at least 95%, at least 96%, at least 97%, at least 98%, at least 99%, or 100%) sequence identity to SEQ ID NO: 17. In certain embodiments, the transfer genome comprises a nucleotide sequence set forth in any one of SEQ ID NOs: 7, a 5' ITR nucleotide sequence having the sequence of SEQ ID NO: 16, and a 3' ITR nucleotide sequence having the sequence of SEQ ID NO: 17.

In certain embodiments, the 5' ITR or 3' ITR are from AAV5. In certain embodiments, both the 5' ITR and 3' ITR are from AAV5. In certain embodiments, the 5' ITR nucleotide sequence has at least 90% (e.g., at least 95%, at least 96%, at least 97%, at least 98%, at least 99%, or 100%) sequence identity to SEQ ID NO: 18, or the 3' ITR nucleotide sequence has at least 90% (e.g., at least 95%, at least 96%, at least 97%, at least 98%, at least 99%, or 100%) sequence identity to SEQ ID NO: 19. In certain embodiments, the 5' ITR nucleotide sequence has at least 90% (e.g., at least 95%, at least 96%, at least 97%, at least 98%, at least 99%, or 100%) sequence identity to SEQ ID NO: 18, and the 3' ITR nucleotide sequence has at least 90% (e.g., at least 95%, at least 96%, at least 97%, at least 98%, at least 99%, or 100%) sequence identity to SEQ ID NO: 19. In certain embodiments, the transfer genome comprises a nucleotide sequence set forth in any one of SEQ ID NOs: 7, a 5' ITR nucleotide sequence having the sequence of SEQ ID NO: 18, and a 3' ITR nucleotide sequence having the sequence of SEQ ID NO: 19.

In certain embodiments, the 5' ITR nucleotide sequence and the 3' ITR nucleotide sequence are substantially complementary to each other (e.g., are complementary to each other except for mismatch at 1, 2, 3, 4, or 5 nucleotide positions in the 5' or 3' ITR).

In certain embodiments, the 5' ITR or the 3' ITR is modified to reduce or abolish resolution by Rep protein ("non-resolvable ITR"). In certain embodiments, the non-resolvable ITR comprises an insertion, deletion, or substitution in the nucleotide sequence of the terminal resolution site. Such modification allows formation of a self-complementary, double-stranded DNA genome of the AAV after the transfer genome is replicated in an infected cell. Exemplary non-resolvable ITR sequences are known in the art (see e.g., those provided in U.S. Pat. Nos. 7,790,154 and 9,783,824, which are incorporated by reference herein in their entirety). In certain embodiments, the 5' ITR comprises a nucleotide sequence at least 95%, 96%, 97%, 98%, or 99% identical to SEQ ID NO: 8. In certain embodiments, the 5' ITR consists of a nucleotide sequence at least 95%, 96%, 97%, 98%, or 99% identical to SEQ ID NO: 8. In certain embodiments, the 5' ITR consists of the nucleotide sequence set forth in SEQ ID NO: 8. In certain embodiments, the 3' ITR comprises a nucleotide sequence at least 95%, 96%, 97%, 98%, or 99% identical to SEQ ID NO: 9. In certain embodiments, the 5' ITR consists of a nucleotide sequence at least 95%, 96%, 97%, 98%, or 99% identical to SEQ ID NO: 9. In certain embodiments, the 3' ITR consists of the nucleotide sequence set forth in SEQ ID NO: 9. In certain embodiments, the 5' ITR consists of the nucleotide sequence set forth in SEQ ID NO: 8, and the 3' ITR consists of the nucleotide sequence set forth in SEQ ID NO: 9. In certain embodiments, the 5' ITR consists of the nucleotide sequence set forth in SEQ ID NO: 8, and the 3' ITR consists of the nucleotide sequence set forth in SEQ ID NO: 17.

In certain embodiments, the 3' ITR is flanked by an additional nucleotide sequence derived from a wild-type AAV2 genomic sequence. In certain embodiments, the 3' ITR is flanked by an additional 37 bp sequence derived from a wild-type AAV2 sequence that is adjacent to a wild-type AAV2 ITR. See, e.g., Savy et al., *Human Gene Therapy Methods* (2017) 28(5): 277-289 (which is hereby incorporated by reference herein in its entirety). In certain embodiments, the additional 37 bp sequence is internal to the 3' ITR. In certain embodiments, the 37 bp sequence consists of the sequence set forth in SEQ ID NO: 20. In certain embodiments, the 3' ITR comprises a nucleotide sequence at least 95%, 96%, 97%, 98%, or 99% identical to SEQ ID NO: 21. In certain embodiments, the 3' ITR comprises the nucleotide sequence set forth in SEQ ID NO: 21. In certain embodiments, the nucleotide sequence of the 3' ITR consists of a nucleotide sequence at least 95%, 96%, 97%, 98%, or 99% identical to SEQ ID NO: 21. In certain embodiments, the nucleotide sequence of the 3' ITR consists of the nucleotide sequence set forth in SEQ ID NO: 21.

In certain embodiments, the transfer genome comprises from 5' to 3': a 5' ITR; an internal element comprising from 5' to 3': a TRE, optionally a non-coding exon and an intron, a PAH coding sequence, and a polyadenylation sequence, as disclosed herein; a non-resolvable ITR; a nucleotide sequence complementary to the internal element; and a 3' ITR. Such transfer genome can form a self-complementary, double-stranded DNA genome of the AAV after infection and before replication.

In certain embodiments, the transfer genome comprises from 5' to 3': a 5' ITR, a TRE, optionally a non-coding exon and an intron, a PAH coding sequence, a polyadenylation sequence, and a 3' ITR. In certain embodiments, the 5' ITR has at least 90%, 91%, 92%, 93%, 94%, 95%, 96%, 97%, 98%, or 99% sequence identity to SEQ ID NO: 8, 16, or 18; the TRE has at least 90%, 91%, 92%, 93%, 94%, 95%, 96%, 97%, 98%, or 99% sequence identity to any one of SEQ ID NO: 2, 3, or 5; the intron has at least 90%, 91%, 92%, 93%, 94%, 95%, 96%, 97%, 98%, or 99% sequence identity to SEQ ID NO: 4; the PAH coding sequence has at least 90%, 91%, 92%, 93%, 94%, 95%, 96%, 97%, 98%, or 99% sequence identity to SEQ ID NO: 1; the polyadenylation sequence has at least 90%, 91%, 92%, 93%, 94%, 95%, 96%, 97%, 98%, or 99% sequence identity to any one of SEQ ID NO: 6; and/or the 3' ITR has at least 90%, 91%, 92%, 93%, 94%, 95%, 96%, 97%, 98%, or 99% sequence identity to SEQ ID NO: 9, 17, or 19. In certain embodiments, the 5' ITR comprises or consists of a nucleotide sequence selected from the group consisting of SEQ ID NOs: 8, 16, or 18; the TRE comprises a nucleotide sequence selected from the group consisting of SEQ ID NOs: 2, 3, or 5; the intron comprises a nucleotide sequence selected from the group consisting of SEQ ID NOs: 4; the PAH coding sequence comprises the sequence set forth in SEQ ID NO: 1; the polyadenylation sequence comprises a nucleotide sequence selected from the group consisting of SEQ ID NO: 6; and/or the 3' ITR comprises or consists of a nucleotide sequence selected from the group consisting of SEQ ID NOs: 9, 17, or 19. In certain embodiments, the 5' ITR comprises or consists of the sequence set forth in SEQ ID NO: 8; the TRE comprises from 5' to 3' the sequence set forth in SEQ ID NO: 2, and the sequence set forth in SEQ ID NO: 3 (e.g., the TRE comprises the sequence set forth in SEQ ID NO: 5); the intron comprises the sequence set forth in SEQ ID NO: 4; the PAH coding sequence comprises the sequence set forth in SEQ ID NO: 1; the polyadenylation sequence comprises the sequence set forth in SEQ ID NO: 6 and/or the 3' ITR comprises or consists of the sequence set forth in SEQ ID NO: 9.

In certain embodiments, the transfer genome comprises a sequence at least 80% (e.g., at least 85%, 90%, 91%, 92%, 93%, 94%, 95%, 96%, 97%, 98%, or 99%) identical to the sequence set forth in SEQ ID NO: 10. In certain embodiments, the transfer genome comprises the sequence set forth in SEQ ID NO: 10. In certain embodiments, the transfer genome consists of the sequence set forth in SEQ ID NO: 10.

In certain embodiments, the rAAV comprises: (a) an AAV capsid protein comprising the amino acid sequence of amino acids 203-736 of SEQ ID NO:11, and a transfer genome comprising 5' to 3' following genetic elements: a 5' ITR element (e.g., the 5' ITR of SEQ ID NO: 8), a human HCR1 (e.g., the HCR1 of SEQ ID NO: 2), an hAAT promoter (e.g., the hAAT promoter of SEQ ID NO: 3), an SV40 intron (e.g., the SV40 intron of SEQ ID NO: 4), a silently altered human PAH coding sequence (e.g., the PAH coding sequence of SEQ ID NO: 1), an SV40 polyadenylation sequence (e.g., the SV40 polyadenylation sequence of SEQ ID NO: 6), and a 3' ITR element (e.g., the 3' ITR of SEQ ID NO: 9); (b) an AAV capsid protein comprising the amino acid sequence of amino acids 138-736 of SEQ ID NO:11, and a transfer genome comprising 5' to 3' following genetic elements: a 5' ITR element (e.g., the 5' ITR of SEQ ID NO: 8), a human HCR1 (e.g., the HCR1 of SEQ ID NO: 2), an hAAT promoter (e.g., the hAAT promoter of SEQ ID NO: 3), an SV40 intron (e.g., the SV40 intron of SEQ ID NO: 4), a silently altered human PAH coding sequence (e.g., the PAH coding sequence of SEQ ID NO: 1), an SV40 polyadenylation sequence (e.g., the SV40 polyadenylation sequence of SEQ ID NO: 6), and a 3' ITR element (e.g., the 3' ITR of SEQ ID NO: 9); and/or (c) an AAV capsid protein comprising the amino acid sequence of SEQ ID NO:11, and a transfer genome comprising 5' to 3' following genetic elements: a 5' ITR element (e.g., the 5' ITR of SEQ ID NO: 8), a human HCR1 (e.g., the HCR1 of SEQ ID NO: 2), an hAAT promoter (e.g., the hAAT promoter of SEQ ID NO: 3), an SV40 intron (e.g., the SV40 intron of SEQ ID NO: 4), a silently altered human PAH coding sequence (e.g., the PAH coding sequence of SEQ ID NO: 1), an SV40 polyadenylation sequence (e.g., the SV40 polyadenylation sequence of SEQ ID NO: 6), and a 3' ITR element (e.g., the 3' ITR of SEQ ID NO: 9).

In certain embodiments, the rAAV comprises: (a) an AAV capsid protein comprising the amino acid sequence of amino acids 203-736 of SEQ ID NO:11, and a transfer genome comprising the nucleotide sequence set forth in any one of SEQ ID NOs: 7 or 10; (b) an AAV capsid protein comprising the amino acid sequence of amino acids 138-736 of SEQ ID NO:11, and a transfer genome comprising the nucleotide sequence set forth in any one of SEQ ID NOs: 7 or 10; and/or (c) an AAV capsid protein comprising the amino acid sequence of SEQ ID NO:11, and a transfer genome comprising the nucleotide sequence set forth in any one of SEQ ID NOs: 7 or 10.

In certain embodiments, the rAAV are present in pharmaceutical compositions comprising an rAAV as disclosed herein together with a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in Remington's Pharmaceutical Sciences, current Ed., Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al, 7th ed., Lippincott, Williams, & Wilkins; and Handbook of Pharmaceutical Excipients (2000) A. H. Kibbe et al, 3rd ed. Amer. Pharmaceutical Assoc.

In certain embodiments, relative amounts vary of the active ingredient (e.g., rAAV), a pharmaceutically acceptable excipient, and/or any other ingredients. In certain embodiments, the relative amounts may depend upon various factors, including, without limitation, the subject's size (e.g., weight) and the subject's overall health. In certain embodiments, a pharmaceutical composition of the present disclosure contains from about 0.1% to about 100% (w/w) of the active ingredient. For example, a pharmaceutical composition of the present disclosure comprises from about 0.1% to about 10.0% (w/w), from about 5.0% to about 15.0% (w/w), from about 10.0% to about 20.0% (w/w), from about 15.0% to about 25.0% (w/w), from about 20.0% to about 30.0% (w/w), from about 25.0% to about 35.0% (w/w), from about 30.0% to about 40.0% (w/w), from about 35.0% to about 45.0% (w/w), from about 40.0% to about 50.0% (w/w), from about 45.0% to about 55.0% (w/w), from about 50.0% to about 60.0% (w/w), from about 55.0% to about 65.0% (w/w), from about 60.0% to about 70.0% (w/w), from about 65.0% to about 75.0% (w/w), from about 70.0% to about 80.0% (w/w), from about 75.0% to about 85.0% (w/w), from about 80.0% to about 90.0% (w/w), from about 85.0% to about 95.0%, from about 90.0% to about 100.0% (w/w), or relative amount in between.

In certain embodiments, the pharmaceutical compositions are suitable for administration to a subject in need thereof (e.g., a subject having a disease or disorder associated with PAH deficiency). The subject in need can be any animal. For example, the animal may be a mammal, such as a primate (e.g., human or monkey) or a non-primate (e.g., mouse, rat, cat, dog, cow, pig, or horse, etc.). For example, the subject can be a non-mammal, e.g., chicken or duck, etc. Those of skill in the art will be able to determine routine modifications to the formulation or pharmaceutical composition to render it suitable for administration to various animals. In certain embodiments, and pharmaceutical compositions provided herein are suitable for administration to a human subject.

In certain embodiments, pharmaceutical compositions can be prepared by any method known by those of skill in the art. pharmaceutical compositions may include, without limitation, salts, buffers, carbohydrates, sugars, proteins, peptides, and other components known in the art.

III. Methods of Use

The instant disclosure provides methods of treating a subject having a disease or disorder associated with a PAH gene mutation. The methods generally comprise administering to the subject a recombinant adeno-associated virus (rAAV) disclosed herein at a dose of about 2e13 vg/kg to about 2e14 kg/vg.

The methods disclosed herein can be applied to any cell harboring a mutation in the PAH gene. The skilled worker will appreciate that cells that are active in Phe metabolism are of particular interest. Accordingly, in certain embodiments, the methods are applied to cells in the liver, kidney, brain, pituitary gland, adrenal gland, pancreas, urinary bladder, gallbladder, colon, small intestine, or breast. In certain embodiments, the method is applied to hepatocytes and/or renal cells.

In certain embodiments, the cell to be transduced is in a mammalian subject and the AAV is administered to the subject in an amount effective to transduce the cell in the subject. Accordingly, in certain embodiments, the instant disclosure provides a method for treating a subject having a disease or disorder associated with a PAH gene mutation, the method generally comprising administering to the subject an effective amount of an rAAV as disclosed herein. The subject can be a human subject, a non-human primate subject (e.g., a cynomolgus), or a rodent subject (e.g., a mouse) with a PAH mutation, or a non-human primate subject (e.g., a cynomolgus) or a rodent subject (e.g., a mouse) containing PAH-mutant human liver cells. Suitable mouse subjects include without limitation, mice into which human liver cells (e.g., human hepatocytes) have been engrafted. Any disease or disorder associated with a PAH gene mutation can be treated using the methods disclosed herein. Suitable diseases or disorders include, without limitation, phenylketonuria.

In certain embodiments, the foregoing methods employ an rAAV comprising: (a) an AAV capsid protein comprising the amino acid sequence of amino acids 203-736 of SEQ ID NO:11, and a transfer genome comprising 5' to 3' following genetic elements: a 5' ITR element (e.g., the 5' ITR of SEQ ID NO: 8), a human HCR1 (e.g., the HCR1 of SEQ ID NO: 2), an hAAT promoter (e.g., the hAAT promoter of SEQ ID NO: 3), an SV40 intron (e.g., the SV40 intron of SEQ ID NO: 4), a silently altered human PAH coding sequence (e.g., the PAH coding sequence of SEQ ID NO: 1), an SV40 polyadenylation sequence (e.g., the SV40 polyadenylation sequence of SEQ ID NO: 6), and a 3' ITR element (e.g., the 3' ITR of SEQ ID NO: 9); (b) an AAV capsid protein comprising the amino acid sequence of amino acids 138-736 of SEQ ID NO:11, and a transfer genome comprising 5' to 3' following genetic elements: a 5' ITR element (e.g., the 5' ITR of SEQ ID NO: 8), a human HCR1 (e.g., the HCR1 of SEQ ID NO: 2), an hAAT promoter (e.g., the hAAT promoter of SEQ ID NO: 3), an SV40 intron (e.g., the SV40 intron of SEQ ID NO: 4), a silently altered human PAH coding sequence (e.g., the PAH coding sequence of SEQ ID NO: 1), an SV40 polyadenylation sequence (e.g., the SV40 polyadenylation sequence of SEQ ID NO: 6), and a 3' ITR element (e.g., the 3' ITR of SEQ ID NO: 9); and/or (c) an AAV capsid protein comprising the amino acid sequence of SEQ ID NO:11, and a transfer genome comprising 5' to 3' following genetic elements: a 5' ITR element (e.g., the 5' ITR of SEQ ID NO: 8), a human HCR1 (e.g., the HCR1 of SEQ ID NO: 2), an hAAT promoter (e.g., the hAAT promoter of SEQ ID NO: 3), an SV40 intron (e.g., the SV40 intron of SEQ ID NO: 4), a silently altered human PAH coding sequence (e.g., the PAH coding sequence of SEQ ID NO: 1), an SV40 polyadenylation sequence (e.g., the SV40 polyadenylation sequence of SEQ ID NO: 6), and a 3' ITR element (e.g., the 3' ITR of SEQ ID NO: 9).

In certain embodiments, the foregoing methods employ an rAAV comprising: (a) an AAV capsid protein comprising the amino acid sequence of amino acids 203-736 of SEQ ID NO:11, and a transfer genome comprising the nucleotide sequence set forth in any one of SEQ ID NOs: 7 or 10; (b) an AAV capsid protein comprising the amino acid sequence of amino acids 138-736 of SEQ ID NO:11, and a transfer genome comprising the nucleotide sequence set forth in any one of SEQ ID NOs: 7 or 10; and/or (c) an AAV capsid protein comprising the amino acid sequence of SEQ ID NO:11, and a transfer genome comprising the nucleotide sequence set forth in any one of SEQ ID NOs: 7 or 10.

The methods disclosed herein are particularly advantageous in that they are capable of expressing a PAH protein in a cell with high efficiency both in vivo and in vitro. In certain embodiments, the expression level of the PAH protein is at least 10%, 20%, 30%, 40%, 50%, 60%, 70%, 80%, 90%, or 100% of the expression level of the endogenous PAH protein in a cell of the same type that does not have a mutation in the PAH gene. In certain embodiments, the expression level of the PAH protein is at least 1.1, 1.2, 1.3, 1.4, 1.5, 1.6, 1.7, 1.8, 1.9, 2, 3, 4, 5, 6, 7, 8, 9, or 10 fold higher than the expression level of the endogenous PAH protein in a cell of the same type that does not have a mutation in the PAH gene. Any methods of determining the expression level of the PAH protein can be employed including, without limitation, ELISA, Western blotting, immunostaining, and mass spectrometry.

In certain embodiments, transduction of a cell with an AAV composition disclosed herein can be performed as provided herein or by any method of transduction known to one of ordinary skill in the art. In certain embodiments, the cell may be contacted with the AAV at a multiplicity of infection (MOI) of 50,000; 100,000; 150,000; 200,000; 250,000; 300,000; 350,000; 400,000; 450,000; or 500,000, or at any MOT that provides for optimal transduction of the cell.

An AAV composition disclosed herein can be administered to a subject by any appropriate route including, without limitation, intravenous, intraperitoneal, subcutaneous, intramuscular, intranasal, topical or intradermal routes. In certain embodiments, the composition is formulated for administration via intravenous injection or subcutaneous injection.

In another aspect, the instant disclosure provides methods of administering the rAAV as disclosed herein to a subject in need thereof. Any route of administration for delivering the rAAV to the subject effective for preventing, managing, treating, or diagnosing a disease or disorder associated with a PAH gene mutation can be used. Any effective amount of rAAV can be delivered to the subject effective for preventing, managing, treating, or diagnosing a disease or disorder associated with a PAH gene mutation. It is understood by those of skill in the art that the appropriate amount and route of administration of the rAAV may be decided by the attending medical professional (e.g., physician). Specific amounts of rAAV to be administered may depend on various factors, including without limitation, the age, sex, body weight, and general health of the subject, as well as other factors known to those of skill in the art.

In certain embodiments, the rAAV is administered as multiple doses. In certain embodiments, the rAAV is administered as one or more doses as part of a multiple dosage regime. In certain embodiments, the rAAV is administered as two, three, four, five, six, seven, eight, nine, ten, or more doses. In certain embodiments, the one or more doses make up a total dose that is sufficient to elicit a pharmaceutical effect (e.g., alleviate one or more symptoms of PKU).

In certain embodiments, the one or more doses are administered via a single route of administration (e.g., intravenously). In certain embodiments, the one or more doses are administered via multiple routes of administration. In certain embodiments, the one or more doses are administered via one, two, three, four, five, six, or more routes of administration.

In certain embodiments, the rAAV is administered as a single dose. In certain embodiments, the rAAV is administered at a dose of about 2e13 vg/kg to about 2e14 vg/kg (i.e., at about $2 \times 10^{13}$ vg/kg to about $2 \times 10^{14}$ vg/kg), wherein vg represents the number of viral genomes. In certain embodiments, the rAAV is administered at a dose of about 1e13 vg/kg to about 3e14 vg/kg. In certain embodiments, the rAAV is administered at a dose of about 1e13 vg/kg to about 3e13 vg/kg. In certain embodiments, the rAAV is administered at a dose of about 2e13 vg/kg to about 4e13 vg/kg. In certain embodiments, the rAAV is administered at a dose of about 3e13 vg/kg to about 5e13 vg/kg. In certain embodiments, the rAAV is administered at a dose of about 4e13 vg/kg to about 6e13 vg/kg. In certain embodiments, the rAAV is administered at a dose of about 5e13 vg/kg to about 7e13 vg/kg. In certain embodiments, the rAAV is administered at a dose of about 6e13 vg/kg to about 8e13 vg/kg. In certain embodiments, the rAAV is administered at a dose of about 7e13 vg/kg to about 9e13 vg/kg. In certain embodiments, the rAAV is administered at a dose of about 8e13 vg/kg to about 1e14 vg/kg. In certain embodiments, the rAAV is administered at a dose of about 9e13 vg/kg to about 1.21e14 vg/kg. In certain embodiments, the rAAV is administered at a dose of about 1e14 vg/kg to about 1.2e14 vg/kg. In certain embodiments, the rAAV is administered at a dose of about 1.1e14 vg/kg to about 1.3e14 vg/kg. In certain embodiments, the rAAV is administered at a dose of about 1.2e14 vg/kg to about 1.4e14 vg/kg. In certain embodiments, the rAAV is administered at a dose of about 1.3e14 vg/kg to about 1.5e14 vg/kg. In certain embodiments, the rAAV is administered at a dose of about 1.4e14 vg/kg to about 1.6e14 vg/kg. In certain embodiments, the rAAV is administered at a dose of about 1.5e14 vg/kg to about 1.7e14 vg/kg. In certain embodiments, the rAAV is administered at a dose of about 1.6e14 vg/kg to about 1.8e14 vg/kg. In certain embodiments, the rAAV is administered at a dose of about 1.7e14 vg/kg to about 1.9e14 vg/kg. In certain embodiments, the rAAV is administered at a dose of about 1.8e14 vg/kg to about 2e14 vg/kg. In certain embodiments, the rAAV is administered at a dose of about 1.9e14 vg/kg to about 2.1e14 vg/kg. In certain embodiments, the rAAV is administered at a dose of about 2e14 vg/kg to about 2.2e14 vg/kg. In certain embodiments, the rAAV is administered at a dose of about 2.1e14 vg/kg to about 2.3e14 vg/kg. In certain embodiments, the rAAV is administered at a dose of about 2.2e14 vg/kg to about 2.4e14 vg/kg. In certain embodiments, the rAAV is administered at a dose of about 2.3e14 vg/kg to about 2.5e14 vg/kg. In certain embodiments, the rAAV is administered at a dose of about 2.4e14 vg/kg to about 2.6e14 vg/kg. In certain embodiments, the rAAV is administered at a dose of about 2.5e14 vg/kg to about 2.7e14 vg/kg. In certain embodiments, the rAAV is administered at a dose of about 2.6e14 vg/kg to about 2.8e14 vg/kg. In certain embodiments, the rAAV is administered at a dose of about 2.7e14 vg/kg to about 2.9e14 vg/kg. In certain embodiments, the rAAV is administered at a dose of about 2.8e14 vg/kg to about 3e14 vg/kg.

In certain embodiments, the rAAV is administered at a dose of about 2e13 vg/kg, 3e13 vg/kg, 4e13 vg/kg, 5e13 vg/kg, 6e13 vg/kg, 7e13 vg/kg, 8e13 vg/kg, 9e13 vg/kg, 1e14 vg/kg, 1.1e14 vg/kg, 1.2e14 vg/kg, 1.3e14 vg/kg, 1.4e14 vg/kg, 1.5e14 vg/kg, 1.6e14 vg/kg, 1.7e14 vg/kg, 1.8e14 vg/kg, 1.9e14 vg/kg, or 2e14 vg/kg. In certain embodiments, the rAAV is administered at a dose of 2e13 vg/kg, 3e13 vg/kg, 4e13 vg/kg, 5e13 vg/kg, 6e13 vg/kg, 7e13 vg/kg, 8e13 vg/kg, 9e13 vg/kg, 1e14 vg/kg, 1.1e14 vg/kg, 1.2e14 vg/kg, 1.3e14 vg/kg, 1.4e14 vg/kg, 1.5e14 vg/kg, 1.6e14 vg/kg, 1.7e14 vg/kg, 1.8e14 vg/kg, 1.9e14 vg/kg, or 2e14 vg/kg.

In certain embodiments, the rAAV is administered at a dose of about 9e12 vg/kg, about 9.5e12 vg/kg, about 1e13 vg/kg, about 1.5e13 vg/kg, about 2e13 vg/kg, about 2.5e13 vg/kg, about 3e13 vg/kg, about 3.5e13 vg/kg, about 4e13 vg/kg, about 4.5e13 vg/kg, about 5e13 vg/kg, about 5.5e13 vg/kg, about 6e13 vg/kg, about 6.5e13 vg/kg, about 7e13 vg/kg, about 7.5e13 vg/kg, about 8e13 vg/kg, about 8.5e13 vg/kg, about 9e13 vg/kg, about 9.5e13 vg/kg, about 1e14 vg/kg, about 1.5e14 vg/kg, about 2e14 vg/kg, or about 2.5e14 vg/kg. In certain embodiments, the rAAV is administered at a dose of about 2e13 vg/kg. In certain embodiments, the rAAV is administered at a dose of about 1e13 vg/kg, about 1.2e13 vg/kg, about 1.4e13 vg/kg, about 1.6e13 vg/kg, about 1.8e13 vg/kg, about 2e13 vg/kg, about 2.2e13 vg/kg, about 2.4e13 vg/kg, about 2.6e13 vg/kg, about 2.8e13 vg/kg, or about 3e13 vg/kg. In certain embodiments, the rAAV is administered at a dose of about 6e13 vg/kg. In certain embodiments, the rAAV is administered at a dose of about 5e13 vg/kg, about 5.2e13 vg/kg, about 5.4e13 vg/kg, about 5.6e13 vg/kg, about 5.8e13 vg/kg, about 6e13 vg/kg, about 6.2e13 vg/kg, about 6.4e13 vg/kg, about 6.6e13 vg/kg, about 6.8e13 vg/kg, or about 7e13 vg/kg. In certain embodiments, the rAAV is administered at a dose of about 8e13 vg/kg. In certain embodiments, the rAAV is administered at a dose of about 7e13 vg/kg, about 7.2e13 vg/kg, about 7.4e13 vg/kg, about 7.6e13 vg/kg, about 7.8e13 vg/kg, about 8e13 vg/kg, about 8.2e13 vg/kg, about 8.4e13 vg/kg, about 8.6e13 vg/kg, about 8.8e13 vg/kg, or about 9e13 vg/kg. In certain embodiments, the rAAV is administered at a dose of about 1e14 vg/kg. In certain embodiments, the rAAV is administered at a dose of about 9e13 vg/kg, about 9.2e13 vg/kg, about 9.4e13 vg/kg, about 9.6e13 vg/kg, about 9.8e13 vg/kg, about 1e14 vg/kg, about 1.2e14 vg/kg, about 1.4e14 vg/kg, about 1.6e14 vg/kg, about 1.8e14 vg/kg, or about 2e14 vg/kg. In certain embodiments, the rAAV is administered at a dose of about 2e14 vg/kg. In certain embodiments, the rAAV is administered at a dose of about 1e14 vg/kg, about 1.2e14 vg/kg, about 1.4e14 vg/kg, about 1.6e14 vg/kg, about 1.8e14 vg/kg, about 2e14 vg/kg, about 2.2e14 vg/kg, about 2.4e14 vg/kg, about 2.6e14 vg/kg, about 2.8e14 vg/kg, or about 3e14 vg/kg.

In certain embodiments, administration of the rAAV as described herein to a subject in need thereof, results in minimal incidences of adverse events. In certain embodiments, administration of the rAAV to a subject in need thereof, results in minimal incidences of serious adverse events. In certain embodiments, the adverse events may be a result of the administration of the rAAV. Accordingly, in certain embodiments, administration of the rAAV to a subject in need thereof, results in minimal incidences of adverse events and/or serious adverse events that may be a result of the administration of the rAAV. In certain embodiments, administration of the rAAV to a subject in need thereof, results in a reduction of the incidence and severity of treatment emergent adverse events (TEAEs) and serious TEAEs.

In certain embodiments, administration of the rAAV as described herein to a subject in need thereof, alleviates one or more symptoms related to phenylketonuria (PKU). Symptoms of PKU may include, without limitation, a musty odor in the breath, skin, or urine; neurological symptoms that may include seizures; skin rashes (e.g., eczema); fair skin and blue eyes; abnormally small head (i.e., microencephaly); hyperactivity; intellectual disability; delayed development; behavioral, emotional, and social problems; and psychiatric disorders. Accordingly, in certain embodiments, administration of the rAAV as described herein to a subject in need thereof, alleviates one or more symptoms of PKU selected from the group consisting of a musty odor in the breath, skin, or urine; neurological symptoms that may include seizures; skin rashes (e.g., eczema); fair skin and blue eyes; abnormally small head (i.e., microencephaly); hyperactivity; intellectual disability; delayed development; behavioral, emotional, and social problems; and psychiatric disorders.

In certain embodiments, the normal range of blood phenylalanine (Phe) (e.g., plasma Phe) for a subject without hyperphenylalanemia (HPA; e.g., a subject that does not have a disease or disorder associated with a PAH gene mutation) is 58±14 μmon. In certain embodiments, a subject having a disease or disorder associated with a PAH gene mutation (e.g., PAH deficiency) that does not require treatment according to standard treatment guidelines available in the art, has a range of blood Phe (e.g., plasma Phe) between about 120 μmol/L to about 360 μmon (e.g., a blood Phe (e.g., plasma Phe) of about 100 μmon, about 110 μmon, about 120 μmol/L, about 130 μmol/L, about 140 μmol/L, about 150 μmol/L, about 160 μmon, about 170 μmol/L, about 180 μmol/L, about 190 μmol/L, about 200 μmol/L, about 210 μmon, about 220 μmol/L, about 230 μmol/L, about 240 μmol/L, about 250 μmol/L, about 260 μmon, about 270 μmol/L, about 280 μmol/L, about 290 μmol/L, about 300 μmol/L, about 310 μmon, about 320 μmon, about 330 μmon, about 340 μmon, about 350 μmon, about 360 μmon, about 370 μmol/L, about 380 μmol/L, about 390 μmon, or about 400 μmon. In certain embodiments, a subject having PAH deficiency (e.g., PKU) that does not require treatment according to standard treatment guidelines available in the art, has a range of blood Phe (e.g., plasma Phe) between about 120 μmol/L to about 360 μmol/L. In certain embodiments, a subject having PKU that does not require treatment according to standard treatment guidelines available in the art, has a range of blood Phe (e.g., plasma Phe) between about 120 μmol/L to about 360 μmol/L.

In certain embodiments, a subject having a disease or disorder associated with a PAH gene mutation (e.g. hyperphenylalanemia, PKU) suitable for treatment with an rAAV of the present disclosure has a blood Phe (e.g., plasma Phe) of greater than about 600 μmol/L. In certain embodiments, a suitable subject for treatment with an rAAV of the present disclosure has had two plasma Phe values with a concentration ≥600 μmol/L drawn at least 48 hours apart, and at least one historical value ≥600 μmol/L in the preceding 12 months. In certain embodiments, a subject having a disease or disorder associated with a PAH gene mutation (e.g. hyperphenylalanemia, PKU) suitable for treatment with an rAAV of the present disclosure has a blood Phe (e.g., plasma Phe) of greater than about 450 µmol/L, greater than about 500 µmol/L, greater than about 450 µmol/L, greater than about 600 µmol/L, greater than about 650 µmol/L, greater than about 700 µmol/L, greater than about 750 µmol/L, greater than about 800 µmol/L, greater than about 900 µmol/L, greater than about 1000 µmol/L, greater than about 1100 µmol/L, greater than about 1200 µmol/L, greater than about 1300 µmol/L, greater than about 1400 µmol/L, greater than about 1500 µmol/L, or more.

In certain embodiments, a subject suitable for employing a method of the present disclosure comprising administering an rAAV described herein, has been diagnosed with classic phenylketonuria (PKU) due to PAH deficiency. In certain embodiments, a subject suitable for employing a method of the present disclosure comprising administering an rAAV described herein, has two plasma Phe values with a concentration of greater than about 600 µmol/L drawn at least 48 hours apart and has at least one historical value greater than about 600 µmol/L in the preceding 12 months. In certain embodiments, a subject suitable for employing a method of the present disclosure comprising administering an rAAV described herein, is able to maintain a baseline diet (e.g., ±25% of average total protein intake (intact and medical), whether Phe-restricted or unrestricted) after employing the method of the present disclosure. In certain embodiments, if applicable, a subject suitable for employing a method of the present disclosure comprising administering an rAAV described herein, is able to maintain a stable dose of medication for attention-deficient/hyperactivity disorder (ADHD), depression, anxiety, or other psychiatric disorder for ±8 weeks prior to start of the method of the present disclosure, and is able to maintain stable dose throughout the treatment. In certain embodiments, a subject suitable for employing a method of the present disclosure comprising administering an rAAV described herein, if of childbearing potential, will use effective contraception for 12 months following employing the method of the present disclosure, including the use of barrier contraception during the 6 months following treatment.

In certain embodiments, a subject not suitable for employing a method of the present disclosure comprising administering an rAAV described herein, has PKU that is not due to PAH deficiency. In certain embodiments, a subject not suitable for employing a method of the present disclosure comprising administering an rAAV described herein, has detectable presence of an AAV neutralizing antibody directed against an AAV capsid protein as described herein. In certain embodiments, a subject not suitable for employing a method of the present disclosure comprising administering an rAAV described herein, has a history of or positive test result for human immunodeficiency virus (HIV). In certain embodiments, a subject not suitable for employing a method of the present disclosure comprising administering an rAAV described herein, has history of or positive test result for hepatitis C virus antibody or hepatitis B virus (defined as positive for both hepatitis B surface antigen and hepatitis B core antibody), or is undergoing antiviral therapy for hepatitis B or C. In certain embodiments, a subject not suitable for employing a method of the present disclosure comprising administering an rAAV described herein, has history of significant underlying liver disease, liver transplant, genetic liver disease, cirrhosis, NASH, or other liver condition. In certain embodiments, a subject not suitable for employing a method of the present disclosure comprising administering an rAAV described herein, has history of drug abuse or alcoholism that would limit the subject participating in the treatment. In certain embodiments, a subject not suitable for employing a method of the present disclosure comprising administering an rAAV described herein, has ALT ≥1.5× upper limit of normal (ULN) and AST ≥1.5×ULN. In certain embodiments, a subject not suitable for employing a method of the present disclosure comprising administering an rAAV described herein, has alkaline phosphatase value of ≥1.5× ULN. In certain embodiments, a subject not suitable for employing a method of the present disclosure comprising administering an rAAV described herein, has total bilirubin value of ≥1.5×ULN, and/or direct bilirubin value of ≥1.5× ULN. In certain embodiments, a subject not suitable for employing a method of the present disclosure comprising administering an rAAV described herein, has serum creatinine level of ≥1.5×ULN. In certain embodiments, a subject not suitable for employing a method of the present disclosure comprising administering an rAAV described herein, has hematology values outside the normal range (e.g., hemoglobin <11.0 g/dL for males or <10.0 g/dL for females; white blood cells <3,000/µL; absolute neutrophils <1,500/µL; platelets <100,000/µL). In certain embodiments, a subject not suitable for employing a method of the present disclosure comprising administering an rAAV described herein, has hemoglobin A1c value >7.9% or fasting glucose >200 mg/dL. In certain embodiments, a subject not suitable for employing a method of the present disclosure comprising administering an rAAV described herein, has a contraindication to steroid use or conditions that would worsen in the presence of corticosteroids. In certain embodiments, a subject not suitable for employing a method of the present disclosure comprising administering an rAAV described herein, has previously received gene therapy for the treatment of any condition. In certain embodiments, a subject not suitable for employing a method of the present disclosure comprising administering an rAAV described herein, has used in the past 30 days levodopa. In certain embodiments, a subject not suitable for employing a method of the present disclosure comprising administering an rAAV described herein, has presence of an untreated or inadequately treated active infection or an infection requiring systemic antiviral or antimicrobial therapy. In certain embodiments, a subject not suitable for employing a method of the present disclosure comprising administering an rAAV described herein, has used any medication that is intended to treat PKU, including the use of large neutral amino acids (LNAAs), within 30 days prior to start of treatment.

Accordingly, in certain embodiments, a method of the present disclosure comprising administering an rAAV described herein to a subject having a disease or disorder associated with a PAH gene mutation, at a dose described herein, may result in a reduction in plasma Phe concentration to less than about 360 µmol/L (e.g., less than about 340 µmol/L, less than about 320 µmol/L, less than about 300 µmol/L, less than about 280 µmol/L, less than about 260 µmol/L, less than about 240 µmol/L, less than about 220 µmol/L, less than about 200 µmol/L, less than about 180 µmol/L, less than about 160 µmol/L, less than about 140 µmol/L, or less than about 120 µmol/L). In certain embodiments, a method of the present disclosure comprising administering an rAAV described herein to a subject having a disease or disorder associated with a PAH gene mutation, at a dose described herein, may result in a reduction in plasma Phe concentration to less than about 120 µmol/L (e.g., less than about 110 µmol/L, less than about 100 µmol/L, less than about 90 µmol/L, less than about 80 µmol/L, less than about 70 µmol/L, less than about 60 µmol/L, less than about 50 µmol/L, less than about 40

µmol/L, less than about 30 µmol/L, less than about 20 µmol/L, or less than about 10 µmol/L.

In certain embodiments, the reduction in plasma Phe levels in a subject administered an rAAV as described herein may persist for at least 2 weeks, 4 weeks, 6 weeks, 8 weeks, 10 weeks, 3 months, 4 months, 5 months, 6 months, 7 months, 8 months, 9 months, months, 11 months, 12 months, 13 months, 14 months, 15 months, 16 months, 17 months, 18 months, 19 months, 20 months, 21 months, 22 months, 23 months, 2 years, 3 years, 4 years, years, 6 years, 7 years, 8 years, 9 years, 10 years, 15 years, or more than 15 years.

Immunosuppressant Regimens

In certain embodiments, liver-directed rAAV delivery to subjects may result in an immune response to the rAAV. In certain embodiments, the immune response to the rAAV is evidenced by an increase in liver function tests. Liver function tests include assaying the levels of certain enzymes and proteins in the blood. Various liver function tests are known in the art including, for example, assaying the level of alanine transaminase (ALT); aspartate transaminase (AST); alkaline phosphatase (ALP); albumin and total protein; bilirubin; gamma-glutamyltransferase (GGT); and L-lactate dehydrogenase (LD), and assaying the time it takes blood to clot (also known in the art as prothrombin time (PT)). In certain embodiments, the immune response to the rAAV is evidenced by an increase in AAV capsid-specific T cells in the peripheral blood. As known in the art, capsid-specific CD8+ T cell responses peak within 4-8 weeks and are coincident with elevations in serum ALT and AST and elimination of AAV-transduced cells. Further, humoral immunity to the AAV capsid has been shown to occur within 2-4 weeks of viral delivery. In certain embodiments, elevated transaminases (e.g., elevated levels of ALT and AST) are observed in subjects, and may be self-limited and unaccompanied by additional signs of liver toxicity. The elevation of transaminases (e.g., ALT and AST; known as transaminitis) can be controlled by the administration of anti-inflammatory and/or immunosuppressive therapies (e.g., an immunosuppressant regimen).

In certain embodiments, the subject is administered a prophylactic immunosuppressant regimen (e.g., a prophylactic prednisolone regimen) before administration of the rAAV of the present disclosure. In certain embodiments, the subject is administered a prophylactic immunosuppressant regimen one day before administration of the rAAV of the present disclosure. In certain embodiments, the subject is administered a prophylactic immunosuppressant regimen therapy during administration of the rAAV of the present disclosure. In certain embodiments, the subject is administered a prophylactic immunosuppressant regimen after administration of the rAAV of the present disclosure. In certain embodiments, the subject is administered a prophylactic immunosuppressant regimen before, during, and/or after administration of the rAAV of the present disclosure. A prophylactic immunosuppressant regimen described herein may limit the immunologic response in the liver and to maintain PAH expression and prevent loss of vector.

In certain embodiments, the duration and doses of the immunosuppressant regimen are intended to cover the anticipated period of peak immune response (e.g., about 8 weeks following viral delivery), followed by a gradual taper. It will be readily apparent to those of skill in the art (e.g., an attending physician) that administration of the immunosuppressant regimen, including gradual taper thereof, will depend on the general tolerability of the subject to the immunosuppressant regimen.

The route of administration of the immunosuppressant regimen will readily be able to be determined by those of skill in the art. In certain embodiments, the immunosuppressant regimen will be administered orally. In certain embodiments, the immunosuppressant regimen will be administered systemically (e.g., via intravenous or parenteral routes).

Suitable immunosuppressant regimens are known in the art and include use of corticosteroids. Accordingly, in certain embodiments, the subject is administered a corticosteroid (e.g., prednisolone) before, during, and/or after administration of the rAAV of the present disclosure. In certain embodiments, the corticosteroid is glucocorticoid. Examples of corticosteroids include, without limitation, hydrocortisone, cortisone, ethamethasoneb, prednisone, prednisolone, triamcinolone, methylprednisolone, and dexamathasone. In certain embodiments, the subject is administered prednisolone before, during, and/or after administration of the rAAV of the present disclosure.

In certain embodiments, the immunosuppressant regimen (e.g., prednisolone regimen) is administered to the subject before administration of the rAAV of the present disclosure. In certain embodiments, the immunosuppressant regimen (e.g., prednisolone regimen) is administered to the subject at least one day, at least two days, at least three days, at least four days, at least five days, at least six days, at least seven days, at least eight days, at least nine days, or at least ten days, before administration of the rAAV of the present disclosure. In certain embodiments, the immunosuppressant regimen (e.g., prednisolone regimen) is administered to the subject one day before administration of the rAAV of the present disclosure.

In certain embodiments, the immunosuppressant regimen (e.g., prednisolone regimen) is administered to the subject for about 20 or about 21 weeks. In certain embodiments, the immunosuppressant regimen (e.g., prednisolone regimen) is administered to the subject for at least about one week, at least about two weeks, at least about three weeks, at least about four weeks, at least about five weeks, at least about six weeks, at least about seven weeks, at least about eight weeks, at least about nine weeks, at least about ten weeks, at least about eleven weeks, at least about twelve weeks, at least about thirteen weeks, at least about fourteen weeks, at least about fifteen weeks, at least about sixteen weeks, at least about seventeen weeks, at least about eighteen weeks, at least about nineteen weeks, at least about twenty weeks, at least about twenty one weeks, or at least about twenty two weeks. It will be appreciated by those of skill in the art that the duration of the immunosuppressant regimen described herein may depend on the tolerability of the subject to the therapy, and or depend on clinical developments during the course of the therapy. For example, in certain embodiments, if at any time during the immunosuppressant regimen, the subject exhibits an abnormal result of a liver function test (e.g., exhibits an abnormal serum level of one or more liver enzymes), the immunosuppressant regimen may be restarted and/or modified to include additional doses for additional durations. In such embodiments the duration of the immunosuppressant regimen will be prolonged, e.g., beyond the about 20 week duration.

In certain embodiments, the immunosuppressant regimen (e.g., prednisolone regimen) is administered at doses described in prednisolone equivalents. As used herein, the term "prednisolone equivalent" refers to a dose of a corticosteroid that results in substantially the same effect as the effect of a certain dose of prednisolone (e.g., immunosuppressive effect of a certain dose of prednisolone) when administered to a subject. For example, a 5 mg dose of prednisolone is known in the art to elicit substantially the same effect as 0.75 mg of dexamethasone when administered to a subject. As such, a 5 mg dose in prednisolone equivalents is readily understood by those of skill in the art to encompass a 5 mg dose of prednisolone, or a 0.75 mg dose of dexamethasone. Corticosteroid equivalency conversion tables are available to and accessible by those of skill in the art and can be readily accessed from, for example, a clinical decision support resource such as UpToDate. In certain embodiments, the duration and doses of the immunosuppressant regimen are calculated according to the corticosteroid equivalency conversion values as shown in Table 1.

TABLE 1

Corticosteroid Equivalent Doses

| Corticosteroid | Equivalent dose (mg) |
| --- | --- |
| Hydrocortisone (cortisol) | 20 |
| Cortisone acetate | 25 |
| Prednisone | 5 |
| Prednisolone | 5 |
| Methylprednisolone | 4 |
| Triamcinolone | 4 |
| Dexamethasone | 0.75 |
| Betamethasone | 0.6 |

In certain embodiments, the immunosuppressant regimen (e.g., prednisolone regimen) is administered at a certain dose per day. For example, the therapy can comprise a dose in mg per day. In certain embodiments, the immunosuppressant regimen (e.g., prednisolone or dexamethasone regimen) is administered according to a weight-based dose, e.g., at a certain dose according to the weight of a subject, per day. For example, the therapy can comprise a dose in mg per kg of a subject per day.

In certain embodiments, the immunosuppressant regimen (e.g., prednisolone regimen) is administered at about 1 mg/day to about 100 mg/day. In certain embodiments, the immunosuppressant regimen (e.g., prednisolone regimen) is administered at about 1 mg/day to about 100 mg/day in prednisolone equivalents. In certain embodiments, the immunosuppressant regimen (e.g., prednisolone regimen) is administered at about 1 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 55 mg/day, about 60 mg/day, about 65 mg/day, about 70 mg/day, about 75 mg/day, about 80 mg/day, about 85 mg/day, about 90 mg/day, about 95 mg/day, or about 100 mg/day. In certain embodiments, the immunosuppressant regimen (e.g., prednisolone regimen) is administered at about 1 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 55 mg/day, about 60 mg/day, about 65 mg/day, about 70 mg/day, about 75 mg/day, about 80 mg/day, about 85 mg/day, about 90 mg/day, about 95 mg/day, or about 100 mg/day in prednisolone equivalents.

In certain embodiments, specific doses of the immunosuppressant regimen are administered according to a sequential dosing regimen. In certain embodiments, the immunosuppressant regimen is administered according to a sequential dosing regimen. In certain embodiments, the immunosuppressant regimen is administered according to the following sequential dosing regimen: about 60 mg/day in prednisolone equivalents for about two weeks; about 40 mg/day in prednisolone equivalents for about six weeks; about 30 mg/day in prednisolone equivalents for about three weeks; about 20 mg/day in prednisolone equivalents for about three weeks; about 10 mg/day in prednisolone equivalents for about five weeks; and about 5 mg/day in prednisolone equivalents for about one week. In certain embodiments, the final step of about 5 mg/day in prednisolone equivalents for about one week may be continued for a total of about two weeks. In certain embodiments, specific doses of the immunosuppressant regimen are administered according to a sequential dosing regimen. In certain embodiments, the prednisolone is administered according to a sequential dosing regimen. In certain embodiments, the prednisolone is administered according to the following sequential dosing regimen: about 60 mg/day for about two weeks; about 40 mg/day for about six weeks; about 30 mg/day for about three weeks; about 20 mg/day for about three weeks; about 10 mg/day for about five weeks; and about 5 mg/day for about one week. In certain embodiments, the final step of about 5 mg/day for about one week may be continued for a total of about two weeks.

In certain embodiments, a subject experiences elevated AST and/or ALT levels greater than 2 times the upper limit of normal (ULN) during the prophylactic immunosuppressant regimen described herein. In such embodiments, the immunosuppressant regimen will be re-escalated or re-started at a certain dose.

Accordingly, in certain embodiments, where a subject experiences elevated levels of AST and/or ALT greater than 2 times the upper limit of normal (ULN) during a prophylactic prednisolone sequential dosing regimen, for example, about 60 mg/day for two weeks; about 40 mg/day for six weeks; about 30 mg/day for three weeks; about 20 mg/day for three weeks; about 10 mg/day for five weeks; and about 5 mg/day for one or two weeks, the prednisolone will be re-escalated or re-started at 60 mg/day, and then tapered again, according to the same sequential dosing regimen, e.g., about 60 mg/day for two weeks; about 40 mg/day for six weeks; about 30 mg/day for three weeks; about 20 mg/day for three weeks; about 10 mg/day for five weeks; and about 5 mg/day for one or two weeks.

In certain embodiments, a subject experiences elevated levels of AST and/or ALT greater than 2 times the upper limit of normal following the end of a prophylactic immunosuppressant regimen described herein. In such embodiments, the immunosuppressant regimen will be re-started according to a modified regimen.

Accordingly, in certain embodiments, where a subject experiences elevated levels of AST and/or ALT greater than 2 times the upper limit of normal (ULN) following the end of a prophylactic prednisolone sequential dosing regimen, for example, about 60 mg/day for two weeks; about 40 mg/day for six weeks; about 30 mg/day for three weeks; about 20 mg/day for three weeks; about 10 mg/day for five weeks; and about 5 mg/day for one or two weeks, the prednisolone will be re-started according to the following dosing regimen: about 60 mg/day for two weeks or until ALT and/or AST levels have declined to below or about the subject's baseline levels; about 40 mg/day for two weeks; about 30 mg/day for two weeks; about 20 mg/day for two weeks; about 10 mg/day for two weeks; and about 5 mg/day for two weeks. In certain embodiments, the taper below the about 60 mg/day prednisolone for two weeks does not start until the ALT and/or AST levels have declined to the subject's baseline levels, provided that the subject tolerates the regimen. In certain embodiments, the duration of the about 60 mg/day prednisolone dose does not exceed four weeks. In certain embodiments, where ALT and/or AST levels continue to rise at 60 mg/day or 40 mg/day, intravenous methylprednisolone may be administered.

Other Concomitant Therapy

In certain embodiments, subjects will continue their usual dietary regimen. In certain embodiments, the baseline diet will be established, and may be defined as ±25% of average total protein intake (intact and medical), whether Phe-restricted or unrestricted. In certain embodiments, the baseline diet will be maintained following administration of the rAAV of the present disclosure. In certain embodiments, modification of the diet may be made based on: (1) at 8 weeks, if three Phe values during the first 8 weeks are ≤360 µmol/L; and/or (2) prior to 8 weeks, if three Phe values during the first 8 weeks (measured at least one week apart) are <120 µmol/L.

In certain embodiments, subjects taking medications for the treatment of ADHD, depression, anxiety, or other psychiatric disorders at study entry must be on a stable dose for ≥8 weeks prior to administration of the rAAV of the present disclosure, and may continue with the same dose regimen throughout the study, unless otherwise determined by a physician for medical reasons.

In certain embodiments, use of any medications for PKU, including Kuvan®, LNAA, and Palynzig™, may be prohibited unless the plasma Phe concentration is considered to be unsafe for the subject, and it is determined that such treatment is medically necessary following modification of diet.

IV. Systems and Methods for Making rAAV

The rAAV used in the methods disclosed herein can be produced using any art recognized method. Packaging systems useful for the production of rAAV are described below. Methods for using such packaging systems are well known in the art.

In certain embodiments, packaging systems useful for producing rAAV comprise: first nucleotide encoding one or more AAV Rep proteins; a second nucleotide encoding a capsid protein of any of the AAVs as disclosed herein; and a third nucleotide sequence comprising any of the rAAV genome sequences as disclosed herein, wherein the packaging system is operative in a cell for enclosing the transfer genome in the capsid to form the AAV. In certain embodiments, the packaging system comprises a first vector comprising the first nucleotide sequence encoding the one or more AAV Rep proteins and the second nucleotide sequence encoding the AAV capsid protein, and a second vector comprising the third nucleotide sequence comprising the rAAV genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.).

Any AAV Rep protein can be employed in the packaging systems disclosed herein. In certain embodiments of the packaging system, the Rep nucleotide sequence encodes an AAV2 Rep protein. Suitable AAV2 Rep proteins may include, without limitation, Rep 78/68 or Rep 68/52. In certain embodiments of the packaging system, the nucleotide sequence encoding the AAV2 Rep protein comprises a nucleotide sequence that encodes a protein having a minimum percent sequence identity to the AAV2 Rep amino acid sequence of SEQ ID NO: 22, wherein the minimum percent sequence identity is at least 70% (e.g., at least 75%, at least 80%, at least 85%, at least 90%, at least 95%, at least 98%, at least 99%, or 100%) across the length of the amino acid sequence of the AAV2 Rep protein. In certain embodiments of the packaging system, the AAV2 Rep protein has the amino acid sequence set forth in SEQ ID NO: 22.

In certain embodiments of the packaging system, the packaging system further comprises a forth nucleotide sequence comprising one or more helper virus genes. In certain embodiments, the forth nucleotide sequence comprises adenoviral E2, E4 and VA genes. In certain embodiments of the packaging system, the packaging system further comprises a third vector (e.g., a helper virus vector), comprising the forth nucleotide sequence. The third vector may be an independent third vector, integral with the first vector, or integral with the second vector.

In certain embodiments of the packaging system, the helper virus is selected from the group consisting of adenovirus, herpes virus (including herpes simplex virus (HSV)), poxvirus (such as vaccinia virus), cytomegalovirus (CMV), and baculovirus. In certain embodiments of the packaging system, where the helper virus is adenovirus, the adenovirus genome comprises one or more adenovirus RNA genes selected from the group consisting of E1, E2, E4 and VA. In certain embodiments of the packaging system, where the adenovirus genome comprises one or more adenovirus RNA genes selected from the group consisting of E2, E4 and VA. In certain embodiments of the packaging system, where the helper virus is HSV, the HSV genome comprises one or more of HSV genes selected from the group consisting of UL5/8/52, ICP0, ICP4, ICP22 and UL30/UL42.

In certain embodiments of the packaging system, the first, second, and/or third vector are contained within one or more plasmids. In certain embodiments, the first vector and the third vector are contained within a first plasmid. In certain embodiments the second vector and the third vector are contained within a second plasmid.

In certain embodiments of the packaging system, the first, second, and/or third vector are contained within one or more recombinant helper viruses. In certain embodiments, the first vector and the third vector are contained within a recombinant helper virus. In certain embodiments, the second vector and the third vector are contained within a recombinant helper virus.

In certain embodiments of the packaging system comprises: a first nucleotide sequence encoding one or more AAV Rep proteins; a second nucleotide sequence encoding a capsid protein of any one of the AAVs described herein; a third nucleotide sequence comprising an rAAV genome sequence of any one of the AAVs described herein; and optionally a forth nucleotide sequence comprising one or more helper virus genes (e.g., adenoviral E2, E4 and VA genes).

In certain embodiments, rAAV can be produced using a method that comprises transfecting or transducing a cell with a packaging system as described herein under conditions operative for enclosing the rAAV genome in an AAV capsid to form a rAAV. Exemplary methods for recombinant preparation of an rAAV include transient transfection (e.g., with one or more transfection plasmids containing a first, and a second, and optionally a third vector as described herein), viral infection (e.g. with one or more recombinant helper viruses, such as a adenovirus, poxvirus (such as vaccinia virus), herpes virus (including HSV, cytomegalovirus, or baculovirus, containing a first, and a second, and optionally a third vector as described herein), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more capsid proteins as described herein, and with a transfer genome as described herein being delivered in the form of a plasmid or a recombinant helper virus).

V. Additional Embodiments

The present disclosure is also described by the following embodiments.

Embodiment 1. A method for treating a subject having a disease or disorder associated with a PAH gene mutation, the method comprising administering to the subject an rAAV at a dose of about 2e13 vg/kg to about 2e14 kg/vg, wherein the rAAV comprises: (a) an AAV capsid comprising a capsid protein; and (b) a transfer genome comprising a silently altered PAH coding sequence, wherein the silently altered PAH coding sequence comprises the nucleotide sequence set forth in SEQ ID NO:1.

Embodiment 2. The method of Embodiment 1, wherein the transfer genome further comprises a transcriptional regulatory element operably linked to the silently altered PAH coding sequence.

Embodiment 3. The method of Embodiment 2, wherein the transcriptional regulatory element is capable of mediating transcription in a hepatocyte, a renal cell, or a cell in the brain, pituitary gland, adrenal gland, pancreas, urinary bladder, gallbladder, colon, small intestine, or breast.

Embodiment 4. The method of Embodiment 2, wherein the transcriptional regulatory element comprises a human hepatic control region 1 (HCR1) comprising the nucleotide sequence set forth in SEQ ID NO:2.

Embodiment 5. The method of Embodiment 2, wherein the transcriptional regulatory element comprises a human al-antitrypsin (hAAT) promoter comprising the nucleotide sequence set forth in SEQ ID NO:3.

Embodiment 6. The method of Embodiment 2, wherein the transcriptional regulatory element comprises an SV40 intron comprising the nucleotide sequence set forth in SEQ ID NO:4.

Embodiment 7. The method of Embodiment 2, wherein the transcriptional regulatory element comprises the nucleotide sequence set forth in SEQ ID NO:5.

Embodiment 8. The method of any one of the preceding Embodiments, wherein the transfer genome further comprises an SV40 polyadenylation sequence 3' to the PAH coding sequence, wherein the SV40 polyadenylation sequence comprises the nucleotide sequence set forth in SEQ ID NO:6.

Embodiment 9. The method of any one of the preceding Embodiments, wherein the transfer genome comprises the nucleotide sequence set forth in SEQ ID NO:7.

Embodiment 10. The method of any one of the preceding Embodiments, wherein the transfer genome further comprises a 5' inverted terminal repeat (5' ITR) nucleotide sequence 5' of the genome, and a 3' inverted terminal repeat (3' ITR) nucleotide sequence 3' of the genome.

Embodiment 11. The method of Embodiment 10, wherein the 5' ITR nucleotide sequence has at least 95% sequence identity to SEQ ID NO:8, and the 3' ITR nucleotide sequence has at least 95% sequence identity to SEQ ID NO:9.

Embodiment 12. The method of any one of the preceding Embodiments, wherein the transfer genome comprises the nucleotide sequence set forth in SEQ ID NO:10.

Embodiment 13. The method of any one of the preceding Embodiments, wherein the AAV capsid comprises: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R.

Embodiment 14. The method of any one of the preceding Embodiments, wherein the AAV capsid comprises: a capsid protein comprising an amino acid sequence having at least 99% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 99% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 99% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R.

Embodiment 15. The method of any one of the preceding Embodiments, wherein the AAV capsid comprises a capsid protein comprising the amino acid sequence of amino acids 203-736 of SEQ ID NO:11, a capsid protein comprising the amino acid sequence of amino acids 138-736 of SEQ ID NO:11, and/or a capsid protein comprising the amino acid sequence of amino acids 1-736 of SEQ ID NO:11.

Embodiment 16. The method of any one of the preceding Embodiments, wherein the amino acid sequence of the capsid protein consists of the amino acid sequence of amino acids 203-736 of SEQ ID NO:11, the amino acid sequence of the capsid protein consists of the amino acid sequence of amino acids 138-736 of SEQ ID NO:11, and/or the amino acid sequence of the capsid protein consists of the amino acid sequence of amino acids 1-736 of SEQ ID NO:11.

Embodiment 17. A method for treating a subject having a disease or disorder associated with a PAH gene mutation, the method comprising administering to the subject an rAAV at a dose of about 2e13 vg/kg to about 2e14 kg/vg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

Embodiment 18. The method of Embodiment 17, wherein the AAV capsid comprises: a capsid protein comprising an amino acid sequence having at least 99% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 99% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 99% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R.

Embodiment 19. The method of Embodiment 17, wherein the AAV capsid comprises: a capsid protein comprising the amino acid sequence of amino acids 203-736 of SEQ ID NO:11; a capsid protein comprising the amino acid sequence of amino acids 138-736 of SEQ ID NO:11; and/or a capsid protein comprising the amino acid sequence of amino acids 1-736 of SEQ ID NO:11.

Embodiment 20. The method of Embodiment 17, wherein: the amino acid sequence of the capsid protein consists of the amino acid sequence of amino acids 203-736 of SEQ ID NO:11; the amino acid sequence of the capsid protein consists of the amino acid sequence of amino acids 138-736 of SEQ ID NO:11; and/or the amino acid sequence of the capsid protein consists of the amino acid sequence of amino acids 1-736 of SEQ ID NO:11.

Embodiment 21. The method of any one of the preceding Embodiments, wherein the dose is about 2e13 vg/kg.

Embodiment 22. The method of any one of the preceding Embodiments, wherein the dose is about 6e13 vg/kg.

Embodiment 23. The method of any one of the preceding Embodiments, wherein the dose is about 8e13 vg/kg.

Embodiment 24. The method of any one of the preceding Embodiments, wherein the dose is about 1e14 vg/kg.

Embodiment 25. The method of any one of the preceding Embodiments, wherein the dose is about 2e14 vg/kg.

Embodiment 26. The method of any one of the preceding Embodiments, wherein the rAAV is administered as a single dose.

Embodiment 27. The method of any one of Embodiments 1 to 25, wherein the rAAV is administered as multiple doses.

Embodiment 28. The method of any one of the preceding Embodiments, wherein the rAAV is administered intravenously.

Embodiment 29. The method of any one of the preceding Embodiments, wherein the subject is a pediatric subject.

Embodiment 30. The method of any one of Embodiments 1 to 28, wherein the subject is an adult subject.

Embodiment 31. The method of any one of the preceding Embodiments, wherein the subject is administered a prophylactic anti-inflammation therapy before, during, and/or after administration of the rAAV.

Embodiment 32. The method of Embodiment 31, wherein the prophylactic anti-inflammation therapy is administered to the subject before administration of the rAAV, optionally 1, 2, 3, 4, 5, 6, 7, 8, 9, or 10 days before administration of the rAAV.

Embodiment 33. The method of Embodiment 31, wherein the prophylactic anti-inflammation therapy is administered to the subject for at least 1, 2, 3, 4, 5, 6, 7, 8, 9, 10, 11, 12, 13, 14, 15, 16, 17, 18, 19 or 20 weeks.

Embodiment 34. The method of any one of Embodiments 31 to 33, wherein the anti-inflammation therapy is a glucocorticosteroid.

Embodiment 35. The method of Embodiment 34, wherein the glucocorticosteroid is prednisolone.

Embodiment 36. The method of Embodiment 35, wherein the prednisolone is administered at about 1 to about 100 mg/day, optionally, about 5, 10, 15, 20, 25, 30, 35, 40, 45, 50, 55, 60, 65, 70, 75, 80, 85, 90, 95, or 100 mg/day.

Embodiment 37. The method of Embodiment 35, wherein the prednisolone is administered according to the following sequential dosing regimen: 60 mg/day for two weeks; 40 mg/day for six weeks; 30 mg/day for three weeks; 20 mg/day for three weeks; 10 mg/day for five weeks; and 5 mg/day for one week.

Embodiment 38. The method of any one of the preceding Embodiments, wherein the disease or disorder associated with a PAH gene mutation is phenylketonuria (PKU).

Embodiment 39. A method for treating a subject having a disease or disorder associated with a PAH gene mutation, the method comprising intravenously administering to the subject an rAAV at a dose of about 2e13 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

Embodiment 40. A method for treating a subject having a disease or disorder associated with a PAH gene mutation, the method comprising intravenously administering to the subject an rAAV at a dose of about 6e13 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

Embodiment 41. A method for treating a subject having a disease or disorder associated with a PAH gene mutation, the method comprising intravenously administering to the subject an rAAV at a dose of about 8e13 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

Embodiment 42. A method for treating a subject having a disease or disorder associated with a PAH gene mutation, the method comprising administering to the subject an rAAV at a dose of about 1e14 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

Embodiment 43. A method for treating a subject having a disease or disorder associated with a PAH gene mutation, the method comprising administering to the subject an rAAV at a dose of about 2e14 vg/kg, wherein the rAAV comprises: (a) an AAV capsid comprising: a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and (b) a transfer genome comprising the nucleotide sequence set forth in SEQ ID NO:7 or SEQ ID NO:10.

VI. Examples

The following examples are offered by way of illustration, and not by way of limitation.

Example 1: Human PAH Transfer Vector

The AAV gene transfer vector pHMI-hPAH-TC-025, as shown in FIG. 1, comprises 5' to 3' the following genetic elements: a truncated 5' ITR element, a human hepatic control region 1 (HCR1), a human a1-antitrypsin (hAAT) promoter, an SV40 intron, a silently altered human PAH coding sequence, an SV40 polyadenylation sequence, and a modified 3' ITR element. The sequences of these elements are set forth in Table 2. The truncated 5' ITR allows the vector to form a double-stranded AAV genome after transduction into cells. This vector is capable of expressing a human PAH protein in a human hepatocyte.

TABLE 2

Genetic elements in human PAH transfer vector pHMI-hPAH-TC-025

| Genetic Element | SEQ ID NO |
| --- | --- |
| truncated 5' ITR element | 8 |
| human HCR1 | 2 |
| human α1-antitrypsin (hAAT) promoter | 3 |
| SV40 intron | 4 |
| transcriptional regulatory region comprising the human HCR1 and hAAT promoter | 5 |
| codon-altered human PAH coding sequence | 1 |
| SV40 polyadenylation sequence | 6 |
| modified 3' ITR element | 9 |
| Transfer genome (from HCR1 to polyadenylation sequence) | 7 |
| Transfer genome (from 5' ITR to 3' ITR) | 10 |
| Full sequence of transfer vector | 23 |

Example 2: Efficacy of a PAH Transfer Vector in a Mouse Model of PKU $Pah^{-/-}$ ($PAH^{enu2}$) mice were housed in clear polycarbonate cages with contact bedding in an isolator. Picolab Mouse Diet 5058 was provided to the animals ad libitum. Spring or tap water acidified with 1N HCl to a targeted pH of 2.5-3.0 was provided ad libitum. Vectors packaged in AAVHSC15 capsid were prepared in PBS (with Ca and Mg), supplemented with 35 mM NaCl, 1% sucrose, and 0.05% Pluronic F-68. The formulation was injected intravenously via the tail vein.

Blood samples were collected every week after the administration of the PAH transfer vector (0 week: prior to administration) by facial vein puncture or tail snip. The samples were allowed to clot at room temperature for at least 30 minutes, centrifuged at ambient temperature at minimum 1000×g for 10 minutes and the serum samples were extracted. Serum samples were stored at −70° C. Serum phenylalanine and tyrosine levels were measured by tandem mass spectrometry.

For collection of tissue samples, the animals underwent cardiac perfusion with saline. Liver (caudate lobe), kidney (left), brain, heart, and muscle (quadriceps) tissues were snap frozen in liquid nitrogen and stored at −70° C. The snap frozen tissues were ground into powder in liquid nitrogen in a mortar and pestle and divided in to aliquots to test for PAH expression for vector genome biodistribution by qPCR.

Figure 2A:
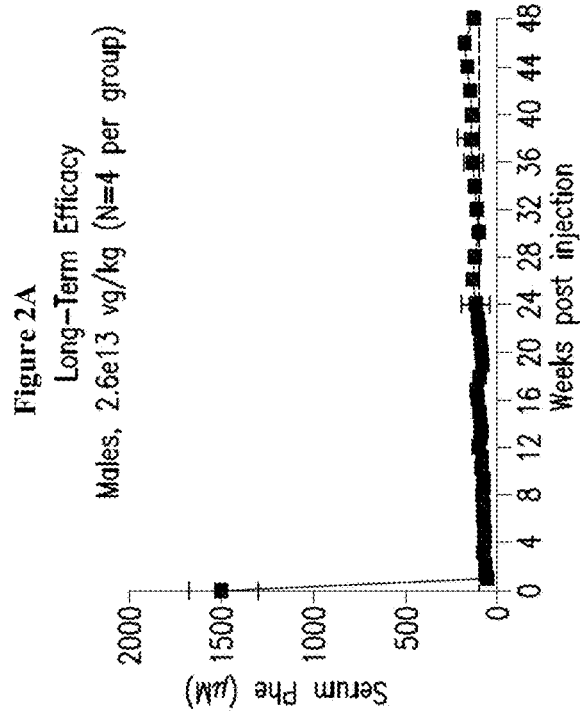
FIGS. 2A-2B are graphs showing the levels of phenylalanine over time in the serum of male (FIG. 2A) or female (FIG. 2B) mice administered the indicated doses of an rAAV comprising the pHMI-hPAH-TC-025 vector.
Figure 2B:
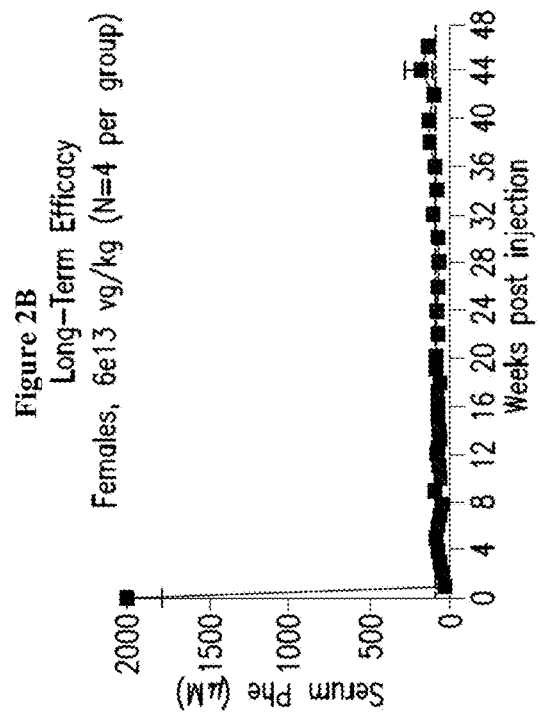
Figure 3C:
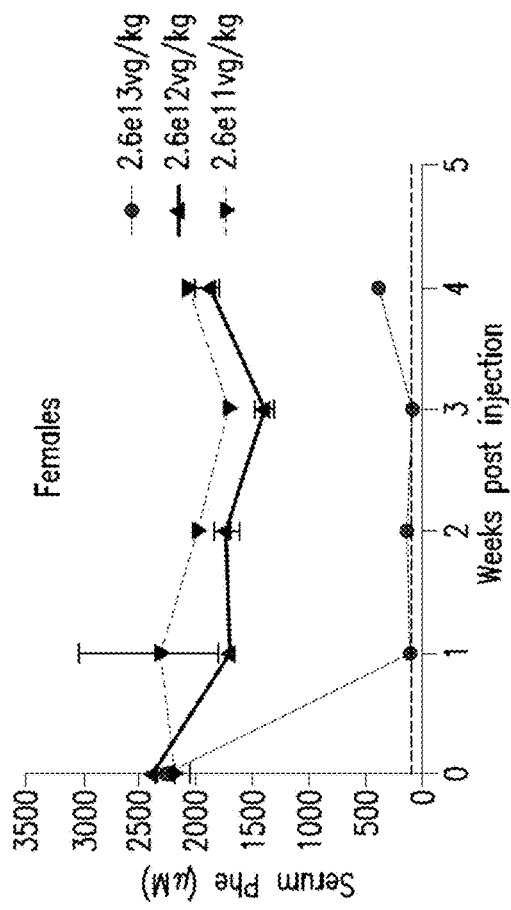
Figure 3D:
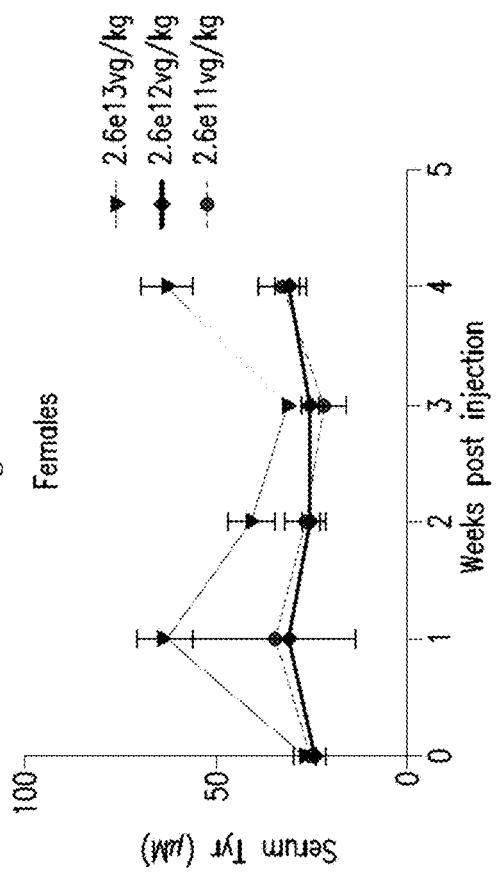

To examine the long-term efficacy of an rAAV comprising pHMI-hPAH-TC-025 packaged in AAVHSC15 capsid, a single dose of 2.6×10 13 vector genomes per kg of body weight was administered to male $Pah^{-/-}$ ($PAH^{enu2}$) mice, and a single dose of $6×10^{13}$ vector genomes per kg of body weight was administered to female $Pah^{-/-}$ ($PAH^{enu2}$) mice. As shown in FIGS. 2A and 2B, the administration of the pHMI-hPAH-TC-025-containing rAAV led to significant reduction of Phe levels within one week. This reduction persisted for at least 48 weeks in male mice, and at least 46 weeks in female mice. An increase of PAH mRNA was observed by ddPCR in the liver samples of these mice collected 4 weeks post injection relative to the mice not administered the rAAV vector. An increase of the PAH enzymatic activity was also detected in liver samples by mass spectrometry.

The efficacy of different doses of the pHMI-hPAH-TC-025-containing rAAV described above was further assessed. A single dose of $2.6×10^{11}$, $2.6×10^{12}$, or $2.6×10^{13}$ vector genomes per kg of body weight was administered to male mice and female $Pah^{-/-}$ ($PAH^{enu2}$) mice, and the serum levels of Phe and Tyr were measured. As shown in FIGS. 3A-3D, the dose of $2.6×10^{13}$ vector genomes per kg of body weight reduced the Phe levels and increased the Tyr levels more significantly than the two lower doses, and maintained complete reduction of serum Phe levels during the time examined in both male and female subjects.

Example 3: Clinical Study of a PAH Transfer Vector

This example describes the protocol for a Phase 1/2, randomized, concurrently-controlled, dose escalation study to evaluate the safety and efficacy of a rAAV comprising the pHMI-hPAH-TC-025 vector packaged in AAVHSC15 capsid, in adult phenylketonuria (PKU) subjects with PAH deficiency.

Subjects will undergo screening assessments prior to study entry, with the screening period lasting up to 45 days. Prior to administration of pHMI-hPAH-TC-025 vector packaged in AAVHSC15 capsid, subjects will be admitted to the clinical research unit and prophylactic steroid administration will be initiated. One approximately 120-minute administration of pHMI-hPAH-TC-025 vector packaged in AAVHSC15 capsid will occur in a clinical research unit setting. Subjects may be discharged home after they have been observed for at least 24 hours in the clinical research unit following administration of pHMI-hPAH-TC-025 vector packaged in AAVHSC15 capsid, provided they are clinically stable. Subjects will continue their usual dietary regimen (either Phe-restricted or unrestricted diet) during the screening period and following administration of pHMI-hPAH-TC-025 vector packaged in AAVHSC15 capsid.

Subjects will undergo safety and efficacy observation for 52 weeks in this study following administration of pHMI-hPAH-TC-025 vector packaged in AAVHSC15 capsid. Up to three dose levels of pHMI-hPAH-TC-025 vector packaged in AAVHSC15 capsid will be investigated. All doses are anticipated to provide a clinically relevant decrease in plasma Phe concentration. At a given dose level, 2 subjects will be enrolled and dosed initially. Dosing of the first 2 subjects in each cohort will be staggered, with at least a 21-day interval between dosing of each subject. At least 21-day safety follow-up and Phe concentration data for each subject will be reviewed before the subsequent subject is dosed in that cohort.

Following evaluation of at least 21 days of data from the first 2 subjects in a cohort, a decision can be made to either: (1) escalate to the next dose level, (2) addone additional subject to the same cohort, or (3) expand the cohort at the selected dose to enroll up to 9 additional subjects. 6 subjects will be randomized to receive pHMI-hPAH-TC-025 vector packaged in AAVHSC15 capsid and 3 subjects will be randomized to a concurrent delayed treatment control arm.

Decisions regarding dose escalation and expansion will be based on safety and changes in plasma Phe concentrations relative to the treatment guidelines for PKU. Treatment guidelines describe the range of 120-360 μmol/L as PAH deficiency not requiring treatment, and the normal range of blood Phe (e.g., plasma Phe) for an individual without hyperphenylalaninemia (HPA) or PKU as 58±14 (SD) μmol/L.

Inclusion and Exclusion Criteria

Suitable subjects for the study will be enrolled according to the inclusion and exclusion criteria set forth in Table 3.

TABLE 3

Inclusion and Exclusion Criteria

Inclusion Criteria:

Subject is able to understand the purpose and risks of the study, is willing to provide informed consent, and is able to comply with all study procedures and 4-year long-term follow up.
Adults 18-55 years of age at the time of informed consent.
Diagnosis of classic PKU (due to PAH deficiency).
Two plasma Phe values with a concentration of ≥600 μmol/L drawn at least 48 hours apart during the screening period and at least one historical value ≥600 μmol/L in the preceding 12 months.
Subject has the ability and willingness to maintain their baseline diet (±25% of average total protein intake (intact and medical), whether Phe-restricted or unrestricted, as established during the 45-day screening period) after administration of pHMI-hPAH-TC-025 vector packaged in AAVHSC15 capsid, unless otherwise directed.
If applicable, ability to maintain stable dose of medication for attention-deficit/hyperactivity disorder (ADHD), depression, anxiety, or other psychiatric disorder for >8 weeks prior to enrollment and willing to maintain stable dose throughout study unless a change is medically indicated.
Males and Females of childbearing potential must be willing to use effective contraception for 12 months following administration of pHMI-hPAH-TC-025 vector packaged in AAVHSC15 capsid which includes barrier contraception (male or female condom) during the 6 months after administration.
Exclusion Criteria:

Subjects with PKU that is not due to PAH deficiency.
Presence of anti-AAVHSC15 neutralizing antibody (at titer > 1:5).
History of or positive test result for human immunodeficiency virus (HIV).
History of or positive test result for hepatitis C virus antibody or hepatitis B virus (defined as positive for both hepatitis B surface antigen and hepatitis B core antibody), or current treatment with an antiviral therapy, for hepatitis B or C.
History of significant underlying liver disease, liver transplant, genetic liver disease, cirrhosis, NASH, or other liver condition that would preclude participation in the study as determined by the investigator.
History og drug abuse or alcoholism that would limit participation in the study, as determined by the investigator or subjects who exceed moderate drinking levels defined as: >4 drinks on any single day or >14 drinks per week if male; >3 drinks on any single day or >7 drinks per week if female
ALT > 1.5× ULN and AST > 1.5× ULN.
Alkaline phosphates > 1.5× ULN.
Total bilirubin > 1.5× ULN, direct bilirubin ≥ 1.5× ULN.
Serum creatinine > 1.5× ULN.

TABLE 3-continued

Inclusion and Exclusion Criteria

Hematology values outside of the normal range (hemoglobin < 11.0 g/dL for males or <10.0 g/dL for females; white blood cells (WBC) <3,000/μL; absolute neutrophils <1500/μL; platelets <100,000/μL).
Hemoglobin A1c >7.9% or fasting glucose >200 mg/dL.
Any clinically significant abnormal laboratory result at screening, in the opinion of the Investigator.
Contraindication to corticosteroid use or conditions that could worsen in the presence of corticosteroids, as assessed and determined by the investigator.
Previously received gene therapy for the treatment of any condition.
Subject is pregnant, breastfeeding, or intends to become pregnant during the study period.
Scheduled or anticipated major surgery in the 12 weeks following investigational gene therapy infusion for this study.
Use in past 30 days of levodopa.
Use of any investigational products within 30 days prior to screening.
Current enrollment in any other investigational study.
Presence of an untreated or inadequately treated active infection or an infection requiring systemic antiviral or antimicrobial therapy at any time during the screening period.
Use of any medication that is intended to treat PKU, including the use of large neutral amino acids (LNAAs), within 30 days prior to administration of study drug.
Current body mass index (BMI) ≥35 kg/m$^2$ (excludes Obesity Classes II and III).
Weight > 100 kg.
Have a clinically significant medical condition that in the investigator's opinion would pose an unnecessary risk (including history of chronic infection such as HIV or other chronic diseases), limit the participation of the subject in the study or impact the ability to interpret study results.
Has a malignancy, or history of malignancy, with the exception of successfully treated basal or squamous cell carcinoma of the skin.
Any other condition that would not allow the potential subject to complete follow-up examinations during the course of the study, or in the opinion of the investigator, makes the potential subject unsuitable for the study.

Figure 4:
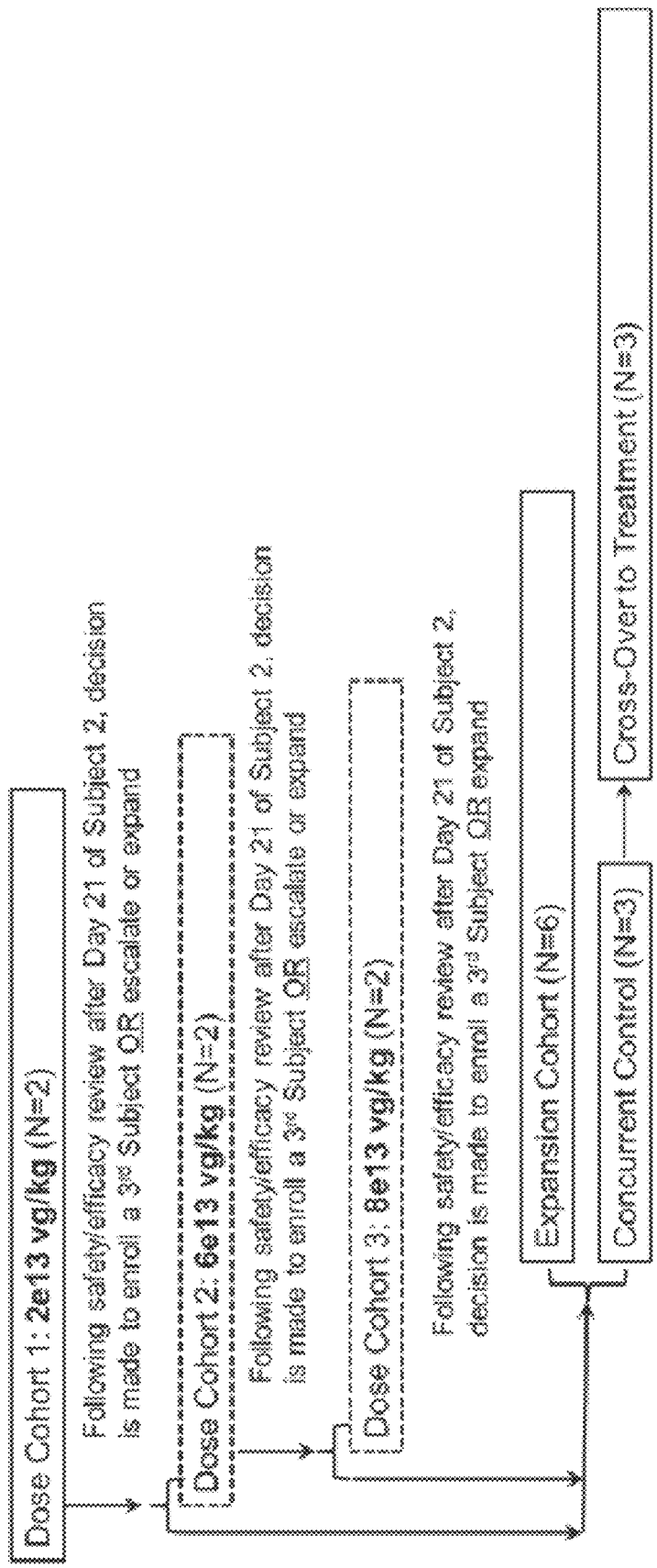
FIG. 4 is a schematic showing the design of an open-label, randomized, concurrently-controlled, dose escalation study of a single, ascending dose of a rAAV comprising the pHMI-hPAH-TC-025 vector packaged in AAVHSC15 capsid, in adult subjects with PAH deficiency.

Investigational Product, Dosage, and Mode of Administration pHMI-hPAH-TC-025 vector packaged in AAVHSC15 capsid will be administered intravenously over approximately 2-4 hours in the clinical research unit setting. The 3 cohorts of dose levels of pHMI-hPAH-TC-025 vector packaged in AAVHSC15 capsid to be investigated in the study are: (1) 2e13 vg/kg; (2) 6e13 vg/kg; (3) 8e13 vg/kg; and (4) 1e14 vg/kg. Upper limit of dosage will be 2e14 vg/kg. FIG. 4 is a study design schematic showing dose cohorts 1 to 3.

One day prior to administration of pHMI-hPAH-TC-025 vector packaged in AAVHSC15 capsid, subjects will be started on prophylactic oral prednisolone therapy which will be administered for 20 weeks as follows:
  Prednisolone 60 mg/day×2 weeks
  Prednisolone 40 mg/day×6 weeks
  Prednisolone 30 mg/day×3 weeks
  Prednisolone 20 mg/day×3 weeks
  Prednisolone 10 mg/day×5 weeks
  Prednisolone 5 mg/day×1 week (the investigator has the discretion to continue the 5 mg/day dose for a total of 2 weeks (i.e., 1 additional week) based on clinical judgment)

If a subject experiences elevated AST and/or ALT >2×ULN during the prophylactic prednisolone regimen, the steroid will be re-escalated or re-started at 60 mg/day, and then tapered again, according to the above schedule.

If a subject experiences elevated AST and/or ALT >2×ULN following the end of the prophylactic prednisolone regimen, the steroid will be re-started according to the following schedule, with modification allowed by the Investigator (in consultation with the Sponsor Medical Monitor or designee) based on laboratory parameters, the subject's medical history and clinical course, and/or subject tolerance of the regimen:

Prednisolone 60 mg/day×2 weeks or until ALT and AST levels have declined to ≤subject's baseline levels
Prednisolone 40 mg/day×2 weeks
Prednisolone 30 mg/day×2 weeks
Prednisolone 20 mg/day×2 weeks
Prednisolone 10 mg/day×2 weeks
Prednisolone 5 mg/day×2 weeks The prednisolone taper below 60 mg/day should not be started until the ALT and AST have declined to baseline (pre-administration) levels, provided the subject tolerates the regimen. The dose of 60 mg/day may be continued up to 4 weeks, or the dose re-escalated to that level, if the ALT/AST rise again and/or it is otherwise determined to be necessary in the judgment of the Investigator in consultation with the Sponsor's Medical Monitor or designee. After the ALT/AST have reduced again and/or the clinical situation is controlled, the subsequent taper may then proceed. The 60 mg/day dose should not exceed 4 weeks.

Subjects whose transaminase values continue to rise at 60 mg/day or 40 mg/day should be considered for treatment with intravenous methylprednisolone instead of oral prednisolone at the discretion of the Investigator, in consultation with the Sponsor's Medical Monitor or designee.

If the Investigator determines that oral prednisone should be administered instead of oral prednisolone, the Investigator must discuss the rationale with the Sponsor's Medical Monitor or designee and obtain Sponsor's Medical Monitor's or designee's approval to allow this alternate steroid. It is anticipated that the dosing of prednisone and the taper schedule should be the same as that for prednisolone. The rationale, approval, and administration of prednisone instead of prednisolone must be documented in the subject's study record.

If acute illness with fever occurs while the subject is on 5 mg/day or 10 mg/day of prednisolone, the dose should be doubled for 48 hours and then resumed at the previous dose and tapering schedule.

At any time that a subject on steroids (and up to 6 months following steroid discontinuation) undergoes major surgery or experiences major trauma or illness, stress steroids should be administered according to standard of care. Subjects will be informed of the risks of steroids including HPA axis suppression and other steroid-related side effects.

The intention is that Investigators and subjects will follow the steroid regimens as described in the protocol. However, it is recognized that uncommon situations could arise in which it is in the best interest of the subject to have the steroid dose reduced or discontinued. The steroid regimens are intended to suppress or control the immune response to the gene therapy and thereby preserve gene expression in the hepatocytes. A potential additional goal for the steroid regimen that addresses increased LFTs is to protect the liver cells by addressing the liver inflammation, if severe. These factors need to be taken into account if the Investigator is considering reducing the dose of steroids or discontinuing the steroids in the setting of a clinically important event such as steroid-related psychosis or herpetic corneal ulceration. If the Investigator sees the need to reduce or discontinue the steroids, the Sponsor's Medical Monitor or designee must be consulted prior to the Investigator modifying the steroid dosing (unless time does not permit this in an immediately life-threatening situation).

Concomitant Therapy

Subjects will continue their usual dietary regimen during the screening period. The baseline diet will be established during the screening period, defined as ±25% of average total protein intake (intact and medical), whether Phe-restricted or unrestricted. The baseline diet will be maintained following administration of pHMI-hPAH-TC-025 vector packaged in AAVHSC15 capsid. A recommendation to modify the diet may be made at the discretion of the Investigator, Site Dietician, and in consultation with the Sponsor Medical Monitor or designee based on the following guidelines:

At 8 weeks, if three Phe values during the first 8 weeks are ≤360 μmol/L

Prior to 8 weeks, if three Phe values during the first 8 weeks (measured at least one week apart) are <120 μmol/L Subjects taking medications for the treatment of ADHD, depression, anxiety, or other psychiatric disorders at study entry must be on a stable dose for ≥8 weeks prior to administration of pHMI-hPAH-TC-025 vector packaged in AAVHSC15 capsid and must continue with the same dose regimen throughout the study, unless it is determined that changes should be made for medical reasons.

Use of any medications for PKU, including Kuvan®, LNAA, and Palynziq™ is prohibited for the duration of the study unless the plasma Phe concentration is considered to be unsafe for the subject, and it is determined that such treatment is medically necessary following modification of diet.

Objectives and Endpoints

The primary objective of the study is to evaluate the safety, tolerability, and efficacy of a single dose of pHMI-hPAH-TC-025 vector packaged in AAVHSC15 capsid when administered to subjects with phenylalanine hydroxylase (PAH) deficiency.

The primary safety endpoint is incidence and severity of treatment emergent adverse events (TEAEs) and serious TEAEs. The primary efficacy endpoint is incidence of sustained plasma Phe concentration of ≤360 μmol/L at 24 weeks following administration of pHMI-hPAH-TC-025 vector packaged in AAVHSC15 capsid. Sustained plasma Phe concentration is defined as at least two plasma Phe measurements ≤360 μmol/L between 16 and 24 weeks.

The secondary objectives of the study are to evaluate the effect of pHMI-hPAH-TC-025 vector packaged in AAVHSC15 capsid on plasma phenylalanine (Phe) concentration relative to treatment guidelines for PKU, to assess durability of response, and to characterize the presence of vector and immune response following administration of pHMI-hPAH-TC-025 vector packaged in AAVHSC15 capsid.

The key secondary endpoint is measurement of plasma Phe concentration at 24 weeks post-treatment. Additional secondary endpoints include:

Incidence of achieving a plasma Phe concentration ≤360 μmol/L at each time point during the study Incidence of achieving a plasma Phe concentration ≤120 μmol/L at each timepoint during the study Assessment of presence of vector DNA in blood Assessment of vector shedding in urine, stool, and saliva Measurement of anti-AAVHSC15 antibodies (IgG and neutralizing), anti-PAH transgene antibody titers, and cytotoxic T-lymphocyte response (ELISPOT).

Safety and tolerability (including incidence of dose-limiting toxicities)

Results

Figure 5A:
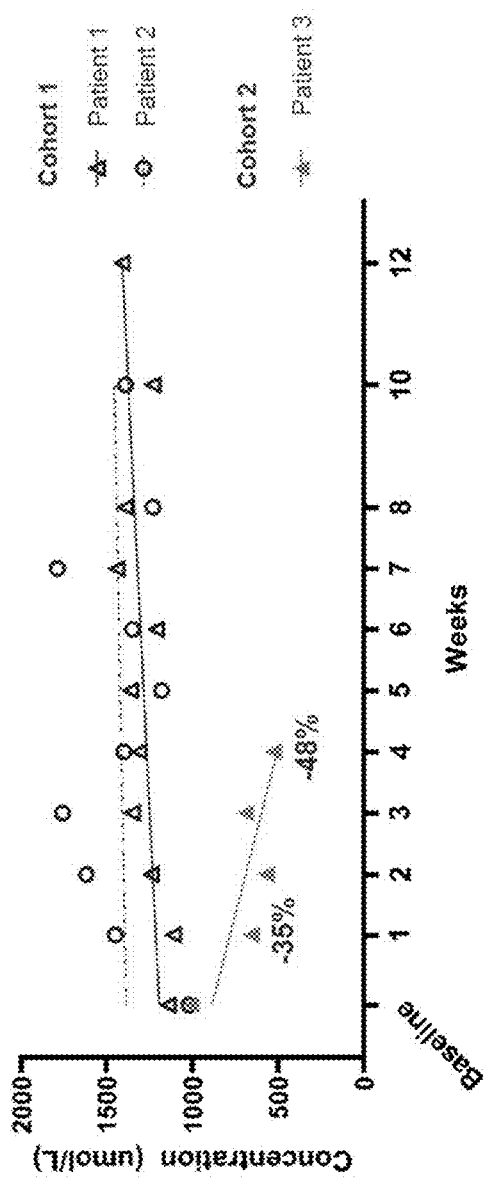
FIGS. 5A-5C show fasting Phe concentration (FIG. 5A), fasting Tyr concentration (FIG. 5B), and fasting Phe/Tyr ratio levels (FIG. 5C) of three patients dosed with an rAAV comprising the HMI-hPAH-TC-025 vector packaged in AAVHSC15.
Figure 5B:
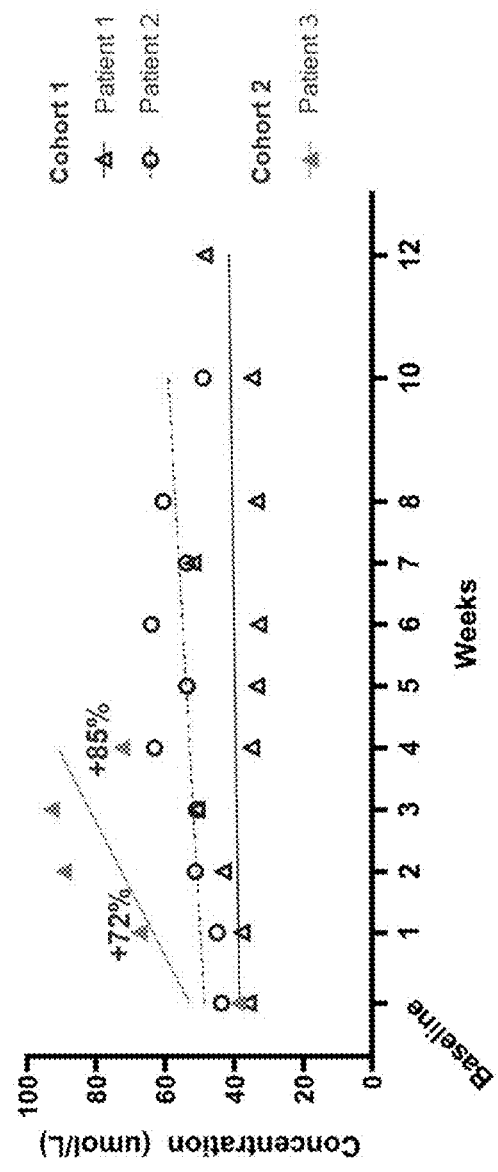
Figure 5C:
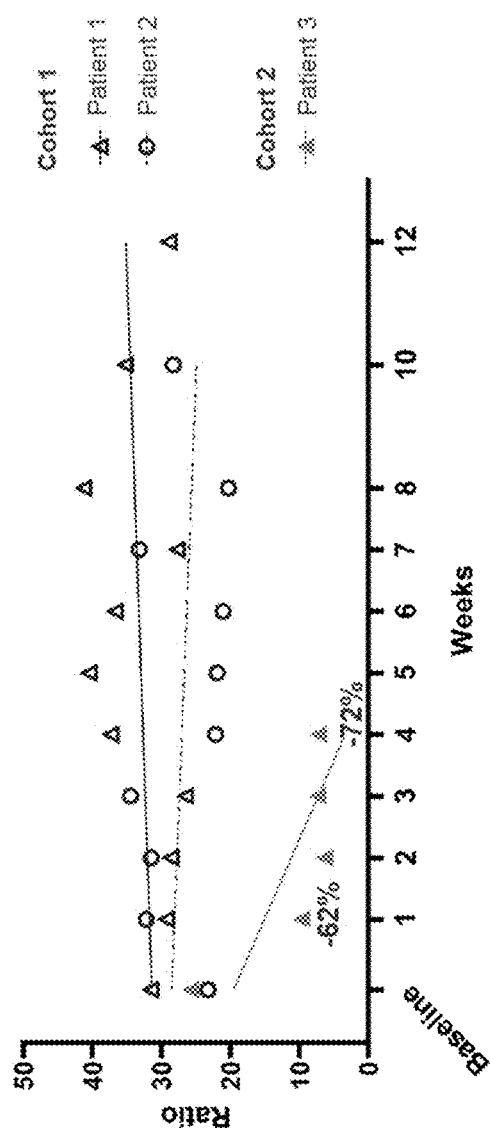

Two patients in Cohort 1 (low-dose) and one patient in Cohort 2 (mid-dose) received pHMI-hPAH-TC-025 vector packaged in AAVHSC15 capsid. Preliminary safety data from Cohorts 1 and 2 showed that administration of pHMI-hPAH-TC-025 vector packaged in AAVHSC15 capsid was well tolerated. FIGS. 5A-5C show data from the three dosed patients. The first patient in Cohort 2 indicated a dose-response effect with an observed reduction in phenylalanine (Phe) levels from baseline (FIG. 5A), increase in tyrosine (Tyr) (FIG. 5B), and reduction in the Phe/Tyr ratio (FIG. 5C), suggestive of increased enzymatic activity. Phe is a registrable endpoint in PKU, Tyr is a product of Phe metabolism and a precursor to neurotransmitters, and the Phe/Tyr ratio is a clinically relevant diagnostic measurement for PKU.

No treatment-emergent adverse events (TEAEs) or serious TEAEs were observed. All patients' ALT (alanine aminotransferase) and AST (aspartate aminotransferase) levels remained within the normal range. Cohort 1 safety profile enabled dose escalation to Cohort 2.

The first patient dosed in Cohort 2 experienced a reduction in Phe of 35% and 48% from baseline at weeks 1 and 4, respectively, as compared to Cohort 1, which generally did not show a reduction in Phe through weeks 10 and 12 (FIG. 5A). In FIG. 5A, the mean pre-treatment fasting Phe concentration in μmon was 1,187 for patient 1 (n=7 measurements); 1,178 for patient 2 (n=4 measurements); and 779 for patient 3 (n=5 measurements). The results are consistent with a dose-response effect of administration of pHMI-hPAH-TC-025 vector packaged in AAVHSC15 capsid. Per protocol, patient baseline is defined as one day prior to dosing. The first patient dosed in Cohort 2 also showed increases in Tyr levels of 72% and 85% at weeks 1 and 4, respectively, suggesting increased PAH enzyme activity (FIG. 5B). In FIG. 5B, the mean pre-treatment fasting Tyr concentration in μmol/L was 36.54 for patient 1 (n=7 measurements); 77.08 for patient 2 (n=4 measurements); and 49.00 for patient 3 (n=5 measurements). In addition, the patient experienced a 62% and 72% reduction in the Phe/Tyr ratio from baseline to weeks 1 and 4, respectively (FIG. 5C). All patients reported maintaining consistent protein intake pre- and post-treatment. In FIG. 5C, the mean pre-treatment fasting Phe/Tyr ratio level was 32.8 for patient 1 (n=7 measurements); 22.1 for patient 2 (n=4 measurements); and 16.3 for patient 3 (n=5 measurements).

Results

The above protocol was modified such that Cohort 3 was administered a dose of 1e14 vg/kg of AAV vector, rather than 8e13 vg/kg. Accordingly, pHMI-hPAH-TC-025 vector packaged in AAVHSC15 capsid was administered intravenously to six patients, according to three dosing cohorts (two patients each): (1) low-dose cohort: 2e13 vg/kg; (2) mid-dose cohort: 6e13 vg/kg; and (3) high-dose cohort: 1e14 vg/kg.

Table 4 shows a summary of the baseline characteristics for each patient.

TABLE 4

Patient Baseline Characteristics

| Cohort (dose level) | Patient # | Sex | Age | Baseline Phe (μmol/L) | Weeks Post-dosing | Pre-Existing Underlying Immune Conditions |
|---|---|---|---|---|---|---|
| Cohort 1 (low-dose) | 1 | F | 36 | 1140 | 52 (End of Study) | |
| | 2 | M | 49 | 1020 | 52 (End of Study) | |
| Cohort 2 (mid-dose) | 3 | M | 24 | 1010 | 48 | |
| | 4 | F | 21 | 1060 | 44 | Asthma, Seasonal Allergies |
| Cohort 3 (high-dose) | 5 | F | 31 | 1660 | 28 | Asthma, Eczema, Food Allergies, Environmental Allergies |
| | 6 | M | 33 | 1060 | 13 | |

Data for each individual patient is shown in FIGS. 6-11. FIGS. 6, 7, 8, 9, 10, and 11 are graphs showing the level of plasma Phe over time, for patients 1, 2, 3, 4, 5, and 6, respectively. Mean percent change from baseline (% CFB) values for Phe, Tyr, and Phe to Tyr ratio (P/T) were derived as follows: for each subject, a mean post-baseline value was derived for each analyte by summing all post-baseline values and dividing by the total number of visits. Mean post-baseline change was then calculated by subtracting the baseline value from the mean post-baseline value for each analyte. Mean percent change from baseline (% CFB) was derived by dividing the mean post-baseline change value by the baseline value and multiplying by 100 for each analyte. Diet Mean % CFB values for intact protein, total protein, Phe intake, and Tyr intake were derived as follows: for each subject, a mean post-baseline value was derived for each nutrient by summing all post-baseline values and dividing by the total number of visits. Mean post-baseline change was then calculated by subtracting the baseline value from the mean post-baseline value for each nutrient. Mean % CFB was derived by dividing the mean post-baseline change value by the baseline value and multiplying by 100 for each nutrient.

Figure 6:
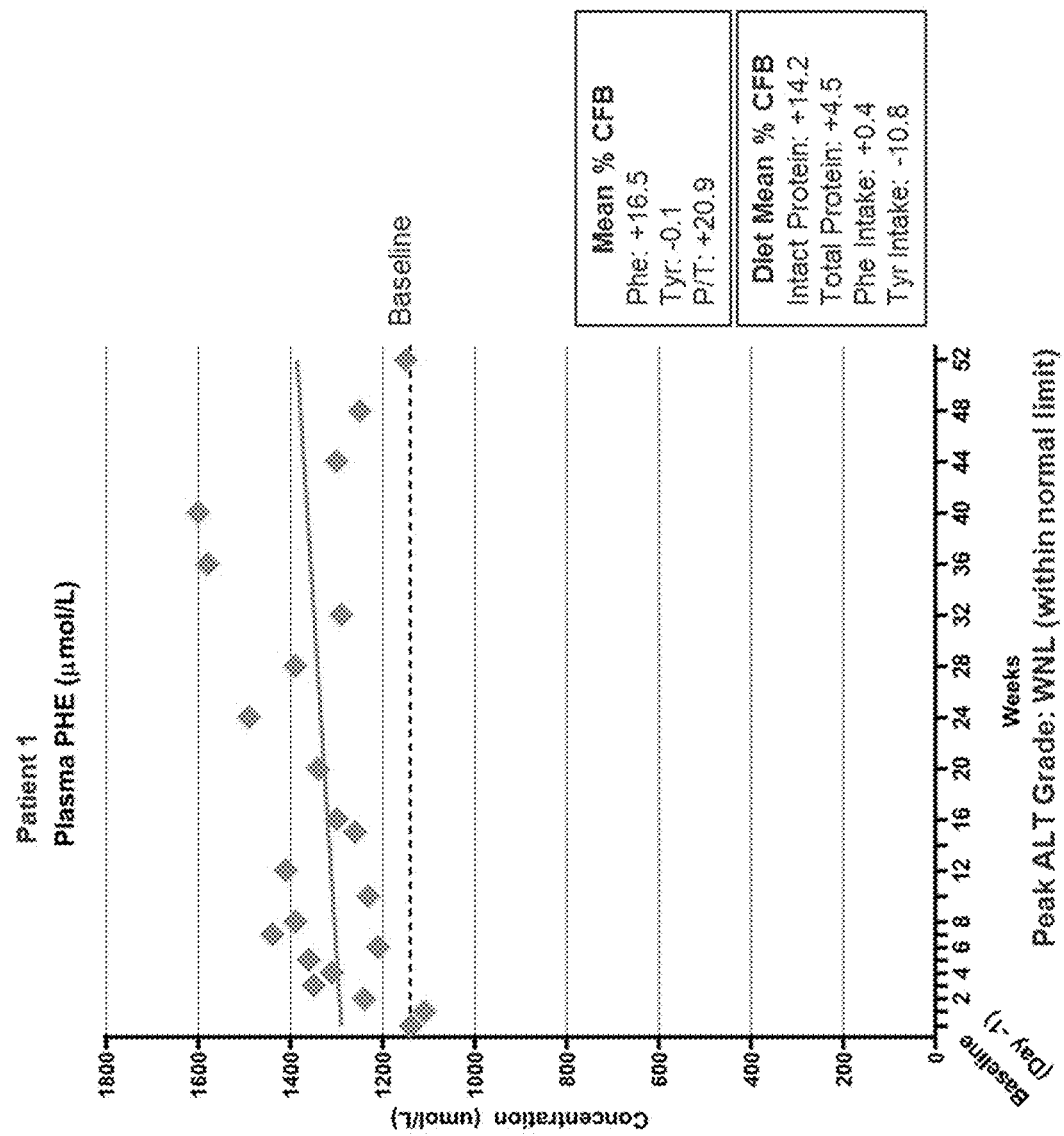
FIG. 6 is a graph showing the level of plasma Phe over time for patient 1.
Figure 7:
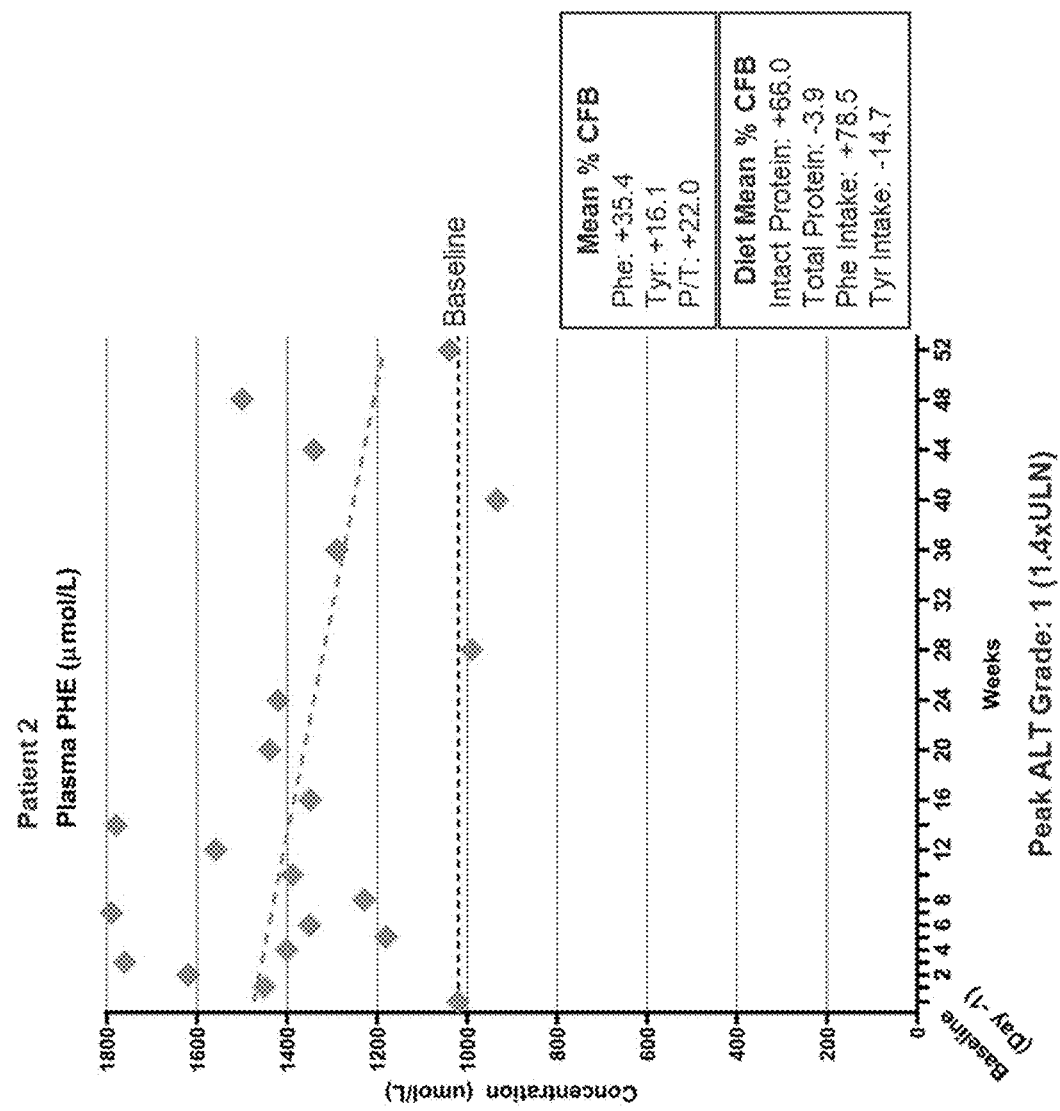
FIG. 7 is a graph showing the level of plasma Phe over time for patient 2.

As shown in FIGS. 6 and 7, a meaningful reduction in plasma Phe was not observed in patients 1 and 2, respectively.

Figure 8:
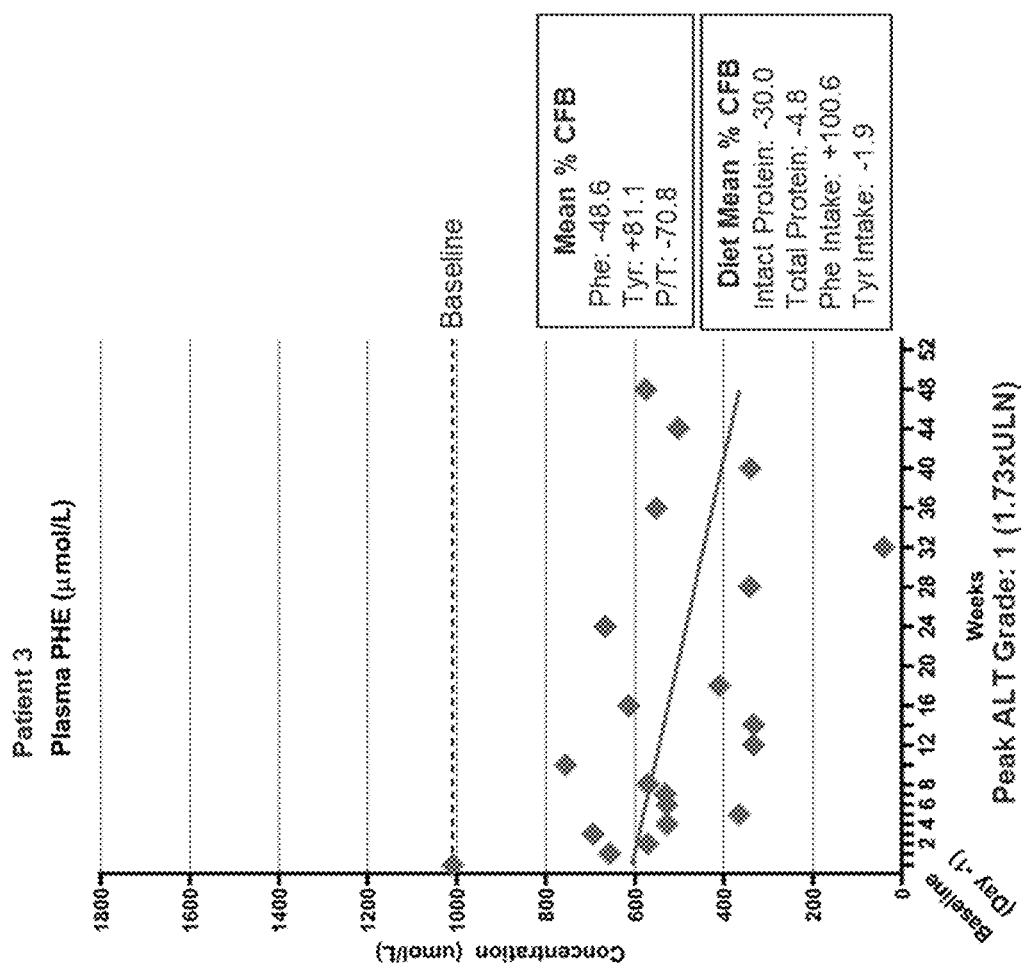
FIG. 8 is a graph showing the level of plasma Phe over time for patient 3.

As shown in FIG. 8, for patient 3, the mean % CFB showed a 48.6% reduction in plasma Phe, an 81.1% increase in tyrosine, and a 70.8% decrease in Phe to Tyr ratio. Without being bound to any theory, this indicates PAH enzymatic activity and more normal metabolism.

Figure 9:
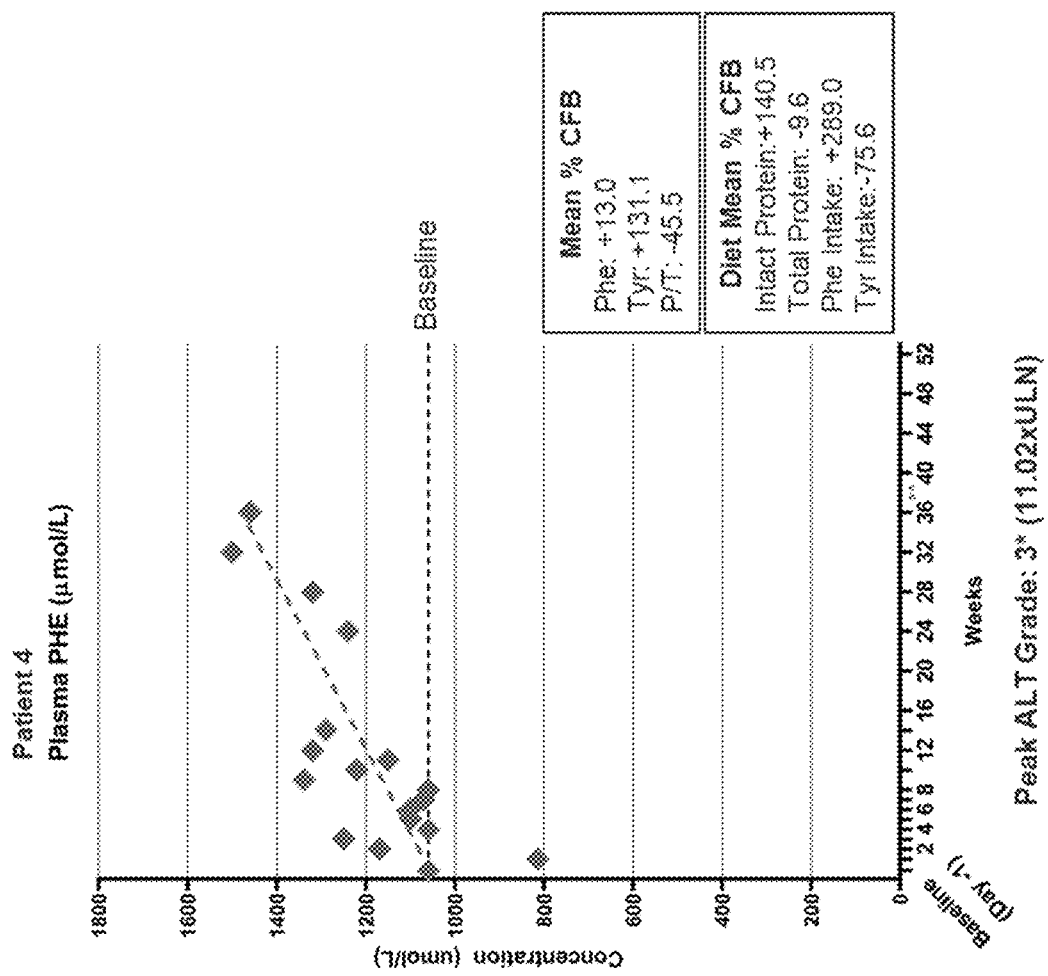
FIG. 9 is a graph showing the level of plasma Phe over time for patient 4.

As shown in FIG. 9, a reduction in the level of plasma Phe was not observed for patient 4. Despite the mean % CFB showing a 13% increase in plasma Phe, this patient experienced a dramatic mean % CFB increase in tyrosine of 131.1% and a decrease in Phe to Tyr ratio of 45.5%. Without being bound to any theory, this indicates PAH enzymatic activity that was enough to improve tyrosine, but not enough to reduce Phe. ** indicates that this patient began additional PKU medication after Week 36.

Figure 10:
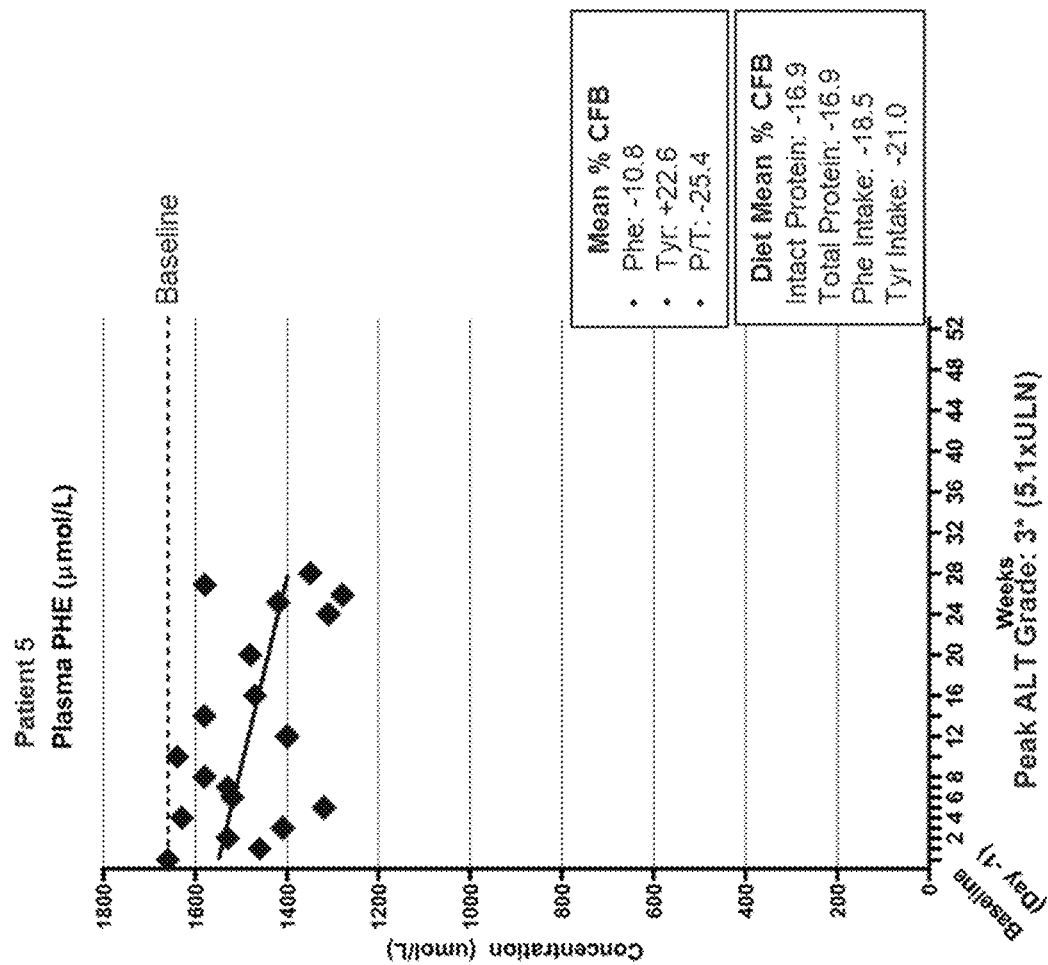
FIG. 10 is a graph showing the level of plasma Phe over time for patient 5.

As shown in FIG. 10, for patient 5, the mean % CFB showed a 10.8% reduction in plasma Phe, a 22.6% increase in tyrosine, and a 25.4% decrease in Phe to Tyr ratio.

Figure 11:
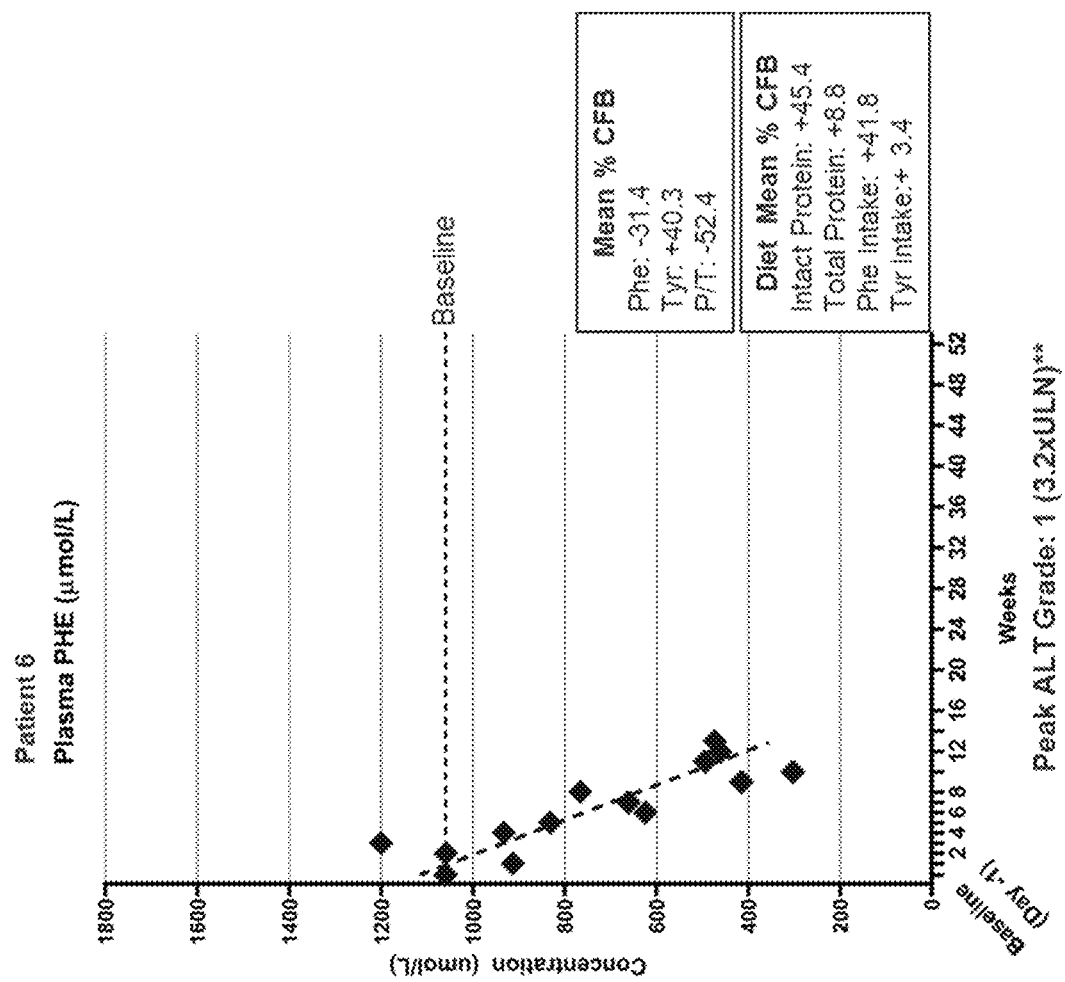
FIG. 11 is a graph showing the level of plasma Phe over time for patient 6.

As shown in FIG. 11, a marked reduction in plasma Phe was observed for patient 6. For patient 6, the mean % CFB showed a 31.4% reduction in plasma Phe, a 40.3% increase in 40.3%, and a 52.4% decrease in Phe to Tyr ratio. Without being bound to any theory, this indicates PAH enzymatic activity and more normal metabolism. ** indicates that patient 6 Grade 1 was based on a baseline ALT value above ULN.

In FIGS. 6-11, WNL represents within normal of alanine aminotransferase (ALT) level for the reference laboratory, and ULN represents upper limit of normal of ALT level for the reference laboratory. P/T represents Phe/Tyr ratio, CFB represents change from baseline for last value, and * indicates a patient having a pre-existing immune condition. ALT Grades are based on Common Terminology Criteria for Adverse Events (CTCAE) Version 5.

Figure 12:
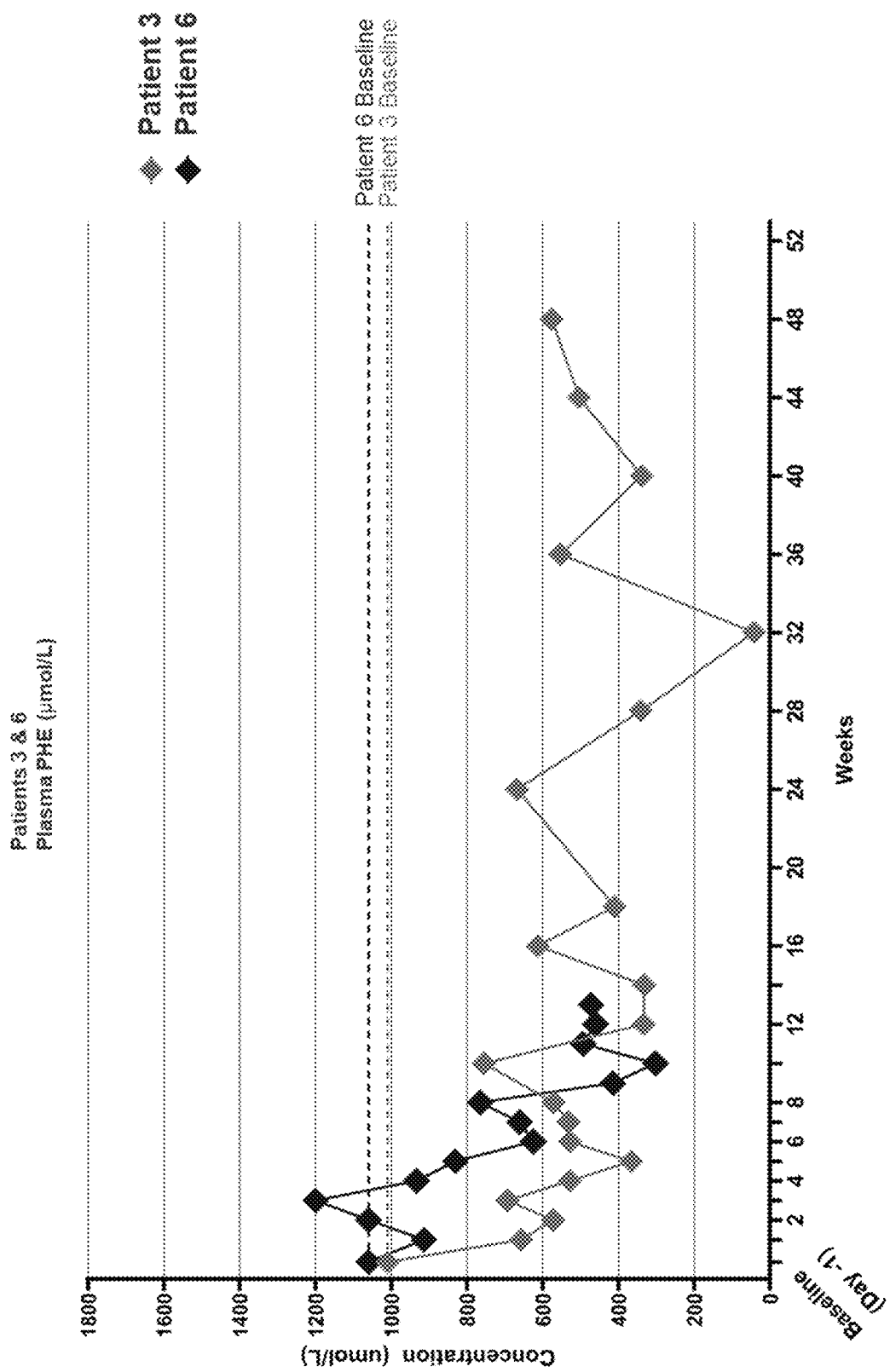
FIG. 12 is a graph showing the level of plasma Phe over time, for patients 3 and 6.

FIG. 12 is a graph showing the level of plasma Phe over time, for patients 3 and 6, and shows that these patients have a similar trajectory in Phe reductions.

Figure 13:
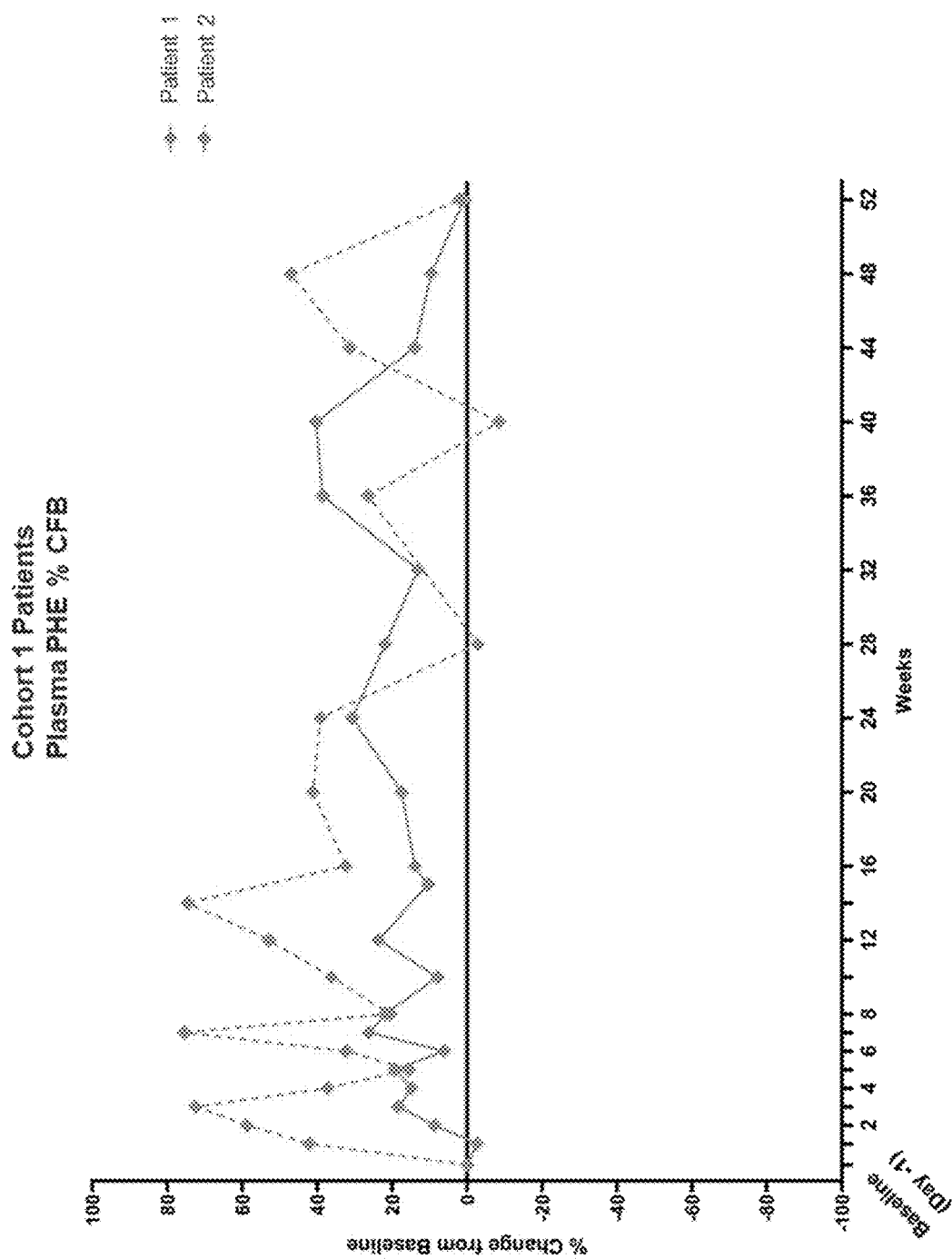
FIG. 13 is a graph showing the percent change from baseline of the level of plasma Phe over time, for patients of Cohort 1.

FIG. 13 is a graph showing the percent change from baseline (% CFB) of the level of plasma Phe over time, for patients of Cohort 1.

Figure 14:
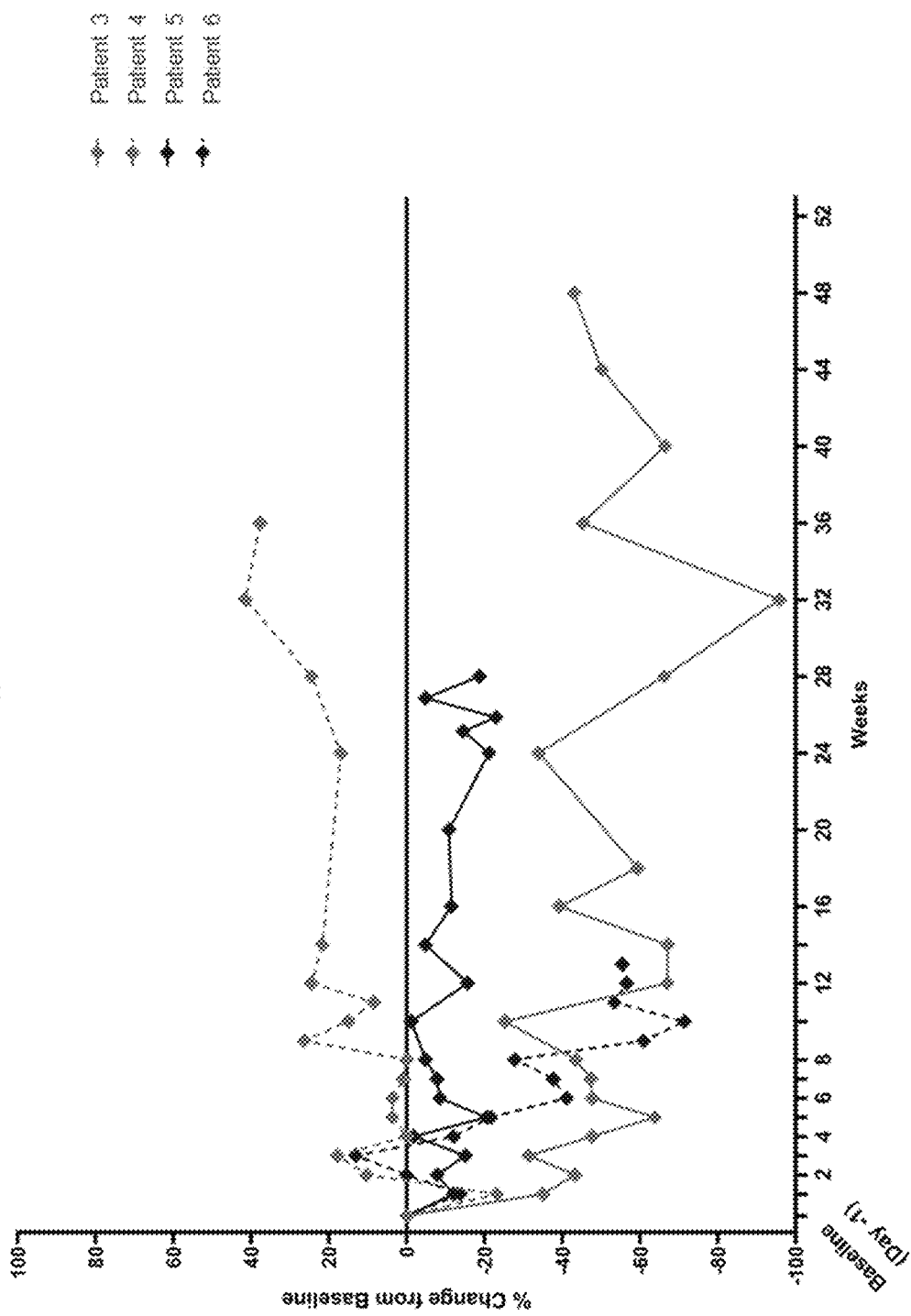
FIG. 14 is a graph showing the percent change from baseline of the level of plasma Phe over time, for patients of Cohorts 2 and 3.

FIG. 14 is a graph showing the percent change from baseline (% CFB) of the level of plasma Phe over time, for patients of Cohorts 2 and 3. A comparison of mean % CFB between patients of Cohort 1 and patients of Cohorts 2 and 3 shows that significant plasma Phe reductions were observed at the higher doses ($p<0.004$; Post-hoc comparison of Cohort 1 vs Cohorts 2&3 using repeated measures MANOVA/regression analysis).

In FIGS. 13 and 14, analyses were conducted by first calculating % CFB PHE at each visit for all subjects. % CFB was then compared between cohorts using a repeated measures regression to account for the within subject correlation due to the multiple follow-up visits, with % CFB as the dependent variable and cohort, baseline PHE values and study day of the visit included as independent variables.

Significant reductions in plasma Phe levels were observed in mid- and high-dose cohorts, compared to low-dose Cohort 1 ($p<0.004$; Post-hoc comparison of Cohort 1 vs Cohorts 2&3 using repeated measures MANOVA/regression analysis). Plasma Phe levels below 360 µmol/L (American College of Medical Genetics (ACMG) target Phe levels) were achieved in Cohort 2, with five values out to 48 weeks post-administration for patient 3; and Cohort 3, with one value out to 13 weeks post-administration for patient 6. Phe reduction, Tyr increase, and Phe/Tyr ratio decrease indicated PAH enzymatic activity.

The majority of patients self-liberalized dietary intact protein, e.g., increased their dietary intake of natural protein, and/or Phe intake. Table 5 shows a summary of change in protein intake for each patient. For each subject, a mean post-baseline value was derived for each nutrient by summing all post-baseline values and dividing by the total number of visits. Mean post-baseline change was then calculated by subtracting the baseline value from the mean post-baseline value for each nutrient. Mean % CFB was derived by dividing the mean post-baseline change value by the baseline value and multiplying by 100 for each nutrient.

TABLE 5

Change in Patient Dietary Protein Intake

| Cohort (dose level) | Patient | Mean % Change From Baseline | | | |
|---|---|---|---|---|---|
| | | Intact Protein | Total Protein | Phe Intake | Tyr Intake |
| Cohort 1 (low-dose) | 1 | +14.2 | +4.5 | +0.4 | −10.8 |
| | 2 | +66.0 | −3.9 | +78.5 | −14.7 |

TABLE 5-continued

Change in Patient Dietary Protein Intake

| Cohort (dose level) | Patient | Mean % Change From Baseline | | | |
|---|---|---|---|---|---|
| | | Intact Protein | Total Protein | Phe Intake | Tyr Intake |
| Cohort 2 (mid-dose) | 3 | −30.0 | −4.8 | +100.6 | −1.9 |
| | 4 | +140.5 | −9.6 | +289.0 | −75.6 |
| Cohort 3 (high-dose) | 5 | −16.9 | −16.9 | −18.5 | −21.0 |
| | 6 | +45.4 | +8.8 | +41.8 | +3.4 |

It was found that pHMI-hPAH-TC-025 vector packaged in AAVHSC15 capsid was generally well tolerated. No treatment-related serious adverse events (SAEs) were reported in the six dosed patients. One non-treatment-related SAE was observed in a patient that developed Herpes zoster.

Transaminitis, as evidenced by elevated ALT, occurred in five patients. ALT elevations in Cohorts 2 and 3 were managed with increased steroids, as needed. Two Grade 3 ALT elevations were observed in patients 4 and 5, both with pre-existing immune conditions. Normal cortisol levels were observed in patient 4 during planned high-dose, prophylactic steroid therapy. The severity of ALT increase was found to be associated with pre-existing immune conditions. Without being bound to any theory, ALT increases may impact efficacy of pHMI-hPAH-TC-025 vector packaged in AAVHSC15 capsid. In Cohorts 2 and 3, Phe reductions were found to be greater in patients with Grade 1 ALT elevations compared to patients with Grade 3 ALT elevations ($p<0.05$; Post-hoc comparison of Patients 3 and 6 vs Patients 4 and 5 using repeated measures MANOVA/regression analysis). Table 6 summarizes the ALT elevation status for each patient. ALT Grades are based on Common Terminology Criteria for Adverse Events (CTCAE) Version 5.

TABLE 6

Patient ALT Elevation Status

| Patient # | Peak ALT Grade (times ULN) |
|---|---|
| 1 | WNL |
| 2 | Grade 1 (1.4 × ULN) |
| 3 | Grade 1 (1.73 × ULN) |
| 4 | Grade 3 (11.02 × ULN) |
| 5 | Grade 3 (5.1 × ULN) |
| 6 | Grade 1 (3.2 × ULN)* |

*Grade 1 based on baseline ALT value above ULN.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

We claim:

1. A method for treating a subject having phenylketonuria (PKU), the method comprising administering to the subject an rAAV at a dose of about 6e13 vg/kg to about 1e14 vg/kg, wherein the rAAV comprises:
   (a) an AAV capsid comprising:
      a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R;
      a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or
      a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and
   (b) a transfer genome comprising a silently altered PAH coding sequence operably linked to a transcriptional regulatory element, wherein the silently altered PAH coding sequence comprises a nucleotide sequence having at least 95% sequence identity to the sequence set forth in SEQ ID NO: 1, and encodes the amino acid sequence set forth in SEQ ID NO:13.

2. The method of claim 1, wherein:
   the transcriptional regulatory element is capable of mediating transcription in a cell of the liver, the kidney, the brain, the pituitary gland, the adrenal gland, the pancreas, the urinary bladder, the gallbladder, the colon, the small intestine, or the breast;
   the transcriptional regulatory element comprises a human hepatic control region 1 (HCR1) comprising the nucleotide sequence set forth in SEQ ID NO:2;
   the transcriptional regulatory element comprises a human a1-antitrypsin (hAAT) promoter comprising the nucleotide sequence set forth in SEQ ID NO:3;
   the transcriptional regulatory element comprises an SV40 intron comprising the nucleotide sequence set forth in SEQ ID NO:4; or
   the transcriptional regulatory element comprises the nucleotide sequence set forth in SEQ ID NO:5.

3. The method of claim 1, wherein the transfer genome further comprises an SV40 polyadenylation sequence 3' to the PAH coding sequence, wherein the SV40 polyadenylation sequence comprises the nucleotide sequence set forth in SEQ ID NO:6.

4. The method of claim 1, wherein the transfer genome further comprises a 5' inverted terminal repeat (5' ITR) nucleotide sequence 5' of the genome, and a 3' inverted terminal repeat (3' ITR) nucleotide sequence 3' of the genome, optionally wherein the 5' ITR nucleotide sequence has at least 95% sequence identity to SEQ ID NO:8, and the 3' ITR nucleotide sequence has at least 95% sequence identity to SEQ ID NO:9.

5. The method of claim 1, wherein the transfer genome comprises the nucleotide sequence set forth in SEQ ID NO:7 or 10.

6. The method of claim 1, wherein the silently altered PAH coding sequence comprises a nucleotide sequence having at least 99% sequence identity to the sequence set forth in SEQ ID NO: 1.

7. The method of claim 1, wherein:
   the AAV capsid comprises a capsid protein comprising the amino acid sequence of amino acids 203-736 of SEQ ID NO:11, a capsid protein comprising the amino acid sequence of amino acids 138-736 of SEQ ID NO:11, and/or a capsid protein comprising the amino acid sequence of amino acids 1-736 of SEQ ID NO:11; or
   the amino acid sequence of the capsid protein consists of the amino acid sequence of amino acids 203-736 of SEQ ID NO:11, the amino acid sequence of the capsid protein consists of the amino acid sequence of amino acids 138-736 of SEQ ID NO:11, and/or the amino acid sequence of the capsid protein consists of the amino acid sequence of amino acids 1-736 of SEQ ID NO:11.

8. The method of claim 1, wherein the rAAV is administered as a single dose or as multiple doses.

9. The method of claim 1, wherein the rAAV is administered intravenously.

10. The method of claim 1, wherein the subject is a pediatric or an adult subject.

11. The method of claim 1, wherein the subject is administered a first immunosuppressant prior to administration of the rAAV, optionally wherein:
   the first immunosuppressant is administered one day prior to the administration of the rAAV; and/or the first immunosuppressant is administered to the subject for about 20 or about 21 weeks.

12. The method of claim 11, wherein the first immunosuppressant is administered according to the following sequential dosing regimen:
   (1) 60 mg/day in prednisolone equivalents for two weeks;
   (2) 40 mg/day in prednisolone equivalents for six weeks;
   (3) 30 mg/day in prednisolone equivalents for three weeks;
   (4) 20 mg/day in prednisolone equivalents for three weeks;
   (5) 10 mg/day in prednisolone equivalents for five weeks; and
   (6) 5 mg/day in prednisolone equivalents for one or two weeks.

13. The method of claim 12, wherein the first immunosuppressant is a glucocorticosteroid, optionally wherein the first immunosuppressant is prednisolone.

14. The method of claim 12, wherein:
   if the subject exhibits a level of a liver transaminase that is at least about 2 times the upper limit of normal (ULN) at any time during the sequential dosing regimen, the sequential dosing regimen will be restarted from step (1); or
   if the subject exhibits a level of a liver transaminase that is at least about 2 times ULN after completion of step (6), the subject is further administered the first immunosuppressant according to the following sequential dosing regimen:
   (7) 60 mg/day in prednisolone equivalents for two to four weeks;
   (8) 40 mg/day in prednisolone equivalents for two weeks;
   (9) 30 mg/day in prednisolone equivalents for two weeks;
   (10) 20 mg/day in prednisolone equivalents for two weeks;
   (11) 10 mg/day in prednisolone equivalents for two weeks; and
   (12) 5 mg/day in prednisolone equivalents for two weeks.

15. The method of claim 14, wherein step (7) is performed until the level of the liver transaminase has declined to about or less than about the subject's baseline level of the liver transaminase, optionally wherein:
   the subject's baseline level of the liver transaminase is the level of the liver transaminase in the subject prior to receiving the rAAV;
   the subject's baseline level of the liver transaminase is within a normal range; and/or
   the subject's baseline level of the liver transaminase is at about an upper limit of normal (ULN) for the liver transaminase.

16. The method of claim 14, wherein the liver transaminase is alanine aminotransferase (ALT) or aspartate aminotransferase (AST), optionally wherein:
   the normal range of ALT is from 0 to about 63 U/L;
   the normal range of AST is from 0 to about 57 U/L;
   the ULN for ALT is from about 30 to about 63 U/L; or
   the ULN for AST is about 34 to about 57 U/L.

17. A method for treating a subject having PKU, the method comprising intravenously administering to the subject an rAAV at a dose of about 6e13 vg/kg, about 8e13 vg/kg, or about 1e14 vg/kg, wherein the rAAV comprises:
   (a) an AAV capsid comprising:
      a capsid protein comprising an amino acid sequence having at least 95% sequence identity with the amino acid sequence of amino acids 203-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R;
      a capsid protein comprising an amino acid sequence having at least 95% sequence identity with the amino acid sequence of amino acids 138-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and/or
      a capsid protein comprising an amino acid sequence having at least 95% sequence identity with the amino acid sequence of amino acids 1-736 of SEQ ID NO:11, wherein the amino acid in the capsid protein corresponding to amino acid 346 of SEQ ID NO:11 is A, and wherein the amino acid in the capsid protein corresponding to amino acid 505 of SEQ ID NO:11 is R; and
   (b) a transfer genome comprising the nucleotide sequence set forth in SEQ ID NO:7 or SEQ ID NO:10.

* * * * *